US008513389B2

(12) United States Patent
Presta et al.

(10) Patent No.: US 8,513,389 B2
(45) Date of Patent: Aug. 20, 2013

(54) ENGINEERED ANTI-IL-23P19 ANTIBODIES

(75) Inventors: Leonard G. Presta, San Francisco, CA (US); Brian M. Beyer, Matawan, NJ (US); Richard N. Ingram, Scotch Plains, NJ (US); Peter Orth, New York, NY (US); Yan-Hui Liu, Murray Hill, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/530,854

(22) Filed: Jun. 22, 2012

(65) Prior Publication Data

US 2013/0039916 A1 Feb. 14, 2013

Related U.S. Application Data

(63) Continuation of application No. 12/527,456, filed as application No. PCT/US2008/002394 on Feb. 21, 2008, now abandoned.

(60) Provisional application No. 60/891,413, filed on Feb. 23, 2007.

(51) Int. Cl.
*C07K 16/24* (2006.01)

(52) U.S. Cl.
USPC ............. 530/387.1; 530/388.1; 530/388.23

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 6,096,289 A | 8/2000 | Goldenberg | |
| 6,495,667 B1 | 12/2002 | Bazan | |
| 6,610,285 B1 | 8/2003 | Hirata | |
| 6,632,927 B2 | 10/2003 | Adair et al. | |
| 7,090,847 B1 | 8/2006 | Oppmann et al. | |
| 7,608,690 B2 | 10/2009 | Bazan | |
| 2006/0063228 A1 | 3/2006 | Kasaian et al. | |
| 2006/0093600 A1 | 5/2006 | Bedian et al. | |
| 2006/0251658 A1 | 11/2006 | Ledbetter et al. | |
| 2007/0009526 A1 | 1/2007 | Benson et al. | |
| 2007/0048315 A1 | 3/2007 | Presta | |
| 2009/0123479 A1 | 5/2009 | Bembridge et al. | |

FOREIGN PATENT DOCUMENTS

| | | |
|---|---|---|
| EP | 0 438 310 A1 | 7/1991 |
| EP | 0 239 400 B1 | 8/1994 |
| WO | WO 00/53631 | 9/2000 |
| WO | WO 01/18051 | 3/2001 |
| WO | WO 2004/071517 | 8/2004 |
| WO | WO 2004/081190 | 9/2004 |
| WO | WO 2005/047324 | 5/2005 |
| WO | WO 2005/047326 | 5/2005 |
| WO | WO 2005/052157 | 6/2005 |
| WO | WO 2006/068987 | 6/2006 |
| WO | WO 2007/005955 | 1/2007 |
| WO | WO 2007/024846 | 3/2007 |
| WO | WO 2007/027714 | 3/2007 |
| WO | WO 2007/076524 | 7/2007 |
| WO | WO 2007/147019 | 12/2007 |
| WO | WO 2008/103432 | 8/2008 |
| WO | WO 2008/103473 | 8/2008 |
| WO | WO 2008/134659 | 11/2008 |
| WO | WO 2009/068627 | 6/2009 |
| WO | WO 2009/082624 | 7/2009 |

OTHER PUBLICATIONS

Aggarwal et al. (2003) *J. Biol. Chem.* 278(3):1910-1914, "Interleukin-23 promotes a distinct CD4 T cell activation state characterized by the production of interleukin-17".
Amit, et al. (1986) *Science* 233(4765):747-753 "Three-dimensional structure of an antigen-antibody complex at 2.8 a resolution".
Barbie & Lefranc (1998) *Experimental and Clinical Immunogenetics* 15:171-183, "The Human Immunoglobulin Kappa Variable (IGKV) Genes and Joining (IGKJ) Segments".
Beyer et al. (2008) *J. Mol. Biol.* 382:942-955, "Crystal structures of the pro-inflammatory cytokine Interleukin-23 and its complex with a high-affinity neutralizing antibody".
Bowman et al. (2006) *Curr. Opin. Infect. Dis.* 19(3):245-252, "Rationale and safety of anti-interleukin-23 and anti-interleukin-17A therapy".
Brorson et al. (1999) *J. Immunol.* 163:6694-6701, "Mutational Analysis of Avidity and Fine Specificity of Anti-Levan Antibodies".
Brummell et al. (1993) *Biochemistry* 32(4):1180-1187, "Probing the combining site of an anti-carbohydrate antibody by saturation-mutagenesis: role of the heavy-chain CDR3 residues".
Burks et al. (1997) *Proc. Natl. Acad. Sci. USA* 94(2):412-417, "In vitro scanning saturation mutagenesis of an antibody binding pocket".
Casset, et al. (2003) *BBRC* 307(1):198-205, "A peptide mimetic of an anti-CD4 monoclonal antibody by rational design".
Chen, et al. (1999) *J. Mol. Bio.* 293(4):865-881, "Selection and analysis of an optimized anti-VEGF antibody: crystal structure of an affinity-matured Fab in complex with antigen".
Chen et al. (2006) *J. Clin. Investigation* 116(5):1317-1326, "Anti-IL-23 therapy inhibits multiple inflammatory pathways and ameliorates autoimmune encephalomyelitis".
Chothia & Lesk (1987) *J. Mol. Biol.* 196: 901-917 "Canonical Structures for the Hypervariable Regions of Immunoglobulins".
Colman (1994) *Research in Immunol.* 145(1):33-36, "Effects of amino acid sequence changes on antibody-antigen interactions".
Cua & Kastelein (2006) *Nat. Immunol.* 7:557-559 "TGF-B, a 'double agent' in the immune pathology war".
Dall'Acqua (2006) *J. Immunol.* 177(2):1129-1138, "Modulation of the Effector Functions of a Human IgG1 through Engineering of Its Hinge Region".
Davies et al. (1996) *Immunotechnology* 2(3):169-179, "Affinity improvement of single antibody VH domains: residues in all three hypervariable regions affect antigen binding".
De Pascalis, et al. (2002) *The Journal of Immunology* 169(6):3076-3084, "Grafting of "Abbreviated" Complementarity-Determining Regions Containing Specificity-Determining Residues Essential for Ligand Contact to Engineer a Less Immunogenic Humanized Monoclonal Antibody".

(Continued)

*Primary Examiner* — Prema Mertz
(74) *Attorney, Agent, or Firm* — Gregory R. Bellomy

(57) ABSTRACT

Engineered antibodies to human IL-23p19 are provided, as well as uses thereof, e.g. in treatment of inflammatory, autoimmune, and proliferative disorders.

7 Claims, 6 Drawing Sheets

(56) References Cited

OTHER PUBLICATIONS

Dennis (2006) *Nature* 442(7104):739-741, "Cancer: off by a whisker".
Dong (2006) *Nat. Rev. Immunol.* 6(4):329-333 "Diversification of T-helper-cell lineages: finding the family root of IL-17-producing cells".
Gorman et al. (1991) *Proc. Natl. Acad. Sci. USA* 88:4181 "Reshaping a therapeutic CD4 antibody".
Hodgson (1991) *Biotechnology (NY)* 9:421-5 "Making Monoclonals in Microbes".
Holm, et al. (2007) *Mol. Immunol.* 44(6):1075-1084, "Functional mapping and single chain construction of the anti-cytokeratin 8 monoclonal antibody TS1".
Holt et al. (2003) *Trends in Biotechnology* 21(11):484-490, "Domain antibodies: proteins for therapy".
Hunter (2005) *Nature Reviews—Immunology* 5:521-531, "New IL-12-family members: IL-23 and IL-27, cytokines with divergent functions".
Iwakura & Ishigame (2006) *J. Clin. Invest.* 116:1218-1222 "The IL-23/IL-17 axis in inflammation".
Jang, et al. (1998) *Molec. Immunol.* 35(18):1207-1217, "The structural basis for DNA binding by an anti-DNA autoantibody".
Jones et al. (1986) *Nature* 321:522-525 "Replacing the complementarity-determining regions in a human antibody with those from a mouse".
Kabat & Wu (1991) *J. Immunol.* 147:1709 "Identical V Region Amino Acid Sequences and Segments of Sequences in Antibodies of Different Specificities".
Kobayashi, et al. (1999) *Protein Engineering* 12(10):879-844, "Tryptophan H33 plays an important role in pyrimidine (6-4) pyrimidone photoproduct binding by a high-affinity antibody".
Kunkel (1985) *Proc. Natl. Acad. Sci. U.S.A* 82:488-492, "Rapid and efficient site-specific mutagenesis without phenotypic selection".
Lefranc (2001) *Experimental and Clinical Immunogenetics* 18:100-116, "Nomenclature of the Human Immunoglobulin Heavy (IGH) Genes".
Lefranc (2001) *Experimental and Clinical Immunogenetics* 18:161-174 "Nomenclature of the Human Immunoglobulin Kappa (IGK) Genes".
Little et al. (2000) *Immunology Today* 21(8):364-370, "Of mice and men: hybridoma and recombinant antibodies".
MacCallum, et al. (1996) *J. Mol. Biol.* 262(5):732-745, "Antibody-antigen interactions: contact analysis and binding site topography".
Morelli et al. (2005) *J. Immunol.* 175:7905-7915, "CD4+ T cell responses elicited by different subsets of human skin migratory dendritic cells".
Nestle et al. (2007) *Clin. Immunology* 123:S62-S63, "Evidence for a Role of the Interleukin-23 Pathway in the Pathogenesis of Psoriasis".
Oppmann, et al. (2000) *Immunity* 13:715-725 "Novel p19 Protein Engages IL-12p40 to Form a Cytokine, IL-23, with Biological Activities Similar as Well as Distinct from IL-12".
Panka, et al. (1988) *Proc. Natl. Acad. Sci. USA* 85:3080-3084 "Variable region framework differences result in decreased or increased affinity of variant anti-digoxin antibodies".
Parham, et al.(2002) *J Immunol* 168:5699-708 "A Receptor for the Heterodimeric Cytokine IL-23 Is Composed of IL-12RB1 and a Novel Cytokine Receptor Subunit, IL-23R".
Presta (1992) *Curr. Op. Struct. Biol.* 2(4):593-596, "Antibody Engineering".
Presta (2005) *J. Allergy Clin. Immunol.* 116:731-736, "Molecular mechanisms in allergy and clinical immunology: selection, design, and engineering of therapeutic antibodies".
Queen et al. (1989) *Proc. Natl. Acad. Sci. USA* 86:10029 "A humanized antibody that binds to the interleukin 2 receptor".
R&D Systems, *de novo: New Products from R&D Systems*, Mar. 2004, pp. 1-10.
R&D Systems, *de novo: New Products from R&D Systems*, Jun. 2005, pp. 1-12.
Reissner & Aswad (2003) *Cell. Mol. Life Sci.* 60(7):1281-1295, "Deamidation and isoaspartate formation in proteins: unwanted alterations or surreptitious signals?"
Riechmann et al. (1988) *Nature* 332:323-329 "Reshaping human antibodies for therapy".
Rudikoff, et al. (1982) *Proc. Natl. Acad. Sci. USA* 79:1979-1983 "Single amino acid substitution altering antigen-binding specificity".
Salfeld (2007) *Nature Biotech.* 25(12):1369-1372, "Isotype selection in antibody engineering".
Sehy, et al. (2005) *FASEB Journal* vol. 19, No. 4, Suppl. S, Part 1, pp. A945-A946 "Unambiguous detection of IL-23 (p19/p40) protein in native samples using a novel enzyme-linked immunosorbent assay".
Stumhofer et al. (2006) *Nature Immunol.* 7:937, "Interleukin 27 negatively regulates the development of interleukin 17-producing T helper cells during chronic inflammation of the central nervous system".
Tato & O'Shea (2006) *Nature* 441:166-168 "What does it mean to be just 17?"
Vajdos, et al. (2002) *J. Mol. Biol.* 320(2):415-428, "Comprehensive functional maps of the antigen-binding site of an anti-ErbB2 antibody obtained with shotgun scanning mutagenesis".
Veldhoen (2006) *Immunity* 24:179-189 TGFB in the Context of an Inflammatory Cytokine Milieu Supports De Novo Differentiation of IL-17-Producing T Cells.
Verhoeyen et al. (1988) *Science* 239:1534-1536 "Reshaping Human Antibodies: Grafting an Antilysozyme Activity".
Verreck et al. (2004) *PNAS* 101(13):4560-4565, "Human IL-23-producing type 1 macrophages promote but IL-10-producing type 2 macrophages subvert immunity to (myco)bacteria".
Voskoglou-Nomikos (2003) *Clin. Can. Res.* 9(11):4227-4239, Clinical predictive value of the in vitro cell line, human xenograft, and mouse allograft preclinical cancer models.
Wiekowski, et al. (2001) *J. Immunol.* 166:7563-7570 "Ubiquitous Transgenic Expression of the IL-23 Subunit p19 Induces Multiorgan Inflammation, Runting, Infertility, and Premature Death".
Wu, et al. (1999) *J. Mol. Biol.* 294:151-162 "Humanization of a murine monoclonal antibody by simultaneous optimization of framework and CDR residues".

```
                                          ---CDRH1--
       7G10   EVQLQQSGPELVKPGASVKMSCKAS    GYTFTSNVMH    WVKQKPGQGLEWIG
       6H12   EVHLQQSGPELVKPGASVKMSCKAS    GYTFNRYLIH    WVKQKPGQGLEWIG
       13F11  EVQLQQSGPELVKPGASVKMSCKAS    GHTLTRYLMH    WVQQKPGQGLEWIG
       13B5   EVQLQQSGPELVKPGASVKMSCKAS    GYTFTRYLMH    WVKQKPGQGLEWIG
       7E2    EVQLQQSGPELVKPGASVKMSCKAS    GYTFTTYLMH    WVKQKPGQGLEWIG
       13G1   EVQLQQSGPELVKPGASVKMSCKAS    GYTFTSYLMH    WVKQKPGQGLEWIG
       11C10  EVQLQQSGPELVKPGASVKMSCKAS    GYTFTRYVMH    WVKQKPGQGLEWIG
       1E10   EVQLQQSGPELVKPGASVKMSCKAS    GYTFTSYVMH    WVKQKPGQGLEWIG
       30F11  EVQLQQSGPELLKPGASVKMSCKAS    AYTFTRYLIH    WVKQKPRQGLEWIG
       5B12   EVQLQQSGPELVKPGASVKMSCKAS    GYTFTSYVMH    WVKQKPGQGLEWIG
       6H4    EVQLQQSGPELVKPGASVKMSCKAS    GYTFTRYLMH    WVKQKPGQGLEWIG
       9C9    EVQLQQSGPELVKPGASVRMSCKAS    GYTFTSYLIH    WVKQKPGQGLEWIG
       11B10  EVQLQQSGPELVKPGASVKMSCKAS    GYTFTSYVMH    WVKQKPGQGLEWIG
       33D2   EVQLQQSGPELVKPGASVKMSCKAS    GYTFTSYLMH    WVKQKPGQGLEWIG
       20A9   EVQLKQSGLEVVKPGASVKMSCKAS    GYTFTAHLMH    WVKQRPGQGLEWIG
       22E9   EVQLQQSGPELVKPGASVKMSCKAS    GYTFTSYVMH    WVKQKPGQGLEWIG
       29D5   EVQLQQSGPELVKPGASVKMSCKAS    GYSFTSYVMH    WVKQKPGQGLEWIG
       21A10  EVQLQQSGPELVKPGASVKMSCKAS    GYTFTSYVMH    WVKQKPGQGLDWIG
       2G12   EVQLQQSGPELVKPGASVKMSCKAS    GYTFTCCILH    WVKQKPGQGLEWIG
       15G2   EVQLQQSGPELVKPGASVKMSCKAS    GYTFTNYLMH    WVKQKPGQGLEWIG
       18E1   EVQLQQSGPELVKPGASVKMSCKAS    GNTFTRYVMN    WVKQKPGQGLEWIG
       2C6    EVQLQQSGPELVKPGASVKMSCKAS    GYTFTRYLIH    WVKQKPGQGLEWIG
       conH   EVQLQQSGPELVKPGASVKMSCKAS    GYTFTSYLMH    WVKQKPGQGLEWIG
                                             R  VI
       V1-14  EFQLQQSGPELVKPGASVKMSCKAS    GYTFTSYVMH    WVKQKPGQGLEWIG 49A10  EVQLQQSGPELVKPGASVKISCKAS    GYTFTDYYMN    WVKQSHGKSLEWFG
       34E4   EVQLQQSGPELVKPGASVKMSCKAS    GYTFTAYNMH    WVKQSHGKSLEWIG
       8E9    EVQLQQSGPELVKPGASVKMSCKAS    GYTFTAYLIH    WVKQSHGKSLEWIG
       1D6    EVQLQQSGPDLVKPGASVKMSCKAS    GYTFTAYLIH    WVKRSHGKSLDWIG 34F9   QVQLQQSGAELAKPGASVKLSCKAS    GYTFPTFWMH    WVKQRPGQGLEWIG
       7D7    QVQLQQSGAELAKPGASVKLSCKAS    GYTFTNYWMD    WVKQRPGQGLEWIG 33B12  QVQLQQSGAELARPGASVKLSCKAS    GYTFTSYSLK    WVKQRTGQGLEWIG
       17G8   QAQLQQSGSELARPGASVKLSCKAS    GYTFTSYGIK    WVKQRTGQGLEWIG
       20A4   QAQLQQSGGELARPGASVKLSCKAS    GYTFTSYGIK    WVKQGTGQGLEWIG
       20H7   QAQLQQSGGELARPGASVKLSCKAS    GYTFTNYGIK    WVKQRTGQGLEWIG
       3C4    QVQLQQSGGELARPGASVKLSCKAS    GYTFTSYGIK    WVKQRFGQGLEWIG

3D7    QVQLQQSGPELVKPGASVKISCKAS    GYSFTSYYIH    WVKQRPGQGLEWIG

39G2   QVQLQQPGAELVRPGASVKLSCKAS    GYSFTSSWMN    WVKQRPGQGLEWIG
       35F12  QVQLQQPGAELMRPGASVRLSCKAS    GYSFTTSWMN    WVKQRPGQGLEWIG

14A3   EVILVESGGGFVKPGGSLKLSCAAS    GFTFSNYGMS    WVRQTPDKGLEWVA
       12C11  EVMLVESGGGLVKPGGSLKLSCAAS    GFTFSNYGMS    WVRQSPERGLEWVA

10H11  EVMLVESGGGLVKPGGSLKLSCAAS    GFTFSSYSMS    WVRQTPEKRLEWVA
       19E9   EVMLVESGGGLVKPGGSLKLSCAAS    GFTFSTYDMS    WVRQTPEKRLEWVA
       10G8   EVMLVESGGGLVKPGGSLKLSCAAS    GFTFSSYSMS    WVRQTPEKRLEWVA

16F7   EVQLVESGGDLVKPGGSLKLSCAAS    GFIFNSYGMS    WVRQTPDKRLEWVA
```

Figure 1A

```
                ------CDRH2------
        7G10    YINPYNDGTKYNEKFKG  KATLTSDKSSSTAYMELSSLTSEDSAVYYCAR
        6H12    YINPNNDGTNYNEKFKG  KATLTSDKSSSTAYMELSSLTSEDSAVYYCAA
        13F11   YINPYNDGTNYNEKFKG  KATLTSDKSSSTAYMELSSLTSEDSAVYYCAR
        13B5    YINPYNDGTNYNEKFKG  KATLTSDKSSSTAYMELSSLTSEDSAVYYCAR
        7E2     YINPYNDGTNYNEKFKG  KATLTSDKSSSTAYMELSSLTSEDSAVYYCTK
        13G1    YINPYNDGTNYNEKFKG  KATLTSDKSSSTAYMDLSSLTSEDSAVYYCAI
        11C10   YINPYDVPNYNENFKG   KATLTSDKSSSTASMELSSLTSEDSAVYYCAV
        1E10    YINPYNDGTNYNEKFKG  KATLTSDKSSSTAYMELSSLTSEDSAVYYCAS
        30F11   YINPYNDGTKYNEKFKG  KATLTSDKSSSTAYMELSSLTSEDSAVYYCAR
        5B12    YINPYNDGTNYNEKFKH  KATLTSDKSSSTAYMELSSLTSEDSAVYYCTS
        6H4     YINPYNDGTNYNEKFKG  KATLTSDKSSSTAYMELSSLTSEDSAVYYCAR
        9C9     YINPYNDGTNYNENFKG  KATLTSDKSSSTAYMELSSLTSEDSAVYYCAS
        11B10   YINPYNDGTNYNEKFKG  KATLTSDKSSSTAYMELGSLTSEDSAVYYCAS
        33D2    YINPYDGPKYNEQFKG   KATLTSDKSSNTAYMELSSLTSEDSAVYYCAR
        20A9    YINPYNDGTNYNEKFKG  KATLTSDKSSSTAFMELSSLTSEDSAVYYCAS
        22E9    YINPYNAGTNYNEKFKG  KATLTSDKSSSTAYMELSSLTSEDSAVYYCAS
        29D5    YINPYNDGTNYNEKFRG  KATLTSDKSSNTAYLDLSSLTSEDSAVYYCAS
        21A10   YINPYNDGTNYNEKFKG  KATLTSDKSSSTAYMELSSLTSEDSAVYYCTS
        2G12    YINPYNDGTKYNEKFKG  KATLTSDKSSRTAYMELSSLTSEDSAVYYCAR
        15G2    YINPYNDGTNYNEKFKG  KATLTSDKSSSTAYMELSSLTSEDSAIYFCTS
        18E1    YINPYNDGTNYNEKFKG  KATLTSDKSSTTAYMELSSLTSEDSAVYYCVH
        2C6     YVNPYNDGTNYNEKFRG  KATLTSDKSSSTAYMELSSLTSEDSAVYYCTS
        conH    YINPYNDGTNYNEKFKG  KATLTSDKSSSTAYMELSSLTSEDSAVYYCAS
                  K                                            TR
        V1-14   YIYPYNDGTKYNEKFKG  KATLTSDKSSSTAYMELSSLTSEDSAVYYCAR 49A10   DINPNNGDTSYNQKFKG  KATLTVDKSSSTAYMELRSLTSEDSADYYCAR
        34E4    YINPNNGIPNYNQKFKG  KATLTVNKSSSTAYMELRSLTSEDSAVFYCAL
        8E9     YINPNNGGTNYNQKFKD  KATLTVNKSSATAYMELRSLTSEDSAVFYCSS
        1D6     YINPNDGVTSYNQKFKG  KATLTVNKSSGTAYMELRSLTSEDAAVYYCTL 34F9    YINPSSGYTEYNQKFKD  KATLTADKSSSTAYMQLSSLTYEDSAVYYCAR
        7D7     YINPSSGYVEYNQKFKY  KATLTADKTSSTAYMQLSSLTYDDSAVYYCAR 33B12   EIHPRSGNTHYNEKFKG  KATLTADKSSSTAYMDLRSLTSEDSAVYFCAT
        17G8    EIFPRSGQTIYNENFKG  KATLTADKSSSTAYMELRSLTSEDSAVYFCAA
        20A4    EIFPRSGQTYYNEKFKG  KATLTADKSSSTAYMELRSLTSEDSAVYFCAS
        20H7    EIFPRSGQTIYNEKFKG  KATLTADKSSSTAYMELRSLTFEDSAVYFCAA
        3C4     EIFPRGGNTYYNEKFKG  KATLTADKSSSTAYMELRSLTSEDSAVYFCTA

3D7     WIFPGSGNTKYNEKFKG  KATLTADTSSTTAYMQLSSLTSEASAVYFCAR

39G2    MIHPSDSETRTNQKFKD  KATLTVDKSSSTAYMQLSSPTSEDSAVYYCAR
        35F12   MIHPSDSETRLNQNFKD  KATLTVDRSSSTAYMQLNSPTSEDSAVYYCAR

14A3    TISTGGRYIYYSDTVKG  RFTISRDNAKSTLYLKMSSLRSEDTAVHFCAR
        12C11   TISTGGRYTFYSDTVKG  RFTISRDNARNTLYLKMSSLISEDTAVHYCAR

10H11   TISRGGGNTYYPDSVKG  RFTISRDNANNNLFLRLSSLRSEDTALYYCAR
        19E9    TISRGGGNTYYPDSVKS  RFTISRDNAKNNLYLQMSSLRSVDTALYYCSR
        10G8    TISRGGGNTYYPDSVKG  RFTISRDNAKNNLYLRMSSLRSEDTALYYCAR

16F7    TISSGGRNTYYPDSVKG  RFTISRDNAKNTLYLQMSSLKSEDTAMYYCAR
```

Figure 1B

```
        -----CDRH3-----
7G10    NWDVAY            WGQGTLVTVSA
6H12    NWDQAY            WGQGTLVTVSA
13F11   NWDVAY            WGQGTLVTVSA
13B5    NWDVGGY           WGQGTTLTVSS
7E2     NWDKGY            WGQGTTLTVSS
13G1    NWDLAY            WGQGTLVTVSA
11C10   -WDFTY            WGQGTLVTVSA
1E10    NWDVGY            WGQGTTLTVSS
30F11   NWDVAY            WGQGTLVTVSA
5B12    NWDVGF            WGQGTTLTVSS
6H4     NWDVTC            WGQGTLVTVSA
9C9     NWDVGY            WGQGTTLTVSS
11B10   NWDVGY            WGQGTTLTVSS
33D2    NWDVTC            WGQGTLVTVSA
20A9    NWDVGY            WGQGTTLTVSS
22E9    NWDVGY            WGQGTTLTVSS
29D5    NWDVGY            WGQGTTLTVSS
21A10   NWDRGY            WGQGTTLTVSS
2G12    RWDEAY            WGQGTLVTVSA
15G2    NWDLDY            WGQGTTLTVSS
18E1    NWDLDY            WGQGTTLTVSS
2C6     NWDLNY            WGQGTTLTVSS
conH    NWDVGY            WGQGTTLTVSS
            LA                LV    A

D-Q52   NWD

J2         YFDY           WGQGTTLTVSS

J3         WFAY           WGQGTLVTVSA

49A10   PHYRNWYFDV        WGTGTTVIVSS
34E4    NWDLDY            WGQGTTLSVSS
8E9     NWDLDY            WGRGTTLTVSS
1D6     NWDLDY            WGQGTTLTVSS

34F9    SPPYYYDSTYWSFDV   WGTGTAVTVSS
7D7     SPPYYYANTYWSFDV   WGTGTTVTVSS

33B12   NWDLGY            WGQGTTITVSS
17G8    NWDLDY            WGQGTILTVSS
20A4    NWDLDY            WGQGTILTVSS
20H7    NWDLDY            WGQGTILTVSS
3C4     NWDLDY            WGQGTTLTVSS

3D7     EGLHYFGLYAMDY     WGHGTSVTVSS

39G2    GMITAPTVY         WGQGTLVTVSA
35F12   GMITAPSVY         WGQGTLVTVSA

14A3    HEGDRYYGWYFDV     WGAGTTVTVSS
12C11   HEGDTYYGWYFDV     WGAGTTVTVSS

10H11   WPFSYGMDY         WGQGTSVTVSS
19E9    WPFSYAMDY         WGQGTSVTVSS
10G8    WPFSYGMDY         WGQGTSVTVSS

16F7    QGGYEGYVDV        WGIGTTVTVSS
```

Figure 1C

```
                         ------CDRL1------
7G10   DIVMTQSPATLSVTPGDRVSLSC  RASQ------SISDYLH
6H12   DIVMTQSPATLSVTPGDRVSLSC  RASQ------SISDYLH
33B12  DIVLTQSPATLSVTPGDRVSLSC  RASQ------SISDYLH
13F11  DIVMTQSPATLSVTPGDRVSLSC  RASQ------TISDYLH
13B5   DIVMTQSPATLSVTPGDRVSLSC  RASQ------SISDYLH
13G1   DIVMTQSPATLSVTPGDRVSLSC  RASQ------SISDYLH
11C10  DIVMTQSPATLSVTPGDRVSLSC  RASQ------RISDYLY
7E2    DIVMTQSPATLSVTPGDRVSLSC  RASQ------SISDYLH
30F11  DIVMTQSPATLSVTPGDRVSLSC  RASQ------SISDYLH
34E4   DIVMTQSPATLSVTPGDRVSLSC  RASQ------SIRDYLY
6H4    DIVMTQSPATLSVTPGDRVSLSC  RASQ------SISDYLH
33D2   DIVMTQSPATLSVTPGDRVSLSC  RASQ------SISDYLH
2C6    DIVMTQSPATLSVTPGDRVSLSC  RASQ------SISDYLY
2G12   DIVMTQSPATLSVTPGDRVSLSC  RASQ------SISAYLH
1D6    DIVMTQSPATLSVTPGDRVSLSC  RASQ------SISDYLH
18E1   DIVMTQSPATLSVTPGDRVSLSC  RASQ------SISHYLY
15G2   DIVMTQSPATLSVTPGDRVSLSC  RASQ------SISDYLH
17G8   DIMMTQSPATLSVTPGDRVSLSC  RASQ------SISDYLH
20A4   DIVMTQSPATLSVTPGDRVSLSC  RASQ------SISDFLH
20H7   DIMMTQSPATLSVTPGDRVSLSC  RASQ------SISDYLH
3C4    DIVMTQSPATLSVTPGDRVSLSC  RASQ------SISDYLH
8E9    DIVMTQSPATLSVTPGDRVSLSC  RASQ------SIGDYLH
conLA  DIVMTQSPATLSVTPGDRVSLSC  RASQ------SISDYLH m5-39  DIVMTQSPATLSVTPGDRVSLSC  RASQ------SISDYLH 1E10   DIVMSQSPSSLAVSVGEKITMTC  KSSQTLLYSSNQKNFLA
20A9   DIVMSQSPSSVAVSVGEKVTMSC  KSSQSLLYSSNQKNFLA
22E9   DIVMSQSPSSVAVSVGEKVTMSC  KSSQSLLYSSNQKNFLA
29D5   DIVMSQSPSSQTVSVGERVTMSC  KSSQSLLYSSNQKNFLA
5B12   DIVMSQSPSSLAVSVGEKVTMNC  KSSQSLLYSTNQKNFLA
9C9    DIVMSQSPSSLPVSVGEKVTMSC  KSSQSLLYSSSQKNYLA
11B10  DIVMSQSPSSVAVSVGEKVTMNC  KSSQNLLYSSNQKNFLA
conLB  DIVMSQSPSSLAVSVGEKVTMSC  KSSQSLLYSSNQKNFLA
                V m8-30  DIVMSQSPSSLAVSVGEKVTMSC  KSSQSLLYSSNQKNYLA

16F7   DIVMTQSHRFMSTSVGDRVSITC  KASQ------DVSSAVA

3D7    DIQMTQTTSSLSASLGDRVTISC  SASQGISN------YLN

21A10  DIQMTQSPASLSASVGETVTITC  RASGNIHN------YLT

14A3   DIVLTQSPASLAVSLGQRATISC  KASQSVDY--DGESYMN
12C11  DIVLTQSPASLAVSLGQRATISC  KASHSVDY--DVDSFMN

10G8   DIVLTQSPASFAVALGQRATISC  RASKSVST--SDYSYMH
19E9   DIVLTQSPTSLAVSLGQRATISC  RASKSVST--SDYSYMH
10H11  DIVLTQSPASLAVALGQRATISC  RASKSVST--SDYSYMH
39G2   DIVLTQSPASLAVSLGQRATISC  RASKSVST--SAYSYFH
35F12  DIVLTQSPASLAVSLGQRATISC  RASKSVST--SAYSYFH
49A10  DIVLTQSPASLVVSLGQRATISC  RASKSVST--SGYSFLN
34F9   DIGLTQSPASLAVSLGQRATISC  RASKSVSA--FGYNYMH
7D7    DIGLTQSPASLAVSLGQRATISC  RASKSVST--SGYSFMH
conLC  DIVLTQSPASLAVSLGQRATISC  RASKSVST--SDYSYMH
                                              G
m3-12  DIVLTQSPASLAVSLGQRATISC  RASKSVST--SGYSYMH
```

Figure 2A

```
                     -CDRL2-
7G10    WYRQKSHESPRLLIK  YASQSIS  GIPSRFSGSGSGS
6H12    WYQQKSHESPRLLIK  YTSQSIS  GIPSRFSGSGSGS
33B12   WFQQRSHESPRLLIK  YASQSIS  GIPSRFSGSGSGS
13F11   WYQQKSHESPRLLIK  YASQSIS  GIPSRFSGSGSGS
13B5    WYQQKSHESPRLLIK  YASQSIS  GIPSRFSGSGSGS
13G1    WYQQKSHESPRLLIK  FASQSIS  GIPSRFSGSGSGS
11C10   WYQQKSHESPRLLIK  YASQSIS  GIPSRFSGSGSGS
7E2     WYQQKSHESPRLLIK  YASQSIS  GIPSRFSGSGSGS
30F11   WYQQKSHESPRLLIK  YASQSIS  GIPTRFSGSGSGS
34E4    WYQQKSHESPRLLIK  FASQSIS  GIPSRFSGSGSGS
6H4     WYHQKSHESPRLLIK  YASQSIS  GIPSRFSGSGSGS
33D2    WYQQKSHESPRLLIK  YASQSIS  GIPSRFSGSGSGS
2C6     WYQQKSHESPRLLIK  YASQSIS  GIPSRFSGSGSGS
2G12    WYQQKSHESPRLLIK  YASQSIS  GIPSRFSGSGSGS
1D6     WYQQKSHESPRLLIK  YASQSIS  GIPSRFSGSGSGS
18E1    WYQQKSHESPRLLIK  YASQSIS  GIPSRFSGSGSGS
15G2    WYQQKSHESPRLLIK  YASQSIS  GIPSRFSGSGSGS
17G8    WYRQKSHESPRLLIK  YASQSIS  GIPSRFSGSGSGS
20A4    WYRQKSHESPRLLIK  YVSQSIS  GIPSRFSGSGSGS
20H7    WYRQKSHESPRLLIK  YASQSIS  GIPSRFSGSGSGS
3C4     WYQQKSHESPRLLIK  YASQSIS  GIPSRFSGSGSGS
8E9     WYQQKLHESPRLLIK  YASRSIS  GIPSRFSGSGSGS
conLA   WYQQKSHESPRLLIK  YASQSIS  GIPSRFSGSGSGS m5-39   WYQQKSHESPRLLIK  YASQSIS  GIPSRFSGSGSGS 1E10    WYRQKPGQSPKLLIY  WTSTRES  GVPDRFTGSGSGT
20A9    WYQQKPGQSPKLLIF  WTSTRKS  GVPDRFTGSGSGT
22E9    WYQQKPGQSPKLLIY  WASTRES  GVPDRFTGSGSGT
29D5    WYQQKPGQSPKLLIH  WASTRES  GVPDRFTGSGSGT
5B12    WYQQKPGQSPKLLIY  WASTRKS  GVPDRFTGSGSGT
9C9     WSQQKPGQSPKLLIY  WASTRKS  GVPDRFTGSGSGT
11B10   WYQQKPGQSPKLLIY  WASTRKS  GVPDRFTGSGSGT
conLB   WYQQKPGQSPKLLIY  WASTRKS  GVPDRFTGSGSGT
                                 E
m8-30   WYQQKPGQSPKLLIY  WASTRES  GVPDRFTGSGSGT

16F7    WYQQKPGQSPNLLIY  SASFRNT  GVPDRFTGSGSGT

3D7     WFQQKPDGTVKLLIY  YTSSLHS  GVPSRFSGSGSGT

21A10   WYQQKQGKSPQLLVY  NAKTLAD  GVPSRFSGSGSGT

14A3    WYQQKPGQPPKLLIY  TSSSLAS  GIPARFSGSGSGT
12C11   WYQQKPGQPPKLLIF  ASSSLES  GIPARFSGSGSGT

10G8    WYQQKPGQPPKLLIY  LASNLDS  GVPARFSGSGSGT
19E9    WYQQKPGQPPKLLIY  LASNLES  GVPARFSGSGSGT
10H11   WYQQKPGQPPKLLIY  LASNLDS  GVPARFSGSGSGT
39G2    WYQQKPGQPPKLLIY  LASNLES  GVPARFSGSGSGT
35F12   WYQQKPGQPPKLLIY  LASNLES  GVPARFSGSGSGT
49A10   WYQQKPGQPPKLLIY  LASNLES  GVPARFSGSGSGT
34F9    WYQQKPGQPPKLLIY  LASNLES  GVPARFSGSGSGT
7D7     WYQQKPGQPPKLLIY  LASNLES  GVPARFSGSGSGT
conLC   WYQQKPGQPPKLLIY  LASNLES  GVPARFSGSGSGT m3-12   WYQQKPGQPPKLLIY  LASNLES  GVPARFSGSGSGT
```

Figure 2B

```
                      --CDRL3--
7G10   DFTLSINSVEPEDVGVYYC   QNGHSFPFT   FGSGTKLEIKR
6H12   DFTLSINSVEPEDVGVYYC   QNGHSFPFT   FGSGTKLEIKR
33B12  DFTLSINSVEPEDVGVYYC   QNGHSFPFT   FGSGTKLEIKR
13F11  HFTLSINSVEPEDVGVYYC   QNGHSFPFT   FGSGTKLEIKR
13B5   DFTLSINSVEPEDVGVYYC   QNGHSFPFT   FGSGTKLEIKR
13G1   DFTLSINSVEPEDVGVYYC   QNGHSFPYT   FGGGTKLEIKR
11C10  DFTLSINSVEPEDVGVYYC   QNGHSFPYT   FGGGTKLEIKR
7E2    EFTLSINSVEPEDVGVYYC   QNGHSFPFT   FGSGTKLEIKR
30F11  DFTLTINSVEPEDVGVYYC   QNGHSFPFT   FGSGTKLEIKR
34E4   DFTLSINSVEPEDVGVYYC   QNGHSFPYT   FGGGTKLEIKR
6H4    DFTLTINSVEPEDVGVYYC   QNGHSFPFT   FGSGTKLEIKR
33D2   DFTLSINSVEPEDVGVYYC   QNGHSFPFT   FGSGTKLEIKR
2C6    DFTLSINSVEPEDVGVYFC   QNGHSFPFT   FGSGTKLEIKR
2G12   DFTLSINSVEPEDVGIYYC   QNGHSFPFT   FGSGTKLEIKR
1D6    DFTLSITNVEPEDVGIYYC   QNGHSFPFT   FGSGTKLEIKR
18E1   DFTLSINSVEPEDVGMYYC   QNGHSFPYT   FGGGTKLEIKR
15G2   DFILNINSVEPEDVGVYYC   QNGHSFPYT   FGGGTKLEIKR
17G8   DFTLSINSVEPEDVGIYYC   QNGHSFPYT   FGGGTKLEIKR
20A4   DFTLSINSVDPEDVGVYYC   QNGHSFPYT   FGGGTKLEIKR
20H7   DFTLSINSVEPEDVGVYFC   QNGHSFPYT   FGGGTKLEIKR
3C4    DFTLSINSVESEDVGVYYC   QNGHSFPFT   FGSGTKLKIKR
8E9    YFTLSINSVEAEDVGVYFC   QNGHSFPFT   FGSGTKLEIKR
conLA  DFTLSINSVEPEDVGVYYC   QNGHSFPFT m5-39  DFTLSINSVEPEDVGVYYC   QNGHSFP 1E10   DFTLTISSVKAEDLAVYYC   QQYYSYPFT   FGSGTKLEIKR
20A9   DFTLTISSVKAEDLAVYYC   QQYYSYPFT   FGSGTKLEIKR
22E9   DFILTISSVRAEDLAFYYC   QQYYSYPFT   FGSGTKLEIKR
29D5   DFTLTISSVKAEDLALYYC   QQYYSYPFT   FGSGTKLEIKR
5B12   DFTLTISSVKAEDLAVYYC   QQYYSYPFT   FGSGTKLEIKR
9C9    DFTLTISSVKAEDLAVYYC   HQYYSYPFT   FGSGTKLEIKR
11B10  DFTLTISSVRAEDLAFYYC   QQYYSYPFT   FGSGTKLEIKR
conLB  DFTLTISSVKAEDLAVYYC   QQYYSYPFT m8-30  DFTLTISSVKAEDLAVYYC   QQYYSYP

16F7   DFTFTISGVQAEDLAVYYC   QQHHSTPLT   FGAGTKLELKR

3D7    DYSLTISNLEPEDIATYYC   QQYSKLPYT   FGGGTKLEIKR

21A10  QFSLKINSLQPEDFGSYYC   QHFWSTPFT   FGSGTKLEIKR

14A3   NFTLNIHPVEEEDAATYCC   QQGNEDLFT   FGSGTKLEIKR
12C11  NFILNIHPVEEEDAATYYC   QQGNEDLFT   FGSGTKLEIKR

10G8   DFTLNIHPVEEEDAATYYC   QHSRELPYT   FGGGTKLEIKR
19E9   DFTLNIHPVEEEDAATYYC   QHSRELPYT   FGGGTKLEIRR
10H11  DFTLNIHPVEEEDAATYYC   QHSREFPYT   FGGGTKLEIKR
39G2   DFTLNIHPVEEEDAATYYC   QHSRELPWT   FGGGTKLEITP
35F12  DFTLNIHPVEEGDAATYYC   QHSRELPWT   FGGGTKLEITR
49A10  DFTLNIHPVEAEDATTYYC   QHSRELPLT   FGSGTKLEMKR
34F9   DFTLNIHAVEEEDAATYYC   QHSRELPLT   FGAGTKLELKR
7D7    DFILNIHPVEEEDAATYYC   QHSRELPLA   FGAGTKLELTP
conLC  DFTLNIHPVEEEDAATYYC   QHSRELPYT m3-12  DFTLNIHPVEEEDAATYYC   QHSRELP
```

Figure 2C

ENGINEERED ANTI-IL-23P19 ANTIBODIES

This application is a Continuation of U.S. patent application Ser. No. 12/527,456, filed Jan. 5, 2010, which is a 371 of PCT Patent Application No. PCT/US08/02394, filed Feb. 21, 2008, which claims benefit of U.S. Provisional Patent Application No. 60/891,413 filed Feb. 23, 2007, each of which is hereby incorporated by reference in its entirety herein.

The Sequence Listing filed electronically herewith is also hereby incorporated by reference in its entirety (File Name: BP06606-US-CNT_SeqListing.txt; Date Created: Jun. 22, 2012; File Size: 143 KB.)

FIELD OF THE INVENTION

The present invention relates generally to interleukin-23 p19 (IL-23p19)-specific antibodies and uses thereof. More specifically, the invention relates to humanized antibodies that recognize human IL-23p19 and modulate its activity, particularly in inflammatory, autoimmune and proliferative disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Interleukin-12 (IL-12) is a heterodimeric molecule composed of p35 and p40 subunits. Studies have indicated that IL-12 plays a critical role in the differentiation of naïve T cells into T-helper type 1 CD4$^+$ lymphocytes that secrete IFNγ. It has also been shown that IL-12 is essential for T cell dependent immune and inflammatory responses in vivo. See, e.g., Cua et al. (2003) *Nature* 421:744-748. The IL-12 receptor is composed of IL-12β1 and IL-12β2 subunits.

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12β1, which is shared by the IL-12 receptor. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23 (see, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948).

Recent studies, through the use of p40 KO mice, have shown that blockade of both IL-23 and IL-12 is an effective treatment for various inflammatory and autoimmune disorders. However, the blockade of IL-12 through p40 appears to have various systemic consequences such as increased susceptibility to opportunistic microbial infections. Bowman et al. (2006) *Curr. Opin. Infect. Dis.* 19:245.

Therapeutic antibodies may be used to block cytokine activity. The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al. (1986) *Nature* 321:522; Verhoeyen et al. (1988) *Science* 239:1534. However, CDR loop exchanges still do not uniformly result in an antibody with the same binding properties as the antibody of origin. Changes in framework residues (FR), residues involved in CDR loop support, in humanized antibodies also are required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology (NY)* 9:421-5. Moreover, most prior studies used different human sequences for animal light and heavy variable sequences, rendering the predictive nature of such studies questionable. Sequences of known antibodies have been used or, more typically, those of antibodies having known X-ray structures, antibodies NEW and KOL. See, e.g., Jones et al., supra; Verhoeyen et al., supra; and Gorman et al., supra. Exact sequence information has been reported for a few humanized constructs. Exemplary engineered antibodies to IL-23p19 are disclosed in commonly-assigned U.S. Provisional Patent Application Nos. 60/891,409 and 60/891,413 (both filed 23 Feb. 2007), in U.S. Patent Application Publication Nos. 2007/0009526 and 2007/0048315, and in International Patent Publication Nos. WO 2007/076524, WO 2007/024846 and WO 2007/147019.

The need exists for anti-huIL-23p19 antibodies for use, e.g., in treatment of inflammatory, autoimmune, and proliferative disorders. Preferably, such antibodies are engineered to introduce human germline sequences to reduce immunogenicity in human subjects, e.g. in the framework regions. Preferably, such antibodies will have high affinity for huIL-23p19 and will bind with high specificity to huIL-23p19.

SUMMARY OF THE INVENTION

The present invention provides binding compounds, such as antibodies or fragments thereof, including humanized or chimeric recombinant antibodies, that bind human IL-23p19, comprising at least one antibody light chain variable region, or antigen binding fragment thereof, having at least one, two or three CDRs selected from the group consisting of SEQ ID NOs: 80-88. In one embodiment, the binding compound of the present invention comprises a light chain variable domain comprising at least one CDRL1 selected from the group consisting of SEQ ID NOs: 80-82; at least one CDRL2 selected from the group consisting of SEQ ID NOs: 83-85; and at least one CDRL3 selected from the group consisting of SEQ ID NOs: 86-88.

In one embodiment, the binding compound comprises at least one antibody heavy chain variable region, or antigen binding fragment thereof, having at least one, two or three CDRs selected from the group consisting of SEQ ID NOs: 77-79.

In some embodiments, the binding compound comprises a framework region, wherein the amino acid sequence of the framework region is all or substantially all of a human immunoglobulin amino acid sequence.

In another embodiment, the binding compound of the present invention comprises at least one, two or three light chain CDRs having the sequence of SEQ ID NOs: 80-88 or optionally a variant thereof. In one embodiment, the binding compound comprises at least one, two or three heavy chain CDRs having the sequence of SEQ ID NOs: 77-79 or optionally a variant thereof. In various embodiments the variant comprises up to 1, 2, 3, 4, 5, 6, 7, 8, 9, 10 or more conservatively modified amino acid residues relative to the sequence of the respective SEQ ID NOs. Conservative amino acid substitutions are provided at Table 1.

In other embodiments, the binding compound comprises at least one antibody light chain variable region, or antigen binding fragment thereof, having at least one, two or three CDRs selected from the group consisting of SEQ ID NOs: 68-76. In one embodiment, the binding compound of the present invention comprises a light chain variable domain comprising at least one CDRL1 selected from the group consisting of SEQ ID NOs: 68-70, at least one CDRL2 selected from the group consisting of SEQ ID NOs: 71-73 and at least one CDRL3 selected from the group consisting of SEQ ID NOs: 74-76. In one embodiment, the binding compound comprises at least one antibody heavy chain variable region, or antigen binding fragment thereof, having at least one, two or three CDRs selected from the group consisting of SEQ ID NOs: 65-67.

In other embodiments, the binding compound of the present invention comprises at least one, two or three light chain CDRs having the sequence of SEQ ID NOs: 68-76 or a variant thereof. In another embodiment, the binding compound of the present invention comprises a light chain variable domain comprising at least one CDRL1 selected from the group consisting of SEQ ID NOs: 68-70 or a variant thereof, and at least one CDRL2 selected from the group consisting of SEQ ID NOs: 71-73 or a variant thereof, and at least one CDRL3 selected from the group consisting of SEQ ID NOs: 74-76 or a variant thereof. In one embodiment, the binding compound of the present invention comprises at least one, two or three heavy chain CDRs having the sequence of SEQ ID NOs: 65-67 or a variant thereof. In various embodiments the variant comprises up to 1, 2, 3, 4, 5, 6, 7, 8, 9, 10 or more conservatively modified amino acid residues relative to the sequence of the respective SEQ ID NOs.

In yet another embodiment, the binding compound of the present invention comprises at least one, two or three light chain CDRs selected from the group consisting of residues 43-53, 69-75 and 108-116 of SEQ ID NOs: 2 and 4, and at least one, two or three heavy chain CDRs selected from the group consisting of residues 45-54, 69-85 and 118-123 of SEQ ID NOs: 1 and 3.

In one embodiment, the binding compound comprises an antibody light chain variable domain having the sequence of the residues 20-129 of SEQ ID NO: 2 or 4 or a variant thereof. In one embodiment, the binding compound comprises an antibody heavy chain variable domain having the sequence of residues 20-134 of SEQ ID NO: 1 or 3 or a variant thereof. In various embodiments the variant comprises up to 1, 2, 3, 4, 5, 6, 7, 8, 9, 10, 15, 20, 30, 40 or 50 or more conservatively modified amino acid residues relative to the sequence of the respective SEQ ID NOs.

In one embodiment, the binding compound comprises an antibody light chain comprising, or consisting essentially of, the sequence of the mature form (residues 20-233) of SEQ ID NO: 2 or 4. In one embodiment, the binding compound comprises an antibody heavy chain comprising, or consisting essentially of, the sequence of the mature form (residues 20-464) of SEQ ID NO: 1 or 3.

In one embodiment, the binding compound of the present invention binds to human IL-23p19 (SEQ ID NO: 29) at an epitope comprising residues 82-95, or residues 133-140, or both. In another embodiment the IL-23p19 binding compound binds to an epitope comprising some or all of residues E82, G86, S87, D88, T91, G92, E93, P94, S95, H106, P133, S134, Q135, P136, W137, R139 and L140, and optionally residues K83, F90 and L110. In various embodiments the epitope for an antibody of interest is determined by obtaining an X-ray crystal structure of an antibody:antigen complex and determining which residues on IL-23p19 are within a specified distance of residues on the antibody of interest, wherein the specified distance is, e.g., 4 Å or 5 Å. In some embodiments, the epitope is defined as a stretch of 8 or more contiguous amino acid residues along the IL-23p19 sequence in which at least 50%, 70% or 85% of the residues are within the specified distance of the antibody.

In other embodiments, the present invention provides a binding compound that binds to human IL-23 and has a light chain variable domain ($V_L$) with at least 50%, 75%, 80%, 85%, 90% or 95% sequence homology with the residues 20-129 of SEQ ID NO: 2 or 4. In one embodiment, the present invention provides a binding compound that binds to human IL-23 and has a heavy chain variable domain ($V_H$) with at least 50%, 75%, 80%, 85%, 90% or 95% sequence homology with residues 20-134 of SEQ ID NO: 1 or 3.

In one embodiment, the binding compound comprises, or consists essentially of, an antibody having a light chain having the sequence of the mature form (i.e. residues 20-233) of SEQ ID NO: 2 or 4. In one embodiment, the binding compound comprises, or consists essentially of, an antibody having a heavy chain having the sequence of the mature form (i.e. residues 20-464) of SEQ ID NO: 1 or 3.

In another embodiment, the binding compound of the present invention comprises an antibody light chain variable domain comprising CDRs having the sequence of residues 24-34, 50-56 and 89-97 of SEQ ID NO: 112, or a variant thereof. In another embodiment, the binding compound comprises CDRL1 having the sequence of residues 24-34 of SEQ ID NO: 112 or a variant thereof CDRL2 having the sequence of residues 50-56 of SEQ ID NO: 112 or a variant thereof and CDRL3 having the sequence of residues 89-97 of SEQ ID NO: 112 or a variant thereof.

In one embodiment, the binding compound comprises an antibody heavy chain variable domain comprising three CDRs selected from the group consisting of residues 26-35, 50-66 and 99-104 of SEQ ID NO: 99 and residues 50-66 of SEQ ID NOs: 129 and 130, or a variant thereof. In another embodiment, the binding compound comprises CDRH1 having the sequence of residues 26-35 of SEQ ID NO: 99 or a variant thereof CDRH2 having the sequence of residues 50-66 of one of SEQ ID NOs: 99, 129 or 130 or a variant thereof and CDRH3 having the sequence of residues 99-104 of SEQ ID NO: 99 or a variant thereof.

In various embodiments the variant comprises up to 1, 2, 3, 4, 5, 6, 7, 8, 9, 10 or more conservatively modified amino acid residues relative to the sequence of the respective SEQ ID NOs. Conservative amino acid substitutions are provided at Table 1.

In one embodiment, the binding compound comprises an antibody light chain variable domain having the sequence of SEQ ID NO: 131 or a variant thereof. In one embodiment, the binding compound comprises an antibody heavy chain variable domain having the sequence of SEQ ID NO: 129, 130, 132 or 133 or a variant thereof. In various embodiments the variant comprises up to 1, 2, 3, 4, 5, 6, 7, 8, 9, 10, 15, 20, 30, 40 or 50 or more conservatively modified amino acid residues relative to the sequence of the respective SEQ ID NOs.

In one embodiment, the binding compound comprises an antibody light chain comprising, or consisting essentially of, the sequence of SEQ ID NO: 131. In one embodiment, the binding compound comprises an antibody heavy chain comprising, or consisting essentially of, the sequence of SEQ ID NO: 129, 130, 132 or 133. In one embodiment the binding compound of the present invention binds to human IL-23p19 (SEQ ID NO: 29) at an epitope comprising residues 82-95, or residues 133-140, or both. In another embodiment the IL-23p19 binding compound binds to an epitope comprising some or all of residues E82, G86, S87, D88, T91, G92, E93, P94, S95, H106, P133, S134, Q135, P136, W137, R139 and L140, and optionally residues K83, F90 and L110.

In other embodiments, the present invention provides a binding compound that binds to human IL-23 and has a light chain variable domain ($V_L$) with at least 50%, 75%, 80%, 85%, 90% or 95% sequence homology with SEQ ID NO: 131. In one embodiment, the present invention provides a binding compound that binds to human IL-23 and has a heavy chain variable domain ($V_H$) with at least 50%, 75%, 80%, 85%, 90% or 95% sequence homology with SEQ ID NO: 129, 130, 132 or 133. In one embodiment the binding compound comprises the light chain variable domain of SEQ ID NO: 131 and the heavy chain variable domain of SEQ ID NO: 132.

In one embodiment, the invention relates to antibodies that are able to block the binding of a binding compound of the present invention to human IL-23 in a cross-blocking assay. In another embodiment, the invention relates to binding compounds that are able to block IL-23-mediated activity, such activities including but not limited to, binding to its receptor and promoting the proliferation or survival of $T_H17$ cells.

In some embodiments, the binding compound of the present invention further comprises a heavy chain constant region, wherein the heavy chain constant region comprises a γ1, γ2, γ3, or γ4 human heavy chain constant region or a variant thereof. In various embodiments the light chain constant region comprises a lambda or a kappa human light chain constant region.

In various embodiments the binding compounds of the present invention are polyclonal, monoclonal, chimeric, humanized or fully human antibodies or fragments thereof. The present invention also contemplates that the antigen binding fragment is an antibody fragment selected from the group consisting of, e.g., Fab, Fab', Fab'-SH, Fv, scFv, F(ab')$_2$, and a diabody.

The present invention encompasses a method of suppressing an immune response in a human subject comprising administering to a subject in need thereof an antibody (or a antigen binding fragment thereof) specific for IL-23 in an amount effective to block the biological activity of IL-23. In some embodiments, the antibody specific for IL-23 is the humanized or chimeric antibody. In further embodiments, the immune response is an inflammatory response including arthritis, psoriasis, and inflammatory bowel disease. In other embodiments, the immune response is an autoimmune response, including multiple sclerosis, uveitis, systemic lupus erythematosus and diabetes. In another embodiment, the subject has cancer and the immune response is a Th17 response.

The present invention also contemplates administering an additional immunosuppressive or anti-inflammatory agent. The binding compounds of the present invention can be in a pharmaceutical composition comprising the binding compound, or antigen binding fragment thereof, in combination with a pharmaceutically acceptable carrier or diluent. In a further embodiment, the pharmaceutical composition further comprises an immunosuppressive or anti-inflammatory agent.

The present invention encompasses an isolated nucleic acid encoding the polypeptide sequence of an antibody embodiment of the binding compound of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

In various embodiments, the invention relates to use of a binding compound of the present invention in the manufacture of medicaments for the treatment of disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

In other embodiments the invention relates to pharmaceutical compositions comprising a binding compound of the present invention for treating disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

In some embodiments, the binding compound or pharmaceutical composition of the present invention induces a prolonged period of remission from disease symptoms in a subject, such that the dosing interval can be extended to much longer than the half-life of the binding compound in the subject, for example in the treatment of a relapsing-remitting disease. In various embodiments, the interval between one administration and another is 6-, 8-, 10-, 12-, 16-, 20-, 24-, 30-weeks or longer. In other embodiments a single administration is sufficient to permanently prevent relapses.

BRIEF DESCRIPTION OF THE DRAWINGS

FIGS. 1A-1C show comparisons of mouse anti-human IL-23p19 antibody clone heavy chain variable domain sequences. Sequences are provided for clones 7G10, 6H12, 13F11, 13B5, 7E2, 13G1, 11C10, 1E10, 30F11, 5B12, 6H4, 9C9, 11B10, 33D2, 20A9, 22E9, 29D5, 21A10, 2G12, 15G2, 18E1, 2C6, 49A10, 34E4, 8E9, 1D6, 34F9, 7D7, 33B12, 17G8, 20A4, 20H7, 3C4, 3D7, 39G2, 35F12, 14A3, 12C11, 10H11, 19E9, 10G8 and 16F7. CDRs are indicated. Also provided is a consensus sequence for a subset of the clones (conH), and mouse germline sequences muIGHV1-14 ("V1-14"), muIGHD-Q52 ("D-Q52"), muIGHJ2 ("J2") and muIGHJ3 ("J3"). Cross references to sequence identifiers in the Sequence Listing are provided at Table 8.

FIGS. 2A-2C show comparisons of mouse anti-human IL-23p19 antibody clone light chain variable domain sequences. Sequence are provided for clones 7G10, 6H12, 33B12, 13F11, 13B5, 13G1, 11C10, 7E2, 30F11, 34E4, 6H4, 33D2, 2C6, 2G12, 1D6, 18E1, 15G2, 17G8, 20A4, 20H7, 1E10, 20A9, 22E9, 29D5, 5B12, 9C9, 11B10, 16F7, 3D7, 21A10, 14A3, 12C11, 10G8, 19E9, 10H11, 39G2, 35F12, 49A10, 34F9, 8E9, 3C4 and 7D7. CDRs are indicated. Also provided are consensus sequences for each of three subfamilies of light chain CDR sequences (conLA, conLB, conLC), as well as mouse germline sequences IGKV5-39 ("m5-39"), IGKV8-30 ("m8-30") and IGVK3-12 ("m3-12"). Cross references to sequence identifiers in the Sequence Listing are provided at Table 8.

DETAILED DESCRIPTION

As used herein, including the appended claims, the singular forms of words such as "a," "an," and "the," include their corresponding plural references unless the context clearly dictates otherwise. Table 8 below provides a listing of sequence identifiers used in this application. All references cited herein are incorporated by reference to the same extent as if each individual publication, patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts IL-23 receptor (IL-23R/IL-12Rbeta1 heterodimer), e.g., in the fluid phase or colloidal phase, but also situations where the agonist or antagonist does not contact the cell or the receptor.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "IL-23p19 binding fragment," "binding fragment thereof" or "antigen binding fragment thereof" encompass a fragment or a derivative of an antibody that still substantially retains its biological activity of inhibiting IL-23p19 activity. Therefore, the term "antibody fragment" or IL-23p19 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its IL-23p19 inhibitory activity. Preferably, a binding fragment or derivative retains at least 25%, 50%, 60%, 70%, 80%, 90%, 95%, 99% or 100% (or more) of its IL-23p19 inhibitory activity, although any binding fragment with sufficient affinity to exert the desired biological effect will be useful. It is also intended that a IL-23p19 binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies (e.g. hum6H12) from parental rodent antibodies (e.g. mouse 6H12, or "m6H12"). The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. See Tables 2 and 3, in which sequence numbering is with reference to the Sequence Listing.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. When used with reference to antibodies, the term "binding compound" refers to both antibodies and antigen binding fragments thereof. "Binding" refers to an association of the binding composition with a target where the association results in reduction in the normal Brownian motion of the binding composition, in cases where the binding composition can be dissolved or suspended in solution. "Binding composition" refers to a molecule, e.g. a binding compound, in combination with a stabilizer, excipient, salt, buffer, solvent, or additive, capable of binding to a target.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888, 530 issued to Netti et al. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Exogenous" refers to substances that are produced outside an organism, cell, or human body, depending on the context. "Endogenous" refers to substances that are produced within a cell, organism, or human body, depending on the context.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

An "IL-17-producing cell" means a T cell that is not a classical TH1-type T cell or classical TH2-type T cell, referred to as $T_H17$ cells. $T_H17$ cells are discussed in greater detail at Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222. "IL-17-producing cell" also means a T cell that expresses a gene or polypeptide of Table 10B of U.S. Patent Application Publication No. 2004/0219150 (e.g., mitogen responsive P-protein; chemokine ligand 2; interleukin-17 (IL-17); transcription factor RAR related; and/or suppressor of cytokine signaling 3), where expression with treatment by an IL-23 agonist is greater than treatment with an IL-12 agonist, where "greater than" is defined as follows. Expression with an IL-23 agonist is ordinarily at least 5-fold greater, typically at least 10-fold greater, more typically at least 15-fold greater, most typically at least 20-fold greater, preferably at least 25-fold greater, and most preferably at least 30-fold greater, than with IL-12 treatment. Expression can be measured, e.g., with treatment of a population of substantially pure IL-17 producing cells. A Th17 response is an immune response in which the activity and/or proliferation of Th17 cells are enhanced, typically coupled with a repressed Th1 response.

Moreover, "IL-17-producing cell" includes a progenitor or precursor cell that is committed, in a pathway of cell development or cell differentiation, to differentiating into an IL-17-producing cell, as defined above. A progenitor or precursor cell to the IL-17 producing cell can be found in a draining lymph node (DLN). Additionally, "IL-17-producing cell" encompasses an IL-17-producing cell, as defined above, that has been, e.g., activated, e.g., by a phorbol ester, ionophore, and/or carcinogen, further differentiated, stored, frozen, desiccated, inactivated, partially degraded, e.g., by apoptosis, proteolysis, or lipid oxidation, or modified, e.g., by recombinant technology.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

"Inhibitors" and "antagonists" or "activators" and "agonists" refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) Ann. Clin. Lab. Sci. 30:145-158; Hood and Cheresh (2002) Nature Rev. Cancer 2:91-100; Timme et al. (2003) Curr. Drug Targets 4:251-261; Robbins and Itzkowitz (2002) Med. Clin. North Am. 86:1467-1495; Grady and Markowitz (2002) Annu. Rev. Genomics Hum. Genet. 3:101-128; Bauer, et al. (2001) Glia 36:235-243; Stanimirovic and Satoh (2000) Brain Pathol. 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) Biochem. Biophys. Res. Commun. 307:198-205; Muyldermans (2001) J. Biotechnol. 74:277-302; Li (2000) Nat. Biotechnol. 18:1251-1256; Apostolopoulos et al. (2002) Curr. Med. Chem. 9:411-420; Monfardini et al. (2002) Curr. Pharm. Des. 8:2185-2199; Domingues et al. (1999) Nat. Struct. Biol. 6:652-656; Sato and Sone (2003) Biochem. J. 371:603-608; U.S. Pat. No. 6,326,482.

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case IL-23p19) if it binds to polypeptides comprising the sequence of IL-23p19 but does not bind to proteins lacking the sequence of IL-23p19. For example, an antibody that specifically binds to a polypeptide comprising IL-23p19 may bind to a FLAG®-tagged form of IL-23p19 but will not bind to other FLAG®-tagged proteins.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) Analyt. Biochem. 107:220-239.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherpeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

II. General

The present invention provides engineered anti-IL-23 antibodies and uses thereof to treat inflammatory, autoimmune, and proliferative disorders. A subset of the antibodies disclosed herein are also disclosed in U.S. Patent Application Publication No. 2007/0048315, specifically clones 7G10, 6H12, 13F11, 13B5, 7E2, 13G1, 11C10, 1E10, 30F11, 5B12, 6H4, 9C9, 11B10, 33D2, 20A9, 22E9, 29D5, 21A10, 49A10, 34E4, 34F9, 7D7, 33B12, 3D7, 39G2, 35F12, 10H11, 19E9 and 10G8.

A number of cytokines have a role in the pathology or repair of neurological disorders. IL-6, IL-17, interferon-gamma (IFNgamma, IFN-γ), and granulocyte colony-stimulating factor (GM-CSF) have been associated with multiple sclerosis. Matusevicius et al. (1999) *Multiple Sclerosis* 5:101-104; Lock et al. (2002) *Nature Med.* 8:500-508. IL-1alpha, IL-1beta, and transforming growth factor-beta 1 (TGF-beta1) play a role in ALS, Parkinson's disease, and Alzheimer's disease. Hoozemans et al. (2001) *Exp. Gerontol.* 36:559-570; Griffin and Mrak (2002) *J. Leukocyte Biol.* 72:233-238; Ilzecka et al. (2002) *Cytokine* 20:239-243. TNF-alpha, IL-1beta, IL-6, IL-8, interferon-gamma, and IL-17 appear to modulate response to brain ischemia. See, e.g., Kostulas et al. (1999) *Stroke* 30:2174-2179; Li et al. (2001) *J. Neuroimmunol.* 116:5-14. Vascular endothelial cell growth factor (VEGF) is associated with ALS. Cleveland and Rothstein (2001) *Nature* 2:806-819.

Inflammatory bowel disorders, e.g., Crohn's disease, ulcerative colitis, celiac disease, and irritable bowel syndrome, are mediated by cells of the immune system and by cytokines. For example, Crohn's disease is associated with increased IL-12 and IFNγ, while ulcerative colitis is associated with increased IL-5, IL-13, and transforming growth factor-beta (TGFbeta). IL-17 expression may also increase in Crohn's disease and ulcerative colitis. See, e.g., Podolsky (2002) *New Engl. J. Med.* 347:417-429; Bouma and Strober (2003) *Nat. Rev. Immunol.* 3:521-533; Bhan et al. (1999) *Immunol. Rev.* 169:195-207; Hanauer (1996) *New Engl. J. Med.* 334:841-848; Green (2003) *The Lancet* 362:383-391; McManus (2003) *New Engl. J. Med.* 348:2573-2574; Horwitz and Fisher (2001) *New Engl. J. Med.* 344:1846-1850; Andoh et al. (2002) *Int. J. Mol. Med.* 10:631-634; Nielsen et al. (2003) *Scand. J. Gastroenterol.* 38:180-185; Fujino et al. (2003) *Gut* 52:65-70.

IL-23 receptor is a heterodimeric complex of IL-23R and IL-12Rβ1 subunits. See Parham et al. (2000) *J. Immunol.* 168:5699. IL-12 receptor is a complex of IL-12Rβ1 and IL-12Rβ2 subunits. See Presky et al. (1996) *Proc. Nat'l Acad. Sci. USA* 93:14002. IL-23R has been implicated as a critical genetic factor in the inflammatory bowel disorders Crohn's disease and ulcerative colitis. Duerr et al. (2006) *Sciencexpress* 26 Oct. 2006:1. A genome-wide association study found that the gene for IL-23R was highly associated with Crohn's disease, with an uncommon coding variant (Arg381Gln) conferring strong protection against the disease. This genetic association confirms prior biological findings (Yen et al. (2006) *J. Clin. Investigation* 116:1218) suggesting that IL-23 and its receptor are promising targets for new therapeutic approached to treating IBD.

Inflammatory diseases of the skin, joints, CNS, as well as proliferative disorders elicit similar immune responses, thus IL-23 blockade should provide inhibition of these immune mediated inflammatory disorders, without comprising the host ability to fight systemic infections. Antagonizing IL-23 should relieve the inflammation associated with inflammatory bowel disease, Crohn's disease, Ulcerative Colitis, rheumatoid arthritis, psoriatic arthritis, psoriasis, ankylosing spondylitis, and atopic dermatitis. Use of IL-23 inhibitors will also provide inhibition of proliferative disorders, e.g., cancer and autoimmune disorders, e.g., multiple sclerosis, type I diabetes, and SLE. Descriptions of IL-23 in these various disorders can be found in the following published PCT applications: WO 04/081190; WO 04/071517; WO 00/53631; and WO 01/18051. IL-23 inhibitors may also find use in treatment of infections, including chronic infections, such as bacterial, mycobacterial, viral and fungal infections.

The p19 subunit of IL-23 is a member of the 'long chain' family of hematopoietic cytokines (Oppmann et al. (2000) supra) and comprises four packed α-helices termed A, B, C and D, with an up-up-down-down topology. The 4 helices are connected by 3 polypeptide loops. The A-B and C-D loops are modeled to be relatively long as they connect parallel helices. The short B-C loop connects the antiparallel B and C helices. The p19 subunit of IL-23 is a member of the IL-6 family of helical cytokines. This family of cytokines bind to their cognate receptors through three conserved epitopes (site I, II and III; Bravo and Heath (2000) *EMBO J.* 19:2399-2411). The p19 subunit interacts with three cytokine receptor subunits to form the competent signaling complex. When expressed in a cell, the p19 subunit first form a complex with the p40 subunit, which it shares with IL-12. As noted above, the p19p40 complex is secreted from the cell as a heterodimeric protein and is called IL-23. See, e.g., Oppmann et al., supra. The cellular receptor complex required to transduce the IL-23 signal consists of two members of the tall signaling receptor subunits of the IL-6/IL-12 family of cytokines, the IL-23-specific IL-23R (see, e.g., Parham et al. supra) and the IL-12Rb1, that is shared with IL-12.

Insights into the structural basis of 'long chain' cytokine/receptor recognition have shown that although large areas of protein surface are buried in formation of cytokine—receptor complexes, the affinity of the interaction is dominated by a few, often tightly clustered amino acid residues forming an energetic 'hot spot' in the center of the binding interface. The identity of the residues that dominate the binding energy of a large protein-protein interface has been termed the 'functional epitope.' The affinity of the interaction (and hence biological specificity) is consequently defined by the structural complementarity of the functional epitopes of ligand and receptor. Detailed mutagenesis studies have shown that the most significant residues that make up the functional epitopes of cytokines and receptors are hydrophobic contacts involving either non-polar side chains such as tryptophan, the aliphatic components of non-polar side chains or the polypeptide backbone. The non-polar 'core' is surrounded by a halo of polar residues of lesser importance for binding energy. Kinetic studies indicate that the primary role of the functional epitopes is to stabilize protein-protein interaction by decreasing the dissociation rate of the complex. It has been suggested that the initial contact between cytokine and receptor is dominated by random diffusion or 'rolling' of protein surfaces producing many unstable contacts. The complex is then stabilized when the functional epitopes of the receptor and ligand engage. See, e.g., Bravo and Heath, supra.

III. Generation of IL-23 Specific Antibodies

Any suitable method for generating monoclonal antibodies may be used. For example, a recipient may be immunized with a linked or unlinked (e.g. naturally occurring) form of the IL-23 heterodimer, or a fragment thereof. Any suitable method of immunization can be used. Such methods can include adjuvants, other immunostimulants, repeated booster immunizations, and the use of one or more immunization routes.

Any suitable source of IL-23 can be used as the immunogen for the generation of the non-human antibody, specific for the p 19 subunit, of the compositions and methods disclosed herein. Such forms include, but are not limited whole protein, including linked and naturally occurring heterodimers, peptide(s), and epitopes, generated through recombinant, synthetic, chemical or enzymatic degradation means known in the art. In various embodiments the IL-23 immunogen may be, e.g., a human p19 polypeptide, a natural heterodimeric complex of human p19 and p40 (two disulfide-crosslinked polypeptide chains), a fusion protein comprising human p40 and p19 sequences (see U.S. Pat. No. 7,090,847), or chimeric IL-23 (e.g. human p19:mouse p40).

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit IL-23. It is desirable to prepare monoclonal antibodies (mAbs) from various mammalian hosts, such as mice, rodents, primates, humans, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a antigen binding fragment thereof by screening a DNA library from human B cells according, e.g., to the general protocol outlined by Huse et al. (1989) Science 246:1275-1281.

Other suitable techniques involve selection of libraries of antibodies in phage or similar vectors. See, e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156. See also Abgenix and Medarex technologies.

Antibodies or binding compositions against predetermined fragments of IL-23 can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective IL-23. These monoclonal antibodies will usually bind with at least a $K_d$ of about 1 µM, more usually at least about 300 nM, 30 nM, 10 nM, 3 nM, 1 nM, 300 µM, 100 µM, 30 µM or better, usually determined by ELISA. Suitable non-human antibodies may also be identified using the biologic assays described in Example 5, below.

IV. Humanization of IL-23 Specific Antibodies

Any suitable non-human antibody can be used as a source for the hypervariable region. Sources for non-human antibodies include, but are not limited to, murine, Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. EP438310A1) and Winter (European Patent Application Publication No. EP239400B1).

Amino acid sequence variants of humanized anti-IL-23 antibody are prepared by introducing appropriate nucleotide changes into the humanized anti-IL-23 antibody DNA, or by peptide synthesis. Such variants include, for example, deletions from, and/or insertions into, and/or substitutions of, residues within the amino acid sequences shown for the humanized anti-IL-23 antibody (e.g. as in SEQ ID NOs: 1 and 2). Any combination of deletion, insertion, and substitution is made to arrive at the final construct, provided that the final construct possesses the desired characteristics. The amino acid changes also may alter post-translational processes of the humanized anti-IL-23 antibody, such as changing the number or position of glycosylation sites.

A useful method for identification of certain residues or regions of the humanized anti-IL-23p19 antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with IL-23 antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-IL-23p19 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-IL-23 antibody with an N-terminal methionyl residue or the antibody fused to an epitope tag. Other insertional variants of the humanized anti-IL-23 antibody molecule include the fusion to the N- or C-terminus of humanized anti-IL-23 antibody of an enzyme or a polypeptide which increases the serum half-life of the antibody.

Another type of variant is an amino acid substitution variant. These variants have at least one amino acid residue in the humanized anti-IL-23p19 antibody molecule removed and a different residue inserted in its place. The sites of greatest interest for substitutional mutagenesis include the hypervariable loops, but FR alterations are also contemplated.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. A similar problem may occur at a DG sequence. Reissner and Aswad (2003) *Cell. Mol. Life. Sci.* 60:1281. In one embodiment, the asparagine is changed to glutamine (Q). Isoaspartate formation may debilitate or completely abrogate binding of an antibody to its target antigen. Presta (2005) *J. Allergy Clin. Immunol.* 116:731 at 734. In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease IL-23p19 binding affinity to unacceptable levels.

Nucleic acid molecules encoding amino acid sequence variants of humanized IL-23 specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IL-23p19 antibody.

Ordinarily, amino acid sequence variants of the humanized anti-IL-23 antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95, 98, or 99%. Identity or homology with respect to this sequence is defined herein as the percentage of amino acid residues in the candidate sequence that are identical with the humanized anti-IL-23 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95, 98, or 99%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

CDR and FR residues are determined according to the standard sequence definition of Kabat. Kabat et al. (1987) Sequences of Proteins of Immunological Interest, National Institutes of Health, Bethesda Md. SEQ ID NOs: 5-16, 31-47 and 93-105 show the heavy chain variable domain sequences of various mouse anti-human IL-23p19 antibodies, and SEQ ID NOs: 17-28, 48-64 and 106-118 depict the light chain variable domain sequences. SEQ ID NOs: 65-67 are consensus sequences for heavy chain CDRs (CDRH1, CDRH2 and CDRH3), and are comprised of the most common amino acid residue at each position in the heavy chain CDRs for the family of antibodies consisting of 7G10, 6H12, 13F11, 13B5, 7E2, 13G1, 11C10, 1E10, 30F11, 5B12, 6H4, 9C9, 11B10, 33D2, 20A9, 22E9, 29D5, 21A10, 2G12, 15G2, 18E1 and 2C6. FIGS. 1A-1C provide a sequence lineup of heavy chains of various antibodies of the present invention. This heavy chain variable domain consensus sequence is referred to as conH (SEQ ID NO: 119).

As illustrated in FIGS. 1A-1C, the consensus heavy chain variable domain is closely related to mouse germline sequences IGHV1-14 (SEQ ID NO: 120) in conjunction with IGHD-Q52 (NWD, which is not included in the Sequence Listing because it comprises fewer than four amino acid residues) and either IGHJ2 (SEQ ID NO: 121) or IGHJ3 (SEQ ID NO: 122). The VH subgroups are listed in M.-P. Lefranc (2001) "Nomenclature of the Human Immunoglobulin Heavy (IGH) Genes", *Experimental and Clinical Immunogenetics* 18:100-116. Sequences for these mouse germlines are also available at GenBank Accession Nos. AC090843 (muIGHV1-14), L32868 (nt 2948-2956) (muIGHD-Q52), V00770 (nt 383-430) (muIGHJ2) and V00770 (nt 766-813) (muIGHJ3). In one embodiment of the present invention, the anti-IL-23p19 antibody heavy chain variable region, and particularly CDRH1 and/or CDRH2, comprises a sequence that is closely related to these mouse germline sequences, e.g. mouse germline sequence IGHV1-14. In some embodiments the heavy chain variable region, CDRH1 or CDRH2 exhibit 80%, 85%, 90%, 95%, 98%, 99% or greater homology with mouse germline sequence IGHV1-14. In other embodiments the heavy chain variable region, CDRH1 or CDRH2 exhibit 1, 2, 3, 4, 5, 6, 7, 8, 9, 10, 12, 15, 20 or more amino acid changes relative to mouse germline sequence IGHV1-14. In yet further embodiments such anti-IL-23p19 antibody heavy chains, or CDRH1 and/or CDRH2, may further comprise one or more conservative amino acid substitutions (as defined at Table 1) relative to mouse germline sequence IGHV1-14. In humanized antibody embodiments it is the CDRs, rather than the framework sequences, that are homologous to the recited mouse germlines.

As shown in FIGS. 2A-2C, the light chain CDRs of the antibodies of the present invention disclosed herein are grouped into three subfamilies, referred to as (a), (b) and (c). Light chain subfamily (a) consists of antibodies 7G10, 6H12, 33B12, 13F11, 13B5, 13G1, 11C10, 7E2, 30F11, 34E4, 6H4, 33D2, 2C6, 2G12, 1D6, 18E1, 15G2, 17G8, 20A4, 20H7, 3C4 and 8E9. Light chain subfamily (b) consists of antibodies 1E10, 20A9, 22E9, 29D5, 5B12, 9C9 and 11B10. Light chain subfamily (c) consists of antibodies 10G8, 19E9, 10H11, 39G2, 35F12, 49A10, 34F9 and 7D7. These light chain subfamilies were used to derive consensus CDR sequences of CDRL1(a), CDRL1(b) and CDRL1(c) (SEQ ID NOs: 68-70) and corresponding consensus sequences CDRL2 (SEQ ID NOs: 71-73) and CDRL3 (SEQ ID NOs: 74-76) for each subfamily. Consensus sequences for light chain CDRs are comprised of the most common amino acid residue at each position in the light chain CDRs for each subfamily of antibodies. The light chain variable domain consensus sequences for families (a), (b) and (c) are referred to as conLA (SEQ ID NO: 123), conLB (SEQ ID NO: 125) and conLC (SEQ ID NO: 127) in FIGS. 2A-2C.

As illustrated in FIGS. 2A-2C, the consensus light chain variable domain for family (a) (conLA) is closely related to mouse germline sequence IGKV5-39 (SEQ ID NO: 124); the consensus light chain variable domain for family (b) (conLB) is closely related to mouse germline sequence IGKV8-30 (SEQ ID NO: 126); and the consensus light chain variable domain for family (c) (conLC) is closely related to mouse germline sequence IGVK3-12 (SEQ ID NO: 128). Sequences for these mouse germlines are also available at GenBank Accession Nos. AJ235964 (nt 403-689) (IGKV5-39), AJ235948 (nt 441-745) (IGKV8-30), and K02159 (nt 362-660) (IGKV3-12). In one embodiment of the present invention, the anti-IL-23p19 antibody light chain variable region, and particularly the light chain CDRs, comprises a sequence that is closely related to one or more of these three mouse germline sequences (IGKV5-39, IGKV8-30, IGVK3-12). In some embodiments the light chain variable region, or any of the light chain CDRs, exhibit 80%, 85%, 90%, 95%, 98%, 99% or greater homology with one or more of the three mouse germline sequences. In other embodiments the heavy chain variable region, or any of the light chain CDRs, exhibit 1, 2, 3, 4, 5, 6, 7, 8, 9, 10, 12, 15, 20 or more amino acid changes relative to one or more of the three mouse germline sequences. In yet further embodiments such anti-IL-23p19 antibody light chains, and particularly the light chain CDRs, may further comprise one or more conservative amino acid substitutions (as defined at Table 1) relative to one or more of the three mouse germline sequences. In humanized antibody embodiments it is the CDRs, rather than the framework sequences, that are homologous to the recited mouse germlines.

Tables 2 and 3 define various domains of humanized anti-IL-23p19 antibodies 6H12, 7G10, 10H11, 22E9 and 17G8 (with two variant heavy chain variable domains), as well as and the light and heavy chain variable domains of several murine antibodies of the present invention. Residues 1-19 of SEQ ID NOs: 1-4 represent signal sequences for heavy and light strands of hum6H12 and hum7G10. Light chain constant domains of hum6H12 and hum7G10 are at residues 130-233 of SEQ ID NOs: 2 and 4, respectively. Heavy chain constant domains of hum6H12 and hum7G10 are at residues 135-464 of SEQ ID NOs: 1 and 3, respectively, with CH1 at residues 135-242, CH2+hinge at residues 243-357 and CH3 at residues 358-464. These constant domains may be combined with variable domains from the other murine antibodies disclosed herein to create chimeric antibodies, or with humanized variable domains to create humanized antibodies. All other antibodies are presented as light and heavy chain variable regions ($V_L$ and $V_H$), and thus lack signal sequences and constant domains.

TABLE 2

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDRL1 | CDRL2 | CDRL3 |
| hum6H12 | 2 | 20-129 | 43-53 | 69-75 | 108-116 |
| hum7G10 | 4 | 20-129 | 43-53 | 69-75 | 108-116 |
| hum10H11 | 90 | 1-114 | 24-38 | 54-60 | 93-101 |
| hum22E9 | 92 | 1-116 | 24-40 | 56-62 | 95-103 |
| hum17G8 | 131 | 1-108 | 24-34 | 50-56 | 89-97 |
| m6H12 | 17 | 1-108 | 24-34 | 50-56 | 89-97 |
| m7G10 | 18 | 1-108 | 24-34 | 50-56 | 89-97 |
| m13F11 | 19 | 1-108 | 24-34 | 50-56 | 89-97 |
| m13B5 | 20 | 1-108 | 24-34 | 50-56 | 89-97 |
| m21A10 | 21 | 1-108 | 24-34 | 50-56 | 89-97 |
| m33B12 | 22 | 1-108 | 24-34 | 50-56 | 89-97 |
| m39G2 | 23 | 1-112 | 24-38 | 54-60 | 93-101 |
| m35F12 | 24 | 1-112 | 24-38 | 54-60 | 93-101 |
| m49A10 | 25 | 1-112 | 24-38 | 54-60 | 93-101 |
| m34F9 | 26 | 1-112 | 24-38 | 54-60 | 93-101 |
| m7D7 | 27 | 1-112 | 24-38 | 54-60 | 93-101 |
| m3D7 | 28 | 1-108 | 24-34 | 50-56 | 89-97 |
| m13G1 | 48 | 1-108 | 24-34 | 50-56 | 89-97 |
| m11C10 | 49 | 1-108 | 24-34 | 50-56 | 89-97 |
| m7E2 | 50 | 1-108 | 24-34 | 50-56 | 89-97 |
| m30F11 | 51 | 1-108 | 24-34 | 50-56 | 89-97 |
| m34E4 | 52 | 1-108 | 24-34 | 50-56 | 89-97 |
| m6H4 | 53 | 1-108 | 24-34 | 50-56 | 89-97 |
| m33D2 | 54 | 1-108 | 24-34 | 50-56 | 89-97 |
| m1E10 | 55 | 1-114 | 24-40 | 56-62 | 95-103 |
| m20A9 | 56 | 1-114 | 24-40 | 56-62 | 95-103 |
| m22E9 | 57 | 1-114 | 24-40 | 56-62 | 95-103 |
| m29D5 | 58 | 1-114 | 24-40 | 56-62 | 95-103 |
| m5B12 | 59 | 1-114 | 24-40 | 56-62 | 95-103 |
| m9C9 | 60 | 1-114 | 24-40 | 56-62 | 95-103 |
| m11B10 | 61 | 1-114 | 24-40 | 56-62 | 95-103 |
| m10G8 | 62 | 1-112 | 24-38 | 54-60 | 93-101 |
| m19E9 | 63 | 1-112 | 24-38 | 54-60 | 93-101 |
| m10H11 | 64 | 1-112 | 24-38 | 54-60 | 93-101 |
| m2G12 | 106 | 1-108 | 24-34 | 50-56 | 89-97 |
| m15G2 | 107 | 1-108 | 24-34 | 50-56 | 89-97 |
| m18E1 | 108 | 1-108 | 24-34 | 50-56 | 89-97 |
| m2C6 | 109 | 1-108 | 24-34 | 50-56 | 89-97 |
| m8E9 | 110 | 1-108 | 24-34 | 50-56 | 89-97 |
| m1D6 | 111 | 1-108 | 24-34 | 50-56 | 89-97 |
| m17G8 | 112 | 1-108 | 24-34 | 50-56 | 89-97 |
| m20A4 | 113 | 1-108 | 24-34 | 50-56 | 89-97 |
| m20H7 | 114 | 1-108 | 24-34 | 50-56 | 89-97 |
| m3C4 | 115 | 1-108 | 24-34 | 50-56 | 89-97 |
| m16F7 | 116 | 1-108 | 24-34 | 50-56 | 89-97 |

TABLE 2-continued

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDRL1 | CDRL2 | CDRL3 |
| m14A3 | 117 | 1-112 | 24-38 | 54-60 | 93-101 |
| m12C11 | 118 | 1-112 | 24-38 | 54-60 | 93-101 |

TABLE 3

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDRH1 | CDRH2 | CDRH3 |
| hum6H12 | 1 | 20-134 | 45-54 | 69-85 | 118-123 |
| hum7G10 | 3 | 20-134 | 45-54 | 69-85 | 118-123 |
| hum10H11 | 89 | 1-118 | 26-35 | 50-66 | 99-107 |
| hum22E9 | 91 | 1-115 | 26-35 | 50-66 | 99-104 |
| hum17G8-A | 129 | 1-115 | 26-35 | 50-66 | 99-104 |
| hum17G8-B | 130 | 1-115 | 26-35 | 50-66 | 99-104 |
| m6H12 | 5 | 1-115 | 26-35 | 50-66 | 99-104 |
| m7G10 | 6 | 1-115 | 26-35 | 50-66 | 99-104 |
| m13F11 | 7 | 1-115 | 26-35 | 50-66 | 99-104 |
| m13B5 | 8 | 1-116 | 26-35 | 50-66 | 99-105 |
| m21A10 | 9 | 1-115 | 26-35 | 50-66 | 99-104 |
| m33B12 | 10 | 1-115 | 26-35 | 50-66 | 99-104 |
| m39G2 | 11 | 1-118 | 26-35 | 50-66 | 99-107 |
| m35F12 | 12 | 1-118 | 26-35 | 50-66 | 99-107 |
| m49A10 | 13 | 1-119 | 26-35 | 50-66 | 99-108 |
| m3D7 | 14 | 1-122 | 26-35 | 50-66 | 99-111 |
| m34F9 | 15 | 1-124 | 26-35 | 50-66 | 99-113 |
| m7D7 | 16 | 1-124 | 26-35 | 50-66 | 99-113 |
| m13G1 | 31 | 1-115 | 26-35 | 50-66 | 99-104 |
| m11C10 | 32 | 1-115 | 26-35 | 50-66 | 99-104 |
| m7E2 | 33 | 1-115 | 26-35 | 50-66 | 99-104 |
| m30F11 | 34 | 1-115 | 26-35 | 50-66 | 99-104 |
| m34E4 | 35 | 1-115 | 26-35 | 50-66 | 99-104 |
| m6H4 | 36 | 1-115 | 26-35 | 50-66 | 99-104 |
| m33D2 | 37 | 1-115 | 26-35 | 50-66 | 99-104 |
| m1E10 | 38 | 1-115 | 26-35 | 50-66 | 99-104 |
| m20A9 | 39 | 1-115 | 26-35 | 50-66 | 99-104 |
| m22E9 | 40 | 1-115 | 26-35 | 50-66 | 99-104 |
| m29D5 | 41 | 1-115 | 26-35 | 50-66 | 99-104 |
| m5B12 | 42 | 1-115 | 26-35 | 50-66 | 99-104 |
| m9C9 | 43 | 1-115 | 26-35 | 50-66 | 99-104 |
| m11B10 | 44 | 1-115 | 26-35 | 50-66 | 99-104 |
| m10G8 | 45 | 1-118 | 26-35 | 50-66 | 99-107 |
| m19E9 | 46 | 1-118 | 26-35 | 50-66 | 99-107 |
| m10H11 | 47 | 1-118 | 26-35 | 50-66 | 99-107 |
| m2G12 | 93 | 1-115 | 26-35 | 50-66 | 99-104 |
| m15G2 | 94 | 1-115 | 26-35 | 50-66 | 99-104 |
| m18E1 | 95 | 1-115 | 26-35 | 50-66 | 99-104 |
| m2C6 | 96 | 1-115 | 26-35 | 50-66 | 99-104 |
| m8E9 | 97 | 1-115 | 26-35 | 50-66 | 99-104 |
| m1D6 | 98 | 1-115 | 26-35 | 50-66 | 99-104 |
| m17G8 | 99 | 1-115 | 26-35 | 50-66 | 99-104 |
| m20A4 | 100 | 1-115 | 26-35 | 50-66 | 99-104 |
| m20H7 | 101 | 1-115 | 26-35 | 50-66 | 99-104 |
| m3C4 | 102 | 1-115 | 26-35 | 50-66 | 99-104 |
| m16F7 | 103 | 1-119 | 26-35 | 50-66 | 99-108 |
| m14A3 | 104 | 1-122 | 26-35 | 50-66 | 99-111 |
| m12C11 | 105 | 1-122 | 26-35 | 50-66 | 99-111 |

In one embodiment, the antibodies of the present invention or antigen binding fragments thereof comprise CDRs comprising one of several variable amino acids at certain positions. In one embodiment antibodies of the present invention, or antigen binding fragments thereof, comprise the "CDR Variable" domains listed at SEQ ID NOs: 77-88. These "CDR Variable" sequences include the consensus sequence of each family of related antibodies as well as variable positions encompassing all observed sequence variants within that family. Such sequence variants are displayed in FIGS. 1A-1C and 2A-2C.

In another embodiment, the variable amino acids in potential CDRs are selected from those amino acids appearing two or more times in the families reported herein. These antibodies are a subset of the "CDR Variable" antibodies described above in which amino acids that appear only once at a given position in a CDR in a given family of sequences are not included in the pool of potential CDRs. These "single occurrence" amino acid substitutions are readily determined, and thus excluded from the "CDR Variable" sequences, by simple inspection of FIGS. 1A-1C and 2A-2C. This narrowed range of potential CDR sequences is referred to herein as a "multiple occurrence variable CDR." This nomenclature is used herein for convenience in referring to this subset of the "CDR Variable" sequences.

In yet another embodiment, potential CDRs are not limited to the "CDR Variable" sequences described above, but also include conservatively modified variants of any observed amino acid, as determined using the data of Table 1.

In a further embodiment, potential CDRs include variants of any single sequence CDR disclosed herein, including consensus sequences SEQ ID NOs: 65-76, in which the variant comprises 1, 2, 3, 4, 5, 6, 7, 8, 9, 10 or more conservative amino acid substitutions relative to the disclosed sequence, as determined using the data of Table 1.

Also contemplated are chimeric antibodies. As noted above, typical chimeric antibodies comprise a portion of the heavy and/or light chain identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; and Morrison et al. (1984) *Proc. Natl. Acad. Sci. USA* 81: 6851-6855.

Bispecific antibodies are also useful in the present methods and compositions. As used herein, the term "bispecific antibody" refers to an antibody, typically a monoclonal antibody, having binding specificities for at least two different antigenic epitopes, e.g., IL-23p19 and IL-17. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Biological Activity of Humanized Anti-IL-23

Antibodies having the characteristics identified herein as being desirable in a humanized anti-IL-23 antibody can be screened for inhibitory biologic activity in vitro or suitable binding affinity. To screen for antibodies that bind to the epitope on human IL-23 (i.e. the p19 subunit) bound by an antibody of interest (e.g., those that block binding of the cytokine to its receptor), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at nearby, or even non-overlapping, epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human IL-23 may also be used to determine the functional epitope for an anti-IL-23 antibody of the present invention. Mutagenesis studies, however, may also reveal amino acid residues that are crucial to the overall three-dimensional structure of IL-23 but that are not directly involved in antibody-antigen contacts, and thus other methods may be necessary to confirm a functional epitope determined using this method.

The epitope bound by a specific antibody may also be determined by assessing binding of the antibody to peptides comprising fragments of human IL-23p19 (SEQ ID NO: 39). A series of overlapping peptides encompassing the sequence of IL-23p19 may be synthesized and screened for binding, e.g. in a direct ELISA, a competitive ELISA (where the peptide is assessed for its ability to prevent binding of an antibody to IL-23p19 bound to a well of a microtiter plate), or on a chip. Such peptide screening methods may not be capable of detecting some discontinuous functional epitopes, i.e. functional epitopes that involve amino acid residues that are not contiguous along the primary sequence of the IL-23p19 polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in IL-23 when free and when bound in a complex with an antibody of interest (Zinn-Justin et al. (1992) *Biochemistry* 31:11335-11347; Zinn-Justin et al. (1993) *Biochemistry* 32:6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 4.0 to about 10.0, often from about 7.0 to 8.5, e.g. pH 8.0. Specific buffers useful in the precipitant solution may vary and are well-known in the art. Scopes, Protein Purification: Principles and Practice, Third ed., (1994) Springer-Verlag, New York. Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al. eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323).

Additional antibodies binding to the same epitope as an antibody of the present invention may be obtained, for example, by screening of antibodies raised against IL-23 for binding to the epitope, or by immunization of an animal with a peptide comprising a fragment of human IL-23 comprising the epitope sequence. Antibodies that bind to the same functional epitope might be expected to exhibit similar biological activities, such as blocking receptor binding, and such activities can be confirmed by functional assays of the antibodies.

Antibody affinities (e.g. for human IL-23) may be determined using standard analysis. Preferred humanized antibodies are those which bind human IL-23p19 with a $K_d$ value of no more than about $1 \times 10^{-7}$; preferably no more than about $1 \times 10^{-8}$; more preferably no more than about $1 \times 10^{-9}$; and most preferably no more than about $1 \times 10^{-10}$ or even $1 \times 10^{-11}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of IL-23 to bind its receptor. As used herein, the term "specific" refers to the selective binding of the antibody to the target antigen epitope. Antibodies can be tested for specificity of binding by comparing binding to IL-23 to binding to irrelevant antigen or antigen mixture under a given set of conditions. If the antibody binds to IL-23 at least 10, and preferably 50 times more than to irrelevant antigen or antigen mixture then it is considered to be specific. An antibody that binds to IL-12 is not an IL-23-specific antibody. An antibody that "specifically binds" to IL-23p19 does not bind to proteins that do not comprise the IL-23p19-derived sequences, i.e. "specificity" as used herein relates to IL-23p19 specificity, and not any other sequences that may be present in the protein in question. For example, as used herein, an antibody that "specifically binds" to IL-23p19 will typically bind to FLAG®-hIL-23p19, which is a fusion protein comprising IL-23p19 and a FLAG® peptide tag, but it does not bind to the FLAG® peptide tag alone or when it is fused to a protein other than IL-23p19.

IL-23-specific binding compounds of the present invention, such as inhibitory IL-23p19 specific antibodies, can inhibit its biological activity in any manner, including but not limited to production of IL-1β and TNF by peritoneal macrophages and IL-17 by $T_H17$ T cells. See Langrish et al. (2004) *Immunol. Rev.* 202:96-105. Anti-IL-23p19 antibodies will also be able to inhibit the gene expression of IL-17A, IL-17F, CCL7, CCL17, CCL20, CCL22, CCR1, and GM-CSF. See Langrish et al. (2005) *J. Exp. Med.* 201:233-240. IL-23-specific binding compounds of the present invention, such as anti IL-23p19 antibodies, will also block the ability of IL-23 to enhance proliferation or survival of $T_H17$ cells. Cua and Kastelein (2006) *Nat. Immunol.* 7:557-559. The inhibitory activity of engineered anti-IL-23p19 will be useful in the treatment of inflammatory, autoimmune, and proliferative disorders. Examples of such disorders are described in PCT patent application publications WO 04/081190; WO 04/071517; WO 00/53631; and WO 01/18051.

VI. Pharmaceutical Compositions

To prepare pharmaceutical or sterile compositions including IL-23p19 antibody, the cytokine analogue or mutein, antibody thereto, or nucleic acid thereof, is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

The mode of administration is not particularly important. Suitable routes of administration may, for example, include oral, rectal, transmucosal, or intestinal administration; parenteral delivery, including intramuscular, intradermal, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346: 1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an IL-23p19 specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, or radiation, are well known in the art, see, e.g., Hardman et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., Pa. The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

Typical veterinary, experimental, or research subjects include monkeys, dogs, cats, rats, mice, rabbits, guinea pigs, horses, and humans.

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-IL-23p19 antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, Spodoptera frugiperda ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-IL-23p19 antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for IL-23) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using engineered anti-IL-23 antibodies and fragments thereof for the treatment and diagnosis of inflammatory disorders and conditions, e.g., of the central nervous system, peripheral nervous system, and gastrointestinal tract, as well as autoimmune and proliferative disorders.

Methods are provided for the treatment of, e.g., multiple sclerosis (MS), including relapsing-remitting MS and primary progressive MS, Alzheimer's disease, amyotrophic lateral sclerosis (a.k.a. ALS; Lou Gehrig's disease), ischemic brain injury, prion diseases, and HIV-associated dementia. Also provided are methods for treating neuropathic pain, posttraumatic neuropathies, Guillain-Barre syndrome (GBS), peripheral polyneuropathy, and nerve regeneration.

Provided are methods for treating or ameliorating one or more of the following features, symptoms, aspects, manifestations, or signs of multiple sclerosis, or other inflammatory disorder or condition of the nervous system: brain lesions, myelin lesions, demyelination, demyelinated plaques, visual disturbance, loss of balance or coordination, spasticity, sensory disturbances, incontinence, pain, weakness, fatigue, paralysis, cognitive impairment, bradyphrenia, diplopia, optic neuritis, paresthesia, gait ataxia, fatigue, Uhtoff's symptom, neuralgia, aphasia, apraxia, seizures, visual-field loss, dementia, extrapyramidal phenomena, depression, sense of well-being, or other emotional symptoms, chronic progressive myelopathy, and a symptom detected by magnetic resonance imaging (MRI), including gadolinium-enhancing lesions, evoked potential recordings, or examination of cerebrospinal fluid. See, e.g., Kenealy et al. (2003) *J. Neuroimmunol.* 143:7-12; Noseworthy et al. (2000) *New Engl. J. Med.* 343:938-952; Miller et al. (2003) *New Engl. J. Med.* 348:15-23; Chang et al. (2002) *New Engl. J. Med.* 346:165-173; Bruck and Stadelmann (2003) *Neurol. Sci.* 24 Suppl. 5:S265-S267.

Moreover, the present invention provides methods for treating and diagnosing inflammatory bowel disorders, e.g., Crohn's disease, ulcerative colitis, celiac disease, and irritable bowel syndrome. Provided are methods for treating or ameliorating one or more of the following symptoms, aspects, manifestations, or signs of an inflammatory bowel disorder: malabsorption of food, altered bowel motility, infection, fever, abdominal pain, diarrhea, rectal bleeding, weight loss, signs of malnutrition, perianal disease, abdominal mass, and growth failure, as well as intestinal complications such as stricture, fistulas, toxic megacolon, perforation, and cancer, and including endoscopic findings, such as, friability, aphthous and linear ulcers, cobblestone appearance, pseudopolyps, and rectal involvement and, in addition, anti-yeast antibodies. See, e.g., Podolsky, supra; Hanauer, supra; Horwitz and Fisher, supra.

Also contemplated is treatment of inflammatory disorders such as psoriasis, atopic dermatitis, arthritis, including rheumatoid arthritis, osteoarthritis, and psoriatic arthritis, autoimmune disorders, such as systemic lupus erythematosus and type I diabetes, and proliferative disorders such as cancer. See, e.g., PCT patent applications WO 04/081190; WO 04/071517; WO 00/53631; and WO 01/18051.

The IL-23p19 binding compounds of the present invention can also be used in combination with one or more antagonists of other cytokines (e.g. antibodies), including but not limited to, IL-17A, IL-17F, IL-1β, IL-6 and TGF-β. See, e.g., Veldhoen (2006) *Immunity* 24:179-189; Dong (2006) *Nat. Rev. Immunol.* 6(4):329-333. In various embodiments, an IL-23p19 binding compound of the invention is administered before, concurrently with, or after administration of the another antagonist or antagonists, such as an anti-IL-17A antibody. In one embodiment, an IL-17A binding compound is used in treatment of the acute early phase of an adverse immune response (e.g. MS, Crohn's Disease) alone or in combination with an IL-23 antagonist antibody of the present invention. In the latter case, the IL-17A binding compound may be gradually decreased and treatment with the antagonist of IL-23 alone is continued to maintain suppression of the adverse response. Alternatively, antagonists to IL-1β, IL-6 and/or TGF-β may be administered concurrently, before or after an IL-23p19 binding compound of the present invention. See Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA, Vol.* 217, Academic Press, San Diego, Calif. Standard methods also appear in Ausbel et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, electrophoresis, centrifugation, and crystallization are described. Coligan et al. (2000) *Current Protocols in Protein Science, Vol.* 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science, Vol.* 2, John Wiley and Sons, Inc., New York; Ausubel et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protcols in Immunology, Vol.* 4, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16:741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

Humanization of Anti-Human IL-23p19 Antibodies

The humanization of mouse anti-human IL-23p19 antibodies 6H12 and 7G10, was performed as essentially as described in PCT patent application publications WO 2005/047324 and WO 2005/047326.

Variable light and heavy domains of selected anti-IL-23 monoclonal antibodies (6H12 and 7G10) were cloned and fused to a human kappa light chain (CL domain) and human IgG1 heavy chain (CH1-hinge-CH2-CH3), respectively.

The amino acid sequence of the non-human VH domain was compared to a group of five human VH germline amino acid sequences; one representative from subgroups IGHV1 and IGHV4 and three representatives from subgroup IGHV3. The VH subgroups are listed in M.-P. Lefranc (2001) "Nomenclature of the Human Immunoglobulin Heavy (IGH) Genes", *Experimental and Clinical Immunogenetics* 18:100-116. 6H12 and 7G10 antibodies scored highest against human heavy chain germline DP-14 in subgroup VH1.

For all non-human antibodies, the VL sequences were of the kappa subclass of VL. The amino acid sequence of the non-human VL domain was compared to a group of four human VL kappa germline amino acid sequences. The group of four is comprised of one representative from each of four established human VL subgroups listed in V. Barbie & M.-P. Lefranc (1998) "The Human Immunoglobulin Kappa Variable (IGKV) Genes and Joining (IGKJ) Segments", *Experimental and Clinical Immunogenetics* 15:171-183 and M.-P. Lefranc (2001) "Nomenclature of the Human Immunoglobulin Kappa (IGK) Genes", *Experimental and Clinical Immunogenetics* 18:161-174. The four subgroups also correspond to the four subgroups listed in Kabat et al. (1991-5th Ed.) "Sequences of Proteins of Immunological Interest", U.S. Department of Health and Human Services, NIH Pub.

91-3242, pp. 103-130. 6H12 and 7G10 antibodies scored highest against human light chain germline Z-012 in subgroup VLkI.

An additional amino acid substitution was made in CDRH2 of antibody 6H12, wherein the D residue (Asp) in the parental rodent antibody (SEQ ID NO: 5) was replaced with an A residue (Ala) in the humanized form (SEQ ID NO: 1). This change was made to avoid a potential site for isoaspartate formation.

Once the target amino acid sequences of the variable heavy and light chains were determined, plasmids encoding the full-length humanized antibody were generated. Starting with a plasmid encoding a humanized anti-IL-10 antibody having VH3 DP-46 and VLkI Z-012 germline frameworks, the plasmids were altered using Kunkel mutagenesis (Kunkel (1985) *Proc. Natl. Acad. Sci. U.S.A* 82:488-492) to change the DNA sequence to the target humanized 6H12 or 7G10 sequences. Simultaneously, codon optimization was incorporated into the changes to provide for potentially optimal expression. The resulting humanized heavy and light chain sequences, including signal sequences, are provided at SEQ ID NOs: 1 and 2 (antibody 6H12) and at SEQ ID NOs: 3 and 4 (for antibody 7G10), respectively.

An analogous procedure was performed to determine the proper human frameworks for humanization of antibodies 10H11 and 22E9. Antibody 10H11 scored highest against human antibody heavy chain germline DP-46 in subgroup VH3 and light chain germline Z-A27 in subgroup VLkIII. Antibody 22E9 scored highest against human antibody heavy chain germline DP-14 in subgroup VH1 and light chain germline Z-B3 in subgroup VLkIV. The resulting humanized heavy and light chain variable domain sequences are provided at SEQ ID NOs: 89 and 90 (antibody 10H11) and at SEQ ID NOs: 91 and 92 (antibody 22E9), respectively.

An analogous procedure was performed to determine the proper human frameworks for humanization of antibody 17G8. With regard to the light chain, the humanized form of antibody 17G8 (SEQ ID NO: 131) is based on human antibody light chain germline subgroup I, the same as antibodies 7G10 and 6H12. With regard to the heavy chain, amino acid substitutions were also made in CDRH2 in the humanization process. One form of the humanized heavy chain of 17G8 (SEQ ID NO: 129) is based on human antibody heavy chain germline subgroup I, the same as antibodies 7G10 and 6H12, and has an N (Asn) to K (Lys) substitution at position 63 (N63K). Another form of the humanized heavy chain (SEQ ID NO: 130) is based on human antibody heavy chain germline subgroup III, and has N63K and 159Y substitutions. Residue numbering is according to the Sequence Listing, not Kabat numbering. Humanized antibody 17G8 may comprise the light chain in conjunction with either form of the heavy chain, or with the original rodent CDRs (i.e. SEQ ID NO: 129 with a K63N substitution).

In yet another embodiment, humanized antibody 17G8 comprises a R98A substitution in the humanized 17G8 heavy chain sequence relative to the sequence disclosed at SEQ ID NOs: 129 and 130, which sequences are provided as SEQ ID NOs: 132 and 133, respectively. Residue 98 is not within a CDR as the CDR is typically defined in the Kabat nomenclature. When the R98A substitution is made in the 17G8 heavy chain sequence disclosed at SEQ ID NO: 129 the activity in the Ba/F3 proliferation bioassay improves (i.e. the IC50 decreases) over 1000-fold, to a level similar to the parental mouse antibody prior to humanization.

Humanized forms of other (rodent) antibodies disclosed herein may be constructed using the human frameworks disclosed for humanized antibodies 6H12, 7G10, 10H11, 22E9 or 17G8, or by repeating the procedure for selection of the best human frameworks by the methods disclosed in this Example. Substitution of the human frameworks disclosed herein as part of humanized antibodies 6H12, 7G10, 10H11, 22E9 or 17G8 is most appropriate for antibodies with CDR sequences similar to the respective humanized antibody, such as those falling into the same "sequence families" illustrated in the figures. "Sequence families" are the groupings of antibody sequences used to derive a consensus sequence.

Example 3

Determining the Equilibrium Dissociation Constant ($K_d$) for Humanized Anti-human IL-23 Using KinExA Technology The equilibrium dissociation constant ($K_d$) for anti human IL-23 antibodies is determined using the KinExA 3000 instrument. Sapidyne Instruments Inc., Boise Id., USA KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[\text{Ab}][\text{Ag}]=k_{off}[\text{AbAg}]$$

2. Antibody and antigen bind 1:1 and total antibody equals antigen-antibody complex plus free antibody.

3. Instrument signal is linearly related to free antibody concentration.

98 micron PMMA particles (Sapidyne, Cat No. 440198) are coated with biotinylated rhIL-23 according to Sapidyne "Protocol for coating PMMA particles with biotinylated ligands having short or nonexistent linker arms". To make biotinylated rhIL-23, EZ-link TFP PEO-biotin (Pierce, Cat. No. 21219) is used according to manufacturer's recommendations (Pierce bulletin 0874). Experimental procedures are done according to the KinExA 3000 manual.

Three forms of the heterodimeric IL-23 protein are used. Native or non-linked human IL-23 is comprised of two disulfide-linked chains, p19 and p40. "Non-linked" IL-23 is comprised of human p40 coexpressed in 293T cells with human p19:FLAG®-tag peptide and purified over an anti-FLAG® peptide affinity column.

"Elastikine" IL-23 is a single-chain peptide comprised of FLAG®-tag peptide:GLU-tag peptide:human p40:elasti-linker:human p19. The elasti-linker peptide sequence is derived from R&D Systems form of commercial IL-23. R&D Systems, Minneapolis, Minn., USA. Elastikine is expressed in 293T cells and purified over an anti-FLAG® peptide affinity column.

A non-tagged, non-linked form of native human IL-23p19/p40 coexpressed in SF9 cells is purchased from eBioscience (CAT No. 34-8239). eBioscience, San Diego, Calif., USA.

KinExA experiments are performed essentially as described at Example 3 of U.S. Patent Application Publication No. 2007/0048315. Table 4 shows the results of the KinExA analysis.

TABLE 4

$K_d$ Values Determined by KinExA

| Human IL-23 | Antibody | $K_d$ (pM) |
|---|---|---|
| elastikine | 6H12 | 54, 48 |
| non-linked | 6H12 | >1200 |
| eBioscience | 6H12 | >1000, >920 |
| elastikine | hu6H12 | 28, 36 |
| elastikine | 7G10 | 41, 9.2 |
| elastikine | hu7G10 | 49, 16 |
| elastikine | 39G2 | 19 |
| non-linked | 39G2 | 34 |
| eBioscience | 39G2 | 620 |
| elastikine | 35F12 | 53 |
| eBioscience | 35F12 | >700 |
| elastikine | 13B5 | 22 |
| eBioscience | 13B5 | 55 |
| elastikine | 7D7 | 2.7 |
| elastikine | 3D7 | 0.84 |
| elastikine | 49A10 | 7.4 |
| elastikine | 13F11 | 11 |
| elastikine | 33B12 | 6.8 |

Example 4

Determining the Equilibrium Dissociation Constant ($K_d$) for Humanized Anti-Human IL-23p19 Antibodies Using BIAcore Technology BIAcore determinations are performed essentially as described at Example 4 of U.S. Patent Application Publication No. 2007/0048315. Briefly, ligands (anti-IL-23 mAbs) are immobilized on a BIAcore CM5 sensor chip using standard amine-coupling procedure. IL-23 (various forms) is diluted in PBS to produce various concentrations. Kinetic constants for the various interactions are determined using BIAevaluation software 3.1. The $K_d$ is determined using the calculated dissociation and association rate constants. In certain experiments, proteins are used at the following concentrations: anti-IL-23 mAb hu7G10 in PBS at 0.33 mg/mL; anti-IL-23 mAb hu6H12 in PBS at 0.2 mg/mL; bac-wt human IL-23 in PBS at 0.30 mg/mL; eBioscience human IL-23 in PBS at 0.10 mg/mL; N222Q human IL-23 in PBS at 0.33 mg/mL.

In addition to the forms of IL-23 described in Example 3, other forms are also used. "Bac-wt" human IL-23 is identical to "elastikine" human IL-23 in sequence. This IL-23 is expressed in SF9 cells and purified over an anti-FLAG® peptide affinity column. "N222Q" human IL-23 is identical to "elastikine" human IL-23 in sequence except for alteration of Asn222 to Gln in the p40 subunit (GenBank Accession No. P29460). This IL-23 is expressed in SF9 cells and purified over an anti-FLAG® peptide affinity column.

Table 5 provides the $K_d$ values as determined by BIAcore.

TABLE 5

$K_d$ Determination by BIAcore

| Human IL-23 | Antibody | $K_d$ (nM) |
|---|---|---|
| bac-wt | hu7G10 | 10 |
| N222Q | hu7G10 | 0.3, 1.0 |
| eBioscience | hu7G10 | 3.2, 9.0 |
| bac-wt | hu6H12 | 5.1 |
| N222Q | hu6H12 | 0.5 |
| eBioscience | hu6H12 | 4.1 |

Example 5

Proliferation Bioassays for the Assessment of Neutralizing Anti-IL-23 Antibodies The ability of a monoclonal antibody to biologically neutralize IL-23 is assessed by the application of short-term proliferation bioassays that employ cells that express recombinant IL-23 receptors. The IL-23R transfectant cell line (Ba/F3-2.210-hIL-23R) expresses both hIL-23R and hIL-12Rl31, and is responsive to both human IL-23 and cynomolgus monkey IL-23. The transfectant Ba/F3-2.2lo cells proliferate in response to human IL-23 and the response can be inhibited by a neutralizing anti-IL-23 antibody. An antibody is titrated against a concentration of IL-23 chosen within the linear region of the dose-response curve, near plateau and above EC50. Proliferation, or lack thereof, is measured by colorimetric means using Alamar Blue, a growth indicator dye based on detection of metabolic activity. The ability of an antibody to neutralize IL-23 is assessed by its IC50 value, or concentration of antibody that induces half-maximal inhibition of IL-23 proliferation.

Ba/F3 transfectants are maintained in RPMI-1640 medium, 10% fetal calf serum, 50 µM 2-mercaptoethanol, 2 mM L-Glutamine, 50 µg/mL penicillin-streptomycin, and 10 ng/mL mouse IL-3. Ba/F3 proliferation bioassays are performed in RPMI-1640 medium, 10% fetal calf serum, 50 µM 2-mercaptoethanol, 2 mM L-Glutamine, and 50 µg/mL penicillin-streptomycin.

Assays are performed in 96-well flat bottom plates in 150 µL per well. Anti-IL-23 antibodies are pre-incubated with IL-23 for 30-60 min, followed by addition of cells and incubation for 40-48 hours. Alamar Blue (Biosource Cat #DAL1100) is added and allowed to develop for 5-12 hours. Absorbance is then read at 570 nm and 600 nm (VERSAmax Microplate Reader, Molecular Probes, Eugene, Oreg., USA), and an $OD_{570-600}$ is obtained.

Cells are used in a healthy growth state, generally at densities of $3-8 \times 10^5$/mL. Cells are counted, pelleted, washed twice in bioassay medium, and suspended to the appropriate density for plating. An IL-23 dose response is performed using serial 1:3 dilutions (25:50 µL in bioassay medium) of IL-23. A neutralizing antibody dose response is also performed using serial 1:3 dilutions (25:50 µL in bioassay medium).

IC50 values are determined using GraphPad Prism® 3.0 software (Graphpad Software Inc., San Diego, Calif., USA), in which absorbance is plotted against cytokine or antibody concentration and IC50 values are determined using non-linear regression (curve fit) of sigmoidal dose-response.

Table 6 shows the IC50 values for blocking of Ba/F3 cell proliferation by anti-IL-23p19 antibodies. Values for multiple determinations are included for some antibodies, and values with standard deviations (±SD) are provided for others.

TABLE 6

IC50 Values for Blocking of Ba/F3 Cell Proliferation by Anti-IL-23 Antibodies

| Antibody | Human IL-23 | IC50 (pM) |
|---|---|---|
| 7G10 | elastikine | 22, 18 |
| 7G10 | non-linked | 3000 |
| 7G10 | eBioscience | 3100, 510 |
| hu7G10 | elastikine | 29 |
| hu7G10 | non-linked | 10000 |
| hu7G10 | eBioscience | 7800 |

TABLE 6-continued

IC50 Values for Blocking of Ba/F3 Cell Proliferation by Anti-IL-23 Antibodies

| Antibody | Human IL-23 | IC50 (pM) |
|---|---|---|
| 6H12 | elastikine | 9, 11 |
| 6H12 | non-linked | 1500 |
| 6H12 | eBioscience | 1300, 500 |
| hu6H12 | elastikine | 27 |
| hu6H12 | non-linked | 4000 |
| hu6H12 | eBioscience | 3200 |
| 13B5 | elastikine | 7, 5 |
| 13B5 | non-linked | 113 |
| 13B5 | eBioscience | 31 |
| 33B12 | elastikine | 4, 3 |
| 33B12 | non-linked | 193 |
| 33B12 | eBioscience | 57 |
| 39G2 | elastikine | 9, 5 |
| 39G2 | non-linked | 67 |
| 39G2 | eBioscience | 11 |
| 35F12 | elastikine | 15, 5 |
| 35F12 | non-linked | 73 |
| 35F12 | eBioscience | 12 |
| 3D7 | elastikine | 3, 3 |
| 3D7 | non-linked | 37 |
| 3D7 | eBioscience | 2 |
| 17G8 | non-linked | 3 ± 2 |
| 2G12 | non-linked | 183 ± 60 |
| 15G2 | non-linked | 133 ± 17 |
| 18E1 | non-linked | 48 ± 8 |
| 2C6 | non-linked | 11 ± 3 |
| 8E9 | non-linked | 8 ± 5 |
| 1D6 | non-linked | 16 ± 7 |
| 20A4 | non-linked | 5 ± 3 |
| 20H7 | non-linked | 3 ± 1 |
| 3C4 | non-linked | 12 ± 10 |
| 16F7 | non-linked | 141 ± 23 |
| 14A3 | non-linked | 135 ± 25 |
| 12C11 | non-linked | 57 ± 13 |

Example 6

Epitope for Anti-IL-23p19 Antibody 7G10

The epitope for the binding of antibody 7G10 to human IL-23p19 is determined by X-ray crystallography. Coordinates are determined for a complex of an Fab fragment of the chimeric form of antibody 7G10 and non-linked human IL-23, which comprises p19 and p40 subunits. Crystallization conditions are 12% polyethylene glycol 3350, 200 mM ammonium citrate, 100 mM HEPES-NaOH (pH 8). Crystals may also be obtained with other buffers at or around pH 8.

The sequence of human IL-23p19 is found at SEQ ID NO: 29 and the sequence of the mature form of human IL-12/IL-23 p40 is found at residues 23-328 of GenBank Accession No. P29460. The p40 subunit in the IL-23 used to determine the crystal structure is the N222Q variant, as described supra. The chimeric form of antibody 7G10 comprises i) a heavy chain comprising the mouse 7G10 $V_H$ domain (SEQ ID NO: 6) fused to a human heavy chain constant region (residues 135-464 of SEQ ID NO: 3), and ii) a light chain comprising the mouse 7G10 $V_L$ domain (SEQ ID NO: 18) fused to a human light chain constant region (residues 130-233 of SEQ ID NO: 4).

IL-23 amino acid residues within 4.0 Å of residues on antibody 7G10 include E82, G86, S87, D88, T91, G92, E93, P94, S95, H106, P133, S134, Q135, P136, W137, R139, L140. Additional residues K83, F90 and L110 are within 5.0 Å. An amino acid residue on IL-23p19 is considered to be within a given distance of the antibody (e.g. 4.0 Å or 5.0 Å) if the coordinates of any atom of the residue are within the given distance of the coordinates of any atom of the antibody.

Most of these contacted residues fall into two main clusters along the primary structure of IL-23p19, with the first cluster comprising residues 82-95 (in which 11 of 14 residues are within 5.0 Å of the antibody and 9 of 14 are within 4.0 Å) and the second cluster comprising residues 133-140 (in which 7 of 8 residues are within 4.0 Å of the antibody). These clusters define epitopes comprising stretches of 8 or more contiguous amino acid residues of IL-23p19 in which 50%, 70% and 85% or more of the residues are within 5.0 Å of the antibody.

Antibodies binding to either or both of these clusters would be expected to block binding of antibody 7G10. Given the strong sequence homology between all six CDR sequences (see FIGS. 1A-1C and 2A-2C), it is likely that the other antibodies in both the "(a)" light chain subfamily (conLA) and the heavy chain consensus subfamily (conH), i.e. antibodies 6H12, 13F11, 13B5, 13G1, 11C10, 7E2, 30F11, 6H4, 33D2, 2C6, 2G12, 18E1, 15G2, 17G8, will also bind to substantially the same epitope in IL-23p19 as antibody 7G10. The consensus CDR sequences for the antibodies of the "(a)" light chain subfamily" variable domain sequence are provided at SEQ ID NOs: 68, 71 and 74. Corresponding heavy chain variable domain consensus sequences are provided at SEQ ID NOs: 65-67. Antibodies binding to the same epitope as antibody 7G10 would be expected to exhibit similar biological activities, such as blocking Ba/F3 cell proliferation in the assay described at Example 5 and Table 6, albeit with perhaps somewhat variable affinities and IC50s.

Example 7

Mouse Splenocyte Assay for IL-23 Based on IL-17 Production

The biological activity of anti-IL-23p19 antibodies of the present invention is assessed using the splenocyte assay essentially as described in Aggarwal et al. (2003) *J. Biol. Chem.* 278:1910 and Stumhofer et al. (2006) *Nature Immunol.* 7:937. The mouse splenocyte assay measures the activity of IL-23 in a sample as a level of IL-17 production by murine splenocytes. The inhibitory activity of anti-IL-23p19 antibodies is then assessed by determining the concentration of antibody necessary to reduce the IL-23 activity in a given sample by 50% (the IC50). The IC50 as measured by this assay is greater than or equal to the equilibrium dissociation binding constant ($K_d$), i.e. the $K_d$ may be equal to or lower than the IC50. As always, lower IC50 and $K_d$ values reflect higher activities and affinities.

Briefly, spleens are obtained from 8-12 wk old female C57BL/6J mice (Jackson Laboratories, Bar Harbor, Me., USA). Spleens are ground, pelleted twice, and filtered through a cell strainer (70 μm nylon). The recovered cells are cultured in 96-well plates ($4 \times 10^5$ cells/well) in the presence of human IL-23 (10 ng/ml, ~170 pM) and mouse-anti-CD3e antibodies (1 μg/ml) (BD Pharmingen, Franklin Lakes, N.J., USA), with or without the anti-IL-23p19 antibody to be assayed. Anti IL-23p19 antibodies are added at 10 μg/ml and at a series of 3-fold dilutions. Cells are cultured for 72 hours, pelleted, and the supernatant is assayed for IL-17 levels by sandwich ELISA.

IL-17 ELISA is performed as follows. Plates are coated with a capture anti-IL-17 antibody (100 ng/well) overnight at 4° C., washed and blocked. Samples and standards are added and incubated for two hours at room temperature with shaking Plates are washed, and a biotinylated anti-IL-17 detection antibody (100 ng/well) is added and incubated for one hour at room temperature with shaking. The capture and detection antibodies are different antibodies that both bind to mouse IL-17 but do not cross-block. Plates are washed, and bound detection antibody is detected using streptavidin-HRP (horseradish peroxidase) and TMB (3,3',5,5'-tetramethylbenzidine). The plate is then read at 450-650 nm and the concentration of IL-17 in samples is calculated by comparison with standards.

Splenocyte assay IC50 values for several antibodies of the present invention are provided at Table 7. The antibodies tested show IC50s of 14-155 pM.

TABLE 7

Splenocyte Assay IC50s

| Antibody Clone | IC50 (pM) |
| --- | --- |
| m17G8 | 18 |
| m2G12 | 106 |
| m15G2 | 95 |
| m18E1 | 92 |
| m2C6 | 37 |
| m8E9 | 34 |
| m1D6 | 27 |
| m20A4 | 24 |
| m20H7 | 33 |
| m3C4 | 14 |
| m16F7 | 155 |
| m14A3 | 53 |
| m12C11 | 79 |

Table 8 provides a brief description of the sequences in the sequence listing. SEQ ID NOs. 93-133 (*) are not disclosed in U.S. Patent Application Publication No. 2007/0048315. SEQ ID NOs. 77-80, 83 and 88 (**) are modified forms of SEQ ID NOs. 78-81, 84 and 89 of U.S. Patent Application Publication No. 2007/0048315 comprising additional variability at one or more positions.

TABLE 8

Sequence Identifiers

| SEQ ID NO: | Description |
| --- | --- |
| 1 | hum6H12 HC |
| 2 | hum6H12 LC |
| 3 | hum7G10 HC |
| 4 | hum7G10 LC |
| 5 | m6H12 $V_H$ |
| 6 | m7G10 $V_H$ |
| 7 | m13F11 $V_H$ |
| 8 | m13B5 $V_H$ |
| 9 | m21A10 $V_H$ |
| 10 | m33B12 $V_H$ |
| 11 | m39G2 $V_H$ |
| 12 | m35F12 $V_H$ |
| 13 | m49A10 $V_H$ |
| 14 | m3D7 $V_H$ |
| 15 | m34F9 $V_H$ |
| 16 | m7D7 $V_H$ |
| 17 | m6H12 $V_L$ |
| 18 | m7G10 $V_L$ |
| 19 | m13F11 $V_L$ |
| 20 | m13B5 $V_L$ |
| 21 | m21A10 $V_L$ |
| 22 | m33B12 $V_L$ |
| 23 | m39G2 $V_L$ |
| 24 | m35F12 $V_L$ |
| 25 | m49A10 $V_L$ |
| 26 | m34F9 $V_L$ |
| 27 | m7D7 $V_L$ |
| 28 | m3D7 $V_L$ |
| 29 | Human IL23p19 |
| 30 | Murine IL-23p19 |
| 31 | m13G1 $V_H$ |
| 32 | m11C10 $V_H$ |

TABLE 8-continued

Sequence Identifiers

| SEQ ID NO: | Description |
| --- | --- |
| 33 | m7E2 $V_H$ |
| 34 | m30F11 $V_H$ |
| 35 | m34E4 $V_H$ |
| 36 | m6H4 $V_H$ |
| 37 | m33D2 $V_H$ |
| 38 | m1E10 $V_H$ |
| 39 | m20A9 $V_H$ |
| 40 | m22E9 $V_H$ |
| 41 | m29D5 $V_H$ |
| 42 | m5B12 $V_H$ |
| 43 | m9C9 $V_H$ |
| 44 | m11B10 $V_H$ |
| 45 | m10G8 $V_H$ |
| 46 | m19E9 $V_H$ |
| 47 | m10H11 $V_H$ |
| 48 | m13G1 $V_L$ |
| 49 | m11C10 $V_L$ |
| 50 | m7E2 $V_L$ |
| 51 | m30F11 $V_L$ |
| 52 | m34E4 $V_L$ |
| 53 | m6H4 $V_L$ |
| 54 | m33D2 $V_L$ |
| 55 | m1E10 $V_L$ |
| 56 | m20A9 $V_L$ |
| 57 | m22E9 $V_L$ |
| 58 | m29D5 $V_L$ |
| 59 | m5B12 $V_L$ |
| 60 | m9C9 $V_L$ |
| 61 | m11B10 $V_L$ |
| 62 | m10G8 $V_L$ |
| 63 | m19E9 $V_L$ |
| 64 | m10H11 $V_L$ |
| 65 | CDRH1 Consensus |
| 66 | CDRH2 Consensus |
| 67 | CDRH3 Consensus |
| 68 | CDRL1(a) Consensus |
| 69 | CDRL1(b) Consensus |
| 70 | CDRL1(c) Consensus |
| 71 | CDRL2(a) Consensus |
| 72 | CDRL2(b) Consensus |
| 73 | CDRL2(c) Consensus |
| 74 | CDRL3(a) Consensus |
| 75 | CDRL3(b) Consensus |
| 76 | CDRL3(c) Consensus |
| 77 | CDRH1 Variable** |
| 78 | CDRH2 Variable** |
| 79 | CDRH3 Variable** |
| 80 | CDRL1(a) Variable** |
| 81 | CDRL1(b) Variable |
| 82 | CDRL1(c) Variable |
| 83 | CDRL2(a) Variable** |
| 84 | CDRL2(b) Variable |
| 85 | CDRL2(c) Variable |
| 86 | CDRL3(a) Variable |
| 87 | CDRL3(b) Variable |
| 88 | CDRL3(c) Variable** |
| 89 | hum10H11 $V_H$ |
| 90 | hum10H11 $V_L$ |
| 91 | hum22E9 $V_H$ |
| 92 | hum22E9 $V_L$ |
| 93 | m2G12 $V_H$* |
| 94 | m15G2 $V_H$* |
| 95 | m18E1 $V_H$* |
| 96 | m2C6 $V_H$* |
| 97 | m8E9 $V_H$* |
| 98 | m1D6 $V_H$* |
| 99 | m17G8 $V_H$* |
| 100 | m20A4 $V_H$* |
| 101 | m20H7 $V_H$* |
| 102 | m3C4 $V_H$* |
| 103 | m16F7 $V_H$* |
| 104 | m14A3 $V_H$* |
| 105 | m12C11 $V_H$* |
| 106 | m2G12 $V_L$* |
| 107 | m15G2 $V_L$* |
| 108 | m18E1 $V_L$* |

TABLE 8-continued

| SEQ ID NO: | Description |
|---|---|
| 109 | m2C6 $V_L$* |
| 110 | m8E9 $V_L$* |
| 111 | m1D6 $V_L$* |
| 112 | m17G8 $V_L$* |
| 113 | m20A4 $V_L$* |
| 114 | m20H7 $V_L$* |
| 115 | m3C4 $V_L$* |
| 116 | m16F7 $V_L$* |
| 117 | m14A3 $V_L$* |
| 118 | m12C11 $V_L$* |
| 119 | $V_H$ consensus A* |
| 120 | muIGHV1-14 germline* |
| 121 | muIGHJ2 germline* |
| 122 | muIGHJ3 germline* |
| 123 | $V_L$ consensus A* |
| 124 | muIGKV5-39 germline* |
| 125 | $V_L$ consensus B* |
| 126 | muIGKV8-30 germline* |
| 127 | $V_L$ consensus C* |
| 128 | muIGKV3-12 germline* |
| 129 | hum17G8 $V_H$A * |
| 130 | hum17G8 $V_H$B * |
| 131 | hum17G8 $V_L$* |
| 132 | hum17G8 $V_H$ A R98A* |
| 133 | hum17G8 $V_H$ B R98A* |

What is claimed is:

1. An isolated binding compound that binds to human IL-23, comprising:
   a) an antibody light chain variable region, or antigen binding fragment thereof, comprising:
   CDRL1 comprising residues 24-34 of SEQ ID NO: 131;
   CDRL2 comprising residues 50-56 of SEQ ID NO: 131;
   CDRL3 comprising residues 89-97 of SEQ ID NO: 131; and
   b) an antibody heavy chain variable region, or antigen binding fragment thereof, comprising:
   CDRH1 comprising residues 26-35 of SEQ ID NO: 130;
   CDRH2 comprising residues 50-66 of a sequence selected from the group consisting of SEQ ID NOs: 99, 129 and 130; and
   CDRH3 comprising residues 99-104 of SEQ ID NO: 130.

2. The binding compound of claim 1, wherein the binding compound is an antibody or antigen binding fragment thereof.

3. The binding compound of claim 1, wherein the binding compound is an antibody or antigen binding fragment thereof comprising:
   a) an antibody light chain variable region, or antigen binding fragment thereof, comprising the sequence of SEQ ID NO: 131; and
   b) an antibody heavy chain variable region, or antigen binding fragment thereof, comprising the sequence of SEQ ID NO: 129, 130, 132 or 133.

4. The binding compound of claim 3, wherein the binding compound is an antibody or antigen binding fragment thereof comprising:
   a) a light chain variable region comprising the sequence of SEQ ID NO: 131; and
   b) a heavy chain variable region comprising the sequence of SEQ ID NO: 130.

5. The isolated binding compound of claim 1, wherein the binding compound is an antibody fragment selected from the group consisting of Fab, Fab', Fab'-SH, Fv, scFv, F(ab')$_2$, and a diabody.

6. An isolated antibody, or antigen binding fragment thereof, that is able to block binding of a binding compound to human IL-23 in a cross-blocking assay, wherein the binding compound comprises:
   a) a light chain variable region comprising the sequence of SEQ ID NO: 131; and
   b) a heavy chain variable region comprising the sequence of SEQ ID NO: 130.

7. The binding compound of claim 6 wherein the binding compound blocks IL-23 mediated activity.

* * * * *

SEQUENCE LISTING

```
<160> NUMBER OF SEQ ID NOS: 133

<210> SEQ ID NO 1
<211> LENGTH: 464
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: SIGNAL
<222> LOCATION: (1)..(19)
<220> FEATURE:
<221> NAME/KEY: DOMAIN
<222> LOCATION: (20)..(134)
<223> OTHER INFORMATION: Heavy chain variable domain
<220> FEATURE:
<221> NAME/KEY: MISC_FEATURE
<222> LOCATION: (45)..(54)
<223> OTHER INFORMATION: CDR-H1
<220> FEATURE:
<221> NAME/KEY: MISC_FEATURE
<222> LOCATION: (69)..(85)
<223> OTHER INFORMATION: CDR-H2
<220> FEATURE:
<221> NAME/KEY: MISC_FEATURE
<222> LOCATION: (118)..(123)
<223> OTHER INFORMATION: CDR-H3
<220> FEATURE:
<221> NAME/KEY: DOMAIN
<222> LOCATION: (135)..(242)
<223> OTHER INFORMATION: Heavy chain constant domain 1
<220> FEATURE:
<221> NAME/KEY: DOMAIN
<222> LOCATION: (243)..(357)
<223> OTHER INFORMATION: Heavy chain constant domain 2 and hinge
<220> FEATURE:
<221> NAME/KEY: DOMAIN
<222> LOCATION: (358)..(464)
<223> OTHER INFORMATION: Heavy chain constant domain 3

<400> SEQUENCE: 1

Met Ala Val Leu Gly Leu Leu Phe Cys Leu Val Thr Phe Pro Ser Cys
 1               5                  10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Asn Arg Tyr Leu Ile His Trp Val Arg Gln Ala Pro Gly Gln Gly Leu
    50                  55                  60

Glu Trp Met Gly Tyr Ile Asn Pro Asn Asn Ala Gly Thr Asn Tyr Asn
```

```
            65                  70                  75                  80
Glu Lys Phe Lys Gly Arg Val Thr Met Thr Thr Asp Thr Ser Thr Ser
                    85                  90                  95

Thr Ala Tyr Met Glu Leu Arg Ser Leu Arg Ser Asp Asp Thr Ala Val
            100                 105                 110

Tyr Tyr Cys Ala Arg Asn Trp Asp Gln Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 2
<211> LENGTH: 233
<212> TYPE: PRT
<213> ORGANISM: Artificial Sequence
<220> FEATURE:
```

```
<223> OTHER INFORMATION: Human frameworks, rodent CDRs
<220> FEATURE:
<221> NAME/KEY: SIGNAL
<222> LOCATION: (1)..(19)
<220> FEATURE:
<221> NAME/KEY: DOMAIN
<222> LOCATION: (20)..(129)
<223> OTHER INFORMATION: Light chain variable domain
<220> FEATURE:
<221> NAME/KEY: MISC_FEATURE
<222> LOCATION: (43)..(53)
<223> OTHER INFORMATION: CDR-L1
<220> FEATURE:
<221> NAME/KEY: MISC_FEATURE
<222> LOCATION: (69)..(75)
<223> OTHER INFORMATION: CDR-L2
<220> FEATURE:
<221> NAME/KEY: MISC_FEATURE
<222> LOCATION: (108)..(116)
<223> OTHER INFORMATION: CDR-L3
<220> FEATURE:
<221> NAME/KEY: DOMAIN
<222> LOCATION: (130)..(233)
<223> OTHER INFORMATION: Light chain constant domain

<400> SEQUENCE: 2
```

| Met | Ala | Pro | Val | Gln | Leu | Leu | Gly | Leu | Leu | Val | Leu | Phe | Leu | Pro | Ala |
|---|---|---|---|---|---|---|---|---|---|---|---|---|---|---|---|
| 1 | | | | 5 | | | | | 10 | | | | | 15 | |

| Met | Arg | Cys | Asp | Ile | Gln | Met | Thr | Gln | Ser | Pro | Ser | Ser | Leu | Ser | Ala |
|---|---|---|---|---|---|---|---|---|---|---|---|---|---|---|---|
| | | | 20 | | | | | 25 | | | | | 30 | | |

| Ser | Val | Gly | Asp | Arg | Val | Thr | Ile | Thr | Cys | Arg | Ala | Ser | Gln | Ser | Ile |
|---|---|---|---|---|---|---|---|---|---|---|---|---|---|---|---|
| | | 35 | | | | | 40 | | | | | 45 | | | |

| Ser | Asp | Tyr | Leu | His | Trp | Tyr | Gln | Gln | Lys | Pro | Gly | Lys | Ala | Pro | Lys |
|---|---|---|---|---|---|---|---|---|---|---|---|---|---|---|---|
| 50 | | | | | 55 | | | | | 60 | | | | | |

| Leu | Leu | Ile | Tyr | Tyr | Thr | Ser | Gln | Ser | Ile | Ser | Gly | Val | Pro | Ser | Arg |
|---|---|---|---|---|---|---|---|---|---|---|---|---|---|---|---|
| 65 | | | | | 70 | | | | | 75 | | | | | 80 |

| Phe | Ser | Gly | Ser | Gly | Ser | Gly | Thr | Asp | Phe | Thr | Leu | Thr | Ile | Ser | Ser |
|---|---|---|---|---|---|---|---|---|---|---|---|---|---|---|---|
| | | | | 85 | | | | | 90 | | | | | 95 | |

| Leu | Gln | Pro | Glu | Asp | Phe | Ala | Thr | Tyr | Tyr | Cys | Gln | Asn | Gly | His | Ser |
|---|---|---|---|---|---|---|---|---|---|---|---|---|---|---|---|
| | | | 100 | | | | | 105 | | | | | 110 | | |

| Phe | Pro | Phe | Thr | Phe | Gly | Gln | Gly | Thr | Lys | Val | Glu | Ile | Lys | Arg | Thr |
|---|---|---|---|---|---|---|---|---|---|---|---|---|---|---|---|
| | | 115 | | | | | 120 | | | | | 125 | | | |

| Val | Ala | Ala | Pro | Ser | Val | Phe | Ile | Phe | Pro | Pro | Ser | Asp | Glu | Gln | Leu |
|---|---|---|---|---|---|---|---|---|---|---|---|---|---|---|---|
| | 130 | | | | | 135 | | | | | 140 | | | | |

| Lys | Ser | Gly | Thr | Ala | Ser | Val | Val | Cys | Leu | Leu | Asn | Asn | Phe | Tyr | Pro |
|---|---|---|---|---|---|---|---|---|---|---|---|---|---|---|---|
| 145 | | | | | 150 | | | | | 155 | | | | | 160 |

| Arg | Glu | Ala | Lys | Val | Gln | Trp | Lys | Val | Asp | Asn | Ala | Leu | Gln | Ser | Gly |
|---|---|---|---|---|---|---|---|---|---|---|---|---|---|---|---|
| | | | 165 | | | | | 170 | | | | | 175 | | |

| Asn | Ser | Gln | Glu | Ser | Val | Thr | Glu | Gln | Asp | Ser | Lys | Asp | Ser | Thr | Tyr |
|---|---|---|---|---|---|---|---|---|---|---|---|---|---|---|---|
| | | | 180 | | | | | 185 | | | | | 190 | | |

| Ser | Leu | Ser | Ser | Thr | Leu | Thr | Leu | Ser | Lys | Ala | Asp | Tyr | Glu | Lys | His |
|---|---|---|---|---|---|---|---|---|---|---|---|---|---|---|---|
| | | 195 | | | | | 200 | | | | | 205 | | | |

| Lys | Val | Tyr | Ala | Cys | Glu | Val | Thr | His | Gln | Gly | Leu | Ser | Ser | Pro | Val |
|---|---|---|---|---|---|---|---|---|---|---|---|---|---|---|---|
| | 210 | | | | | 215 | | | | | 220 | | | | |

| Thr | Lys | Ser | Phe | Asn | Arg | Gly | Glu | Cys |
|---|---|---|---|---|---|---|---|---|
| 225 | | | | | 230 | | | |

```
<210> SEQ ID NO 3
<211> LENGTH: 464
<212> TYPE: PRT
<213> ORGANISM: Artificial Sequence
<220> FEATURE:
<223> OTHER INFORMATION: Human frameworks, mouse CDRs
<220> FEATURE:
```

-continued

```
<221> NAME/KEY: SIGNAL
<222> LOCATION: (1)..(19)
<220> FEATURE:
<221> NAME/KEY: DOMAIN
<222> LOCATION: (20)..(134)
<223> OTHER INFORMATION: Heavy chain variable domain
<220> FEATURE:
<221> NAME/KEY: MISC_FEATURE
<222> LOCATION: (45)..(54)
<223> OTHER INFORMATION: CDR-H1
<220> FEATURE:
<221> NAME/KEY: MISC_FEATURE
<222> LOCATION: (69)..(85)
<223> OTHER INFORMATION: CDR-H2
<220> FEATURE:
<221> NAME/KEY: MISC_FEATURE
<222> LOCATION: (118)..(123)
<223> OTHER INFORMATION: CDR-H3
<220> FEATURE:
<221> NAME/KEY: DOMAIN
<222> LOCATION: (135)..(242)
<223> OTHER INFORMATION: CH1 domain
<220> FEATURE:
<221> NAME/KEY: DOMAIN
<222> LOCATION: (243)..(357)
<223> OTHER INFORMATION: CH2 domain and hinge
<220> FEATURE:
<221> NAME/KEY: DOMAIN
<222> LOCATION: (358)..(464)
<223> OTHER INFORMATION: CH3 domain

<400> SEQUENCE: 3

Met Ala Val Leu Gly Leu Leu Phe Cys Leu Val Thr Phe Pro Ser Cys
 1               5                  10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Asn Val Met His Trp Val Arg Gln Ala Pro Gly Gln Gly Leu
    50                  55                  60

Glu Trp Met Gly Tyr Ile Asn Pro Tyr Asn Asp Gly Thr Lys Tyr Asn
65                  70                  75                  80

Glu Lys Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asn Trp Asp Val Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255
```

```
Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Ala Leu Pro Ala Pro Ile Glu Lys Thr
        340                 345                 350

Ile Ser Lys Ala Lys Gly Gln Pro Arg Glu Pro Gln Val Tyr Thr Leu
    355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Lys Leu Thr Val Asp Lys Ser
        420                 425                 430

Arg Trp Gln Gln Gly Asn Val Phe Ser Cys Ser Val Met His Glu Ala
    435                 440                 445

Leu His Asn His Tyr Thr Gln Lys Ser Leu Ser Leu Ser Pro Gly Lys
    450                 455                 460

<210> SEQ ID NO 4
<211> LENGTH: 233
<212> TYPE: PRT
<213> ORGANISM: Artificial Sequence
<220> FEATURE:
<223> OTHER INFORMATION: Human frameworks, mouse CDRs
<220> FEATURE:
<221> NAME/KEY: SIGNAL
<222> LOCATION: (1)..(19)
<220> FEATURE:
<221> NAME/KEY: DOMAIN
<222> LOCATION: (20)..(129)
<223> OTHER INFORMATION: Light chain variable domain
<220> FEATURE:
<221> NAME/KEY: MISC_FEATURE
<222> LOCATION: (43)..(53)
<223> OTHER INFORMATION: CDR-L1
<220> FEATURE:
<221> NAME/KEY: MISC_FEATURE
<222> LOCATION: (69)..(75)
<223> OTHER INFORMATION: CDR-L2
<220> FEATURE:
<221> NAME/KEY: MISC_FEATURE
<222> LOCATION: (108)..(116)
<223> OTHER INFORMATION: CDR-L3
<220> FEATURE:
<221> NAME/KEY: DOMAIN
<222> LOCATION: (130)..(233)
<223> OTHER INFORMATION: Light chain constant domain

<400> SEQUENCE: 4

Met Ala Pro Val Gln Leu Leu Gly Leu Leu Val Leu Phe Leu Pro Ala
1               5                   10                  15

Met Arg Cys Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Ile
```

-continued

```
                35                  40                  45
Ser Asp Tyr Leu His Trp Tyr Gln Gln Lys Pro Gly Lys Ala Pro Lys
 50                  55                  60

Leu Leu Ile Tyr Tyr Ala Ser Gln Ser Ile Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Asn Gly His Ser
            100                 105                 110

Phe Pro Phe Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 5
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 5

Glu Val His Leu Gln Gln Ser Gly Pro Glu Leu Val Lys Pro Gly Ala
 1               5                  10                  15

Ser Val Lys Met Ser Cys Lys Ala Ser Gly Tyr Thr Phe Asn Arg Tyr
             20                  25                  30

Leu Ile His Trp Val Lys Gln Lys Pro Gly Gln Gly Leu Glu Trp Ile
         35                  40                  45

Gly Tyr Ile Asn Pro Asn Asn Asp Gly Thr Asn Tyr Asn Glu Lys Phe
     50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Ala Asn Trp Asp Gln Ala Tyr Trp Gly Gln Gly Thr Leu Val Thr
            100                 105                 110

Val Ser Ala
```

-continued

115

<210> SEQ ID NO 6
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 6

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Asn
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Ala Tyr Trp Gly Gln Gly Thr Leu Val Thr
            100                 105                 110

Val Ser Ala
        115

<210> SEQ ID NO 7
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly His Thr Leu Thr Arg Tyr
            20                  25                  30

Leu Met His Trp Val Gln Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

```
Met Glu Leu Ser Ser Leu Thr Ser Glu Asp Ser Ala Val Tyr Tyr Cys
                85                  90                  95

Ala Arg Asn Trp Asp Val Ala Tyr Trp Gly Gln Gly Thr Leu Val Thr
            100                 105                 110

Val Ser Ala
        115

<210> SEQ ID NO 8
<211> LENGTH: 116
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(105)
<223> OTHER INFORMATION: CDRH3

<400> SEQUENCE: 8

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Gly Tyr Trp Gly Gln Gly Thr Thr Leu
            100                 105                 110

Thr Val Ser Ser
        115

<210> SEQ ID NO 9
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

```
Val Met His Trp Val Lys Gln Lys Pro Gly Gln Gly Leu Asp Trp Ile
        35                  40                  45

Gly Tyr Ile Asn Pro Tyr Asn Asp Gly Thr Asn Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Asn Trp Asp Arg Gly Tyr Trp Gly Gln Gly Thr Thr Leu Thr
            100                 105                 110

Val Ser Ser
        115

<210> SEQ ID NO 10
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 10

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Ser Leu Lys Trp Val Lys Gln Arg Thr Gly Gln Gly Leu Glu Trp Ile
        35                  40                  45

Gly Glu Ile His Pro Arg Ser Gly Asn Thr His Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Asp Leu Arg Ser Leu Thr Ser Glu Asp Ser Ala Val Tyr Phe Cys
                85                  90                  95

Ala Thr Asn Trp Asp Leu Gly Tyr Trp Gly Gln Gly Thr Thr Ile Thr
            100                 105                 110

Val Ser Ser
        115

<210> SEQ ID NO 11
<211> LENGTH: 118
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3
```

-continued

```
<400> SEQUENCE: 11

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Ser
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Thr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Met Ile Thr Ala Pro Thr Val Tyr Trp Gly Gln Gly Thr
            100                 105                 110

Leu Val Thr Val Ser Ala
        115

<210> SEQ ID NO 12
<211> LENGTH: 118
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3

<400> SEQUENCE: 12

Gln Val Gln Leu Gln Gln Pro Gly Ala Glu Leu Met Arg Pro Gly Ala
1               5                   10                  15

Ser Val Arg Leu Ser Cys Lys Ala Ser Gly Tyr Ser Phe Thr Thr Ser
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Asn Phe
    50                  55                  60

Lys Asp Lys Ala Thr Leu Thr Val Asp Arg Ser Ser Ser Thr Ala Tyr
65                  70                  75                  80

Met Gln Leu Asn Ser Pro Thr Ser Glu Asp Ser Ala Val Tyr Tyr Cys
                85                  90                  95

Ala Arg Gly Met Ile Thr Ala Pro Ser Val Tyr Trp Gly Gln Gly Thr
            100                 105                 110

Leu Val Thr Val Ser Ala
        115

<210> SEQ ID NO 13
<211> LENGTH: 119
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
```

```
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(108)
<223> OTHER INFORMATION: CDRH3

<400> SEQUENCE: 13
```

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Phe
        35                  40                  45

Gly Asp Ile Asn Pro Asn Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Asp Tyr Tyr Cys
            85                  90                  95

Ala Arg Pro His Tyr Arg Asn Trp Tyr Phe Asp Val Trp Gly Thr Gly
            100                 105                 110

Thr Thr Val Ile Val Ser Ser
        115

```
<210> SEQ ID NO 14
<211> LENGTH: 122
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(111)
<223> OTHER INFORMATION: CDRH3

<400> SEQUENCE: 14
```

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Ile His Trp Val Lys Gln Arg Pro Gly Gln Gly Leu Glu Trp Ile
        35                  40                  45

Gly Trp Ile Phe Pro Gly Ser Gly Asn Thr Lys Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Ala Ser Ala Val Tyr Phe Cys
            85                  90                  95

Ala Arg Glu Gly Leu His Tyr Phe Gly Leu Tyr Ala Met Asp Tyr Trp
            100                 105                 110

Gly His Gly Thr Ser Val Thr Val Ser Ser
        115                 120

```
<210> SEQ ID NO 15
```

```
<211> LENGTH: 124
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(113)
<223> OTHER INFORMATION: CDRH3

<400> SEQUENCE: 15

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Pro Thr Phe
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Ser Pro Pro Tyr Tyr Tyr Asp Ser Thr Tyr Trp Ser Phe Asp
            100                 105                 110

Val Trp Gly Thr Gly Thr Ala Val Thr Val Ser Ser
        115                 120

<210> SEQ ID NO 16
<211> LENGTH: 124
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(113)
<223> OTHER INFORMATION: CDRH3

<400> SEQUENCE: 16

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Asn Tyr
                20                  25                  30

Trp Met Asp Trp Val Lys Gln Arg Pro Gly Gln Gly Leu Glu Trp Ile
            35                  40                  45

Gly Tyr Ile Asn Pro Ser Ser Gly Tyr Val Glu Tyr Asn Gln Lys Phe
    50                  55                  60

Lys Tyr Lys Ala Thr Leu Thr Ala Asp Lys Thr Ser Ser Thr Ala Tyr
65                  70                  75                  80

Met Gln Leu Ser Ser Leu Thr Tyr Asp Asp Ser Ala Val Tyr Tyr Cys
                85                  90                  95
```

```
Ala Arg Ser Pro Pro Tyr Tyr Ala Asn Thr Tyr Trp Ser Phe Asp
            100                 105                 110

Val Trp Gly Thr Gly Thr Thr Val Thr Val Ser Ser
            115                 120
```

```
<210> SEQ ID NO 17
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 17

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Thr Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys Arg
            100                 105
```

```
<210> SEQ ID NO 18
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 18

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Arg Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
```

```
                65                  70                  75                  80
Glu Asp Val Gly Val Tyr Tyr Cys Gln Asn Gly His Ser Phe Pro Phe
                    85                  90                  95

Thr Phe Gly Ser Gly Thr Lys Leu Glu Ile Lys Arg
                100                 105
```

<210> SEQ ID NO 19
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 19

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser His Phe Thr Leu Ser Ile Asn Ser Val Glu Pro
65                  70                  75                  80

Glu Asp Val Gly Val Tyr Tyr Cys Gln Asn Gly His Ser Phe Pro Phe
                    85                  90                  95

Thr Phe Gly Ser Gly Thr Lys Leu Glu Ile Lys Arg
                100                 105
```

<210> SEQ ID NO 20
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 20

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60
```

```
Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Phe
                 85                  90                  95

Thr Phe Gly Ser Gly Thr Lys Leu Glu Ile Lys Arg
            100                 105

<210> SEQ ID NO 21
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 21

Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Asn Tyr
                 20                  25                  30

Leu Thr Trp Tyr Gln Gln Lys Gln Gly Lys Ser Pro Gln Leu Leu Val
             35                  40                  45

Tyr Asn Ala Lys Thr Leu Ala Asp Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His Phe Trp Ser Thr Pro Phe
                 85                  90                  95

Thr Phe Gly Ser Gly Thr Lys Leu Glu Ile Lys Arg
            100                 105

<210> SEQ ID NO 22
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 22

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                 20                  25                  30

Leu His Trp Phe Gln Gln Arg Ser His Glu Ser Pro Arg Leu Leu Ile
             35                  40                  45
```

```
Lys Tyr Ala Ser Gln Ser Ile Ser Gly Ile Pro Ser Arg Phe Ser Gly
         50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Phe
                 85                  90                  95

Thr Phe Gly Ser Gly Thr Lys Leu Glu Ile Lys Arg
                100                 105
```

<210> SEQ ID NO 23
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 23

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                 20                  25                  30

Ala Tyr Ser Tyr Phe His Trp Tyr Gln Gln Lys Pro Gly Gln Pro Pro
                 35                  40                  45

Lys Leu Leu Ile Tyr Leu Ala Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Trp Thr Phe Gly Gly Gly Thr Lys Leu Glu Ile Thr Pro
                100                 105                 110
```

<210> SEQ ID NO 24
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 24

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                 20                  25                  30

Ala Tyr Ser Tyr Phe His Trp Tyr Gln Gln Lys Pro Gly Gln Pro Pro
```

-continued

```
                35                  40                  45
Lys Leu Leu Ile Tyr Leu Ala Ser Asn Leu Glu Ser Gly Val Pro Ala
            50                  55                  60

Arg Phe Ser Gly Ser Gly Ser Gly Thr Asp Phe Thr Leu Asn Ile His
 65                  70                  75                  80

Pro Val Glu Glu Gly Asp Ala Ala Thr Tyr Tyr Cys Gln His Ser Arg
                85                  90                  95

Glu Leu Pro Trp Thr Phe Gly Gly Gly Thr Lys Leu Glu Ile Thr Arg
            100                 105                 110

<210> SEQ ID NO 25
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 25

Asp Ile Val Leu Thr Gln Ser Pro Ala Ser Leu Val Val Ser Leu Gly
 1               5                  10                  15

Gln Arg Ala Thr Ile Ser Cys Arg Ala Ser Lys Ser Val Ser Thr Ser
                20                  25                  30

Gly Tyr Ser Phe Leu Asn Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
            50                  55                  60

Arg Phe Ser Gly Ser Gly Ser Gly Thr Asp Phe Thr Leu Asn Ile His
 65                  70                  75                  80

Pro Val Glu Ala Glu Asp Ala Thr Thr Tyr Tyr Cys Gln His Ser Arg
                85                  90                  95

Glu Leu Pro Leu Thr Phe Gly Ser Gly Thr Lys Leu Glu Met Lys Arg
            100                 105                 110

<210> SEQ ID NO 26
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 26

Asp Ile Gly Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Ala Phe
                20                  25                  30
```

```
Gly Tyr Asn Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Ala Val Glu Glu Glu Asp Ala Ala Thr Tyr Tyr Cys Gln His Ser Arg
                 85                  90                  95

Glu Leu Pro Leu Thr Phe Gly Ala Gly Thr Lys Leu Glu Leu Lys Arg
            100                 105                 110
```

<210> SEQ ID NO 27
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 27

```
Asp Ile Gly Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
             20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
     50                  55                  60

Arg Phe Ser Gly Ser Gly Ser Gly Thr Asp Phe Ile Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Leu Ala Phe Gly Ala Gly Thr Lys Leu Glu Leu Thr Pro
            100                 105                 110
```

<210> SEQ ID NO 28
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 28

```
Asp Ile Gln Met Thr Gln Thr Thr Ser Ser Leu Ser Ala Ser Leu Gly
 1               5                  10                  15
```

```
Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Val Lys Leu Leu Ile
         35                  40                  45

Tyr Tyr Thr Ser Ser Leu His Ser Gly Val Pro Ser Arg Phe Ser Gly
 50                      55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
                     85                  90                  95

Thr Phe Gly Gly Gly Thr Lys Leu Glu Ile Lys Arg
             100                 105
```

<210> SEQ ID NO 29
<211> LENGTH: 170
<212> TYPE: PRT
<213> ORGANISM: Homo sapiens

<400> SEQUENCE: 29

```
Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Thr Thr Asn Asp
         35                  40                  45

Val Pro His Ile Gln Cys Gly Asp Gly Cys Asp Pro Gln Gly Leu Arg
     50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170
```

<210> SEQ ID NO 30
<211> LENGTH: 175
<212> TYPE: PRT
<213> ORGANISM: Mus musculus

<400> SEQUENCE: 30

```
Val Pro Arg Ser Ser Pro Asp Trp Ala Gln Cys Gln Gln Leu Ser
1               5                   10                  15

Arg Asn Leu Cys Met Leu Ala Trp Asn Ala His Ala Pro Ala Gly His
            20                  25                  30

Met Asn Leu Leu Arg Glu Glu Asp Glu Thr Lys Asn Val
         35                  40                  45

Pro Arg Ile Gln Cys Glu Asp Gly Cys Asp Pro Gln Gly Leu Lys Asp
     50                  55                  60

Asn Ser Gln Phe Cys Leu Gln Arg Ile Arg Gln Gly Leu Ala Phe Tyr
```

```
                65                  70                  75                  80
Lys His Leu Leu Asp Ser Asp Ile Phe Lys Gly Glu Pro Ala Leu Leu
                            85                  90                  95

Pro Asp Ser Pro Met Glu Gln Leu His Thr Ser Leu Leu Gly Leu Ser
                100                 105                 110

Gln Leu Leu Gln Pro Glu Asp His Pro Arg Glu Thr Gln Gln Met Pro
            115                 120                 125

Ser Leu Ser Ser Ser Gln Gln Trp Gln Arg Pro Leu Leu Arg Ser Lys
        130                 135                 140

Ile Leu Arg Ser Leu Gln Ala Phe Leu Ala Ile Ala Ala Arg Val Phe
145                 150                 155                 160

Ala His Gly Ala Ala Thr Leu Thr Glu Pro Leu Val Pro Thr Ala
                165                 170                 175

<210> SEQ ID NO 31
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 31

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ile Asn Trp Asp Leu Ala Tyr Trp Gly Gln Gly Thr Leu Val Thr
            100                 105                 110

Val Ser Ala
        115

<210> SEQ ID NO 32
<211> LENGTH: 114
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
```

<223> OTHER INFORMATION: CDRH3

<400> SEQUENCE: 32

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Pro Asn Tyr Asn Glu Asn Phe
    50                  55                  60

Lys Gly Lys Ala Thr Leu Thr Ser Asp Lys Ser Ser Thr Ala Ser
65                  70                  75                  80

Met Glu Leu Ser Ser Leu Thr Ser Glu Asp Ser Ala Val Tyr Tyr Cys
                85                  90                  95

Ala Val Trp Asp Phe Thr Tyr Trp Gly Gln Gly Thr Leu Val Thr Val
            100                 105                 110

Ser Ala

<210> SEQ ID NO 33
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 33

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Lys Asn Trp Asp Lys Gly Tyr Trp Gly Gln Gly Thr Thr Leu Thr
            100                 105                 110

Val Ser Ser
        115

<210> SEQ ID NO 34
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1

```
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 34

Glu Val Gln Leu Gln Gln Ser Gly Pro Glu Leu Leu Lys Pro Gly Ala
1               5                   10                  15

Ser Val Lys Met Ser Cys Lys Ala Ser Ala Tyr Thr Phe Thr Arg Tyr
            20                  25                  30

Leu Ile His Trp Val Lys Gln Lys Pro Arg Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Ala Tyr Trp Gly Gln Gly Thr Leu Val Thr
            100                 105                 110

Val Ser Ala
        115

<210> SEQ ID NO 35
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDR3

<400> SEQUENCE: 35

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ala Tyr
            20                  25                  30

Asn Met His Trp Val Lys Gln Ser His Gly Lys Ser Leu Glu Trp Ile
        35                  40                  45

Gly Tyr Ile Asn Pro Asn Asn Gly Ile Pro Asn Tyr Asn Gln Lys Phe
    50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Phe Tyr Cys
                85                  90                  95

Ala Leu Asn Trp Asp Leu Asp Tyr Trp Gly Gln Gly Thr Thr Leu Ser
            100                 105                 110

Val Ser Ser
        115
```

-continued

```
<210> SEQ ID NO 36
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 36

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Trp Asp Val Thr Cys Trp Gly Gln Gly Thr Leu Val Thr
            100                 105                 110

Val Ser Ala
        115

<210> SEQ ID NO 37
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 37

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Pro Lys Tyr Asn Glu Gln Phe
    50                  55                  60

Lys Gly Lys Ala Thr Leu Thr Ser Asp Lys Ser Ser Asn Thr Ala Tyr
65                  70                  75                  80

Met Glu Leu Ser Ser Leu Thr Ser Glu Asp Ser Ala Val Tyr Tyr Cys
                85                  90                  95
```

```
Ala Arg Asn Trp Asp Val Thr Cys Trp Gly Gln Gly Thr Leu Val Thr
            100                 105                 110

Val Ser Ala
        115

<210> SEQ ID NO 38
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 38

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Ser Asn Trp Asp Val Gly Tyr Trp Gly Gln Gly Thr Thr Leu Thr
            100                 105                 110

Val Ser Ser
        115

<210> SEQ ID NO 39
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 39

Glu Val Gln Leu Lys Gln Ser Gly Leu Glu Val Val Lys Pro Gly Ala
1               5                   10                  15

Ser Val Lys Met Ser Cys Lys Ala Ser Gly Tyr Thr Phe Thr Ala His
            20                  25                  30

Leu Met His Trp Val Lys Gln Arg Pro Gly Gln Gly Leu Glu Trp Ile
        35                  40                  45
```

```
Gly Tyr Ile Asn Pro Tyr Asn Asp Gly Thr Asn Tyr Asn Glu Lys Phe
            50                  55                  60

Lys Gly Lys Ala Thr Leu Thr Ser Asp Lys Ser Ser Ser Thr Ala Phe
 65                  70                  75                  80

Met Glu Leu Ser Ser Leu Thr Ser Glu Asp Ser Ala Val Tyr Tyr Cys
                     85                  90                  95

Ala Ser Asn Trp Asp Val Gly Tyr Trp Gly Gln Gly Thr Thr Leu Thr
                100                 105                 110

Val Ser Ser
        115

<210> SEQ ID NO 40
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 40

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
                35                  40                  45

Gly Tyr Ile Asn Pro Tyr Asn Ala Gly Thr Asn Tyr Asn Glu Lys Phe
            50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                     85                  90                  95

Ala Ser Asn Trp Asp Val Gly Tyr Trp Gly Gln Gly Thr Thr Leu Thr
                100                 105                 110

Val Ser Ser
        115

<210> SEQ ID NO 41
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 41

Glu Val Gln Leu Gln Gln Ser Gly Pro Glu Leu Val Lys Pro Gly Ala
```

```
                 1               5                  10                 15
Ser Val Lys Met Ser Cys Lys Ala Ser Gly Tyr Ser Phe Thr Ser Tyr
                20                  25                 30

Val Met His Trp Val Lys Gln Lys Pro Gly Gln Gly Leu Glu Trp Ile
                35                  40                 45

Gly Tyr Ile Asn Pro Tyr Asn Asp Gly Thr Asn Tyr Asn Glu Lys Phe
                50                  55                 60

Arg Gly Lys Ala Thr Leu Thr Ser Asp Lys Ser Ser Asn Thr Ala Tyr
65                              70                 75                  80

Leu Asp Leu Ser Ser Leu Thr Ser Glu Asp Ser Ala Val Tyr Tyr Cys
                85                  90                 95

Ala Ser Asn Trp Asp Val Gly Tyr Trp Gly Gln Gly Thr Thr Leu Thr
                100                 105                110

Val Ser Ser
       115

<210> SEQ ID NO 42
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 42

Glu Val Gln Leu Gln Gln Ser Gly Pro Glu Leu Val Lys Pro Gly Ala
1               5                  10                 15

Ser Val Lys Met Ser Cys Lys Ala Ser Gly Tyr Thr Phe Thr Ser Tyr
                20                  25                 30

Val Met His Trp Val Lys Gln Lys Pro Gly Gln Gly Leu Glu Trp Ile
                35                  40                 45

Gly Tyr Ile Asn Pro Tyr Asn Asp Gly Thr Asn Tyr Asn Glu Lys Phe
                50                  55                 60

Lys His Lys Ala Thr Leu Thr Ser Asp Lys Ser Ser Ser Thr Ala Tyr
65                              70                 75                  80

Met Glu Leu Ser Ser Leu Thr Ser Glu Asp Ser Ala Val Tyr Tyr Cys
                85                  90                 95

Thr Ser Asn Trp Asp Val Gly Phe Trp Gly Gln Gly Thr Thr Leu Thr
                100                 105                110

Val Ser Ser
       115

<210> SEQ ID NO 43
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
```

```
<220> FEATURE:
<221> NAME/KEY: DOMAIN
<222> LOCATION: (99)..(104)
<223> OTHER INFORMATION: CDRH3

<400> SEQUENCE: 43

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

Leu Ile His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Asn Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Ser Asn Trp Asp Val Gly Tyr Trp Gly Gln Gly Thr Thr Leu Thr
            100                 105                 110

Val Ser Ser
        115

<210> SEQ ID NO 44
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 44

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Gly Ser Leu Thr Ser Glu Asp Ser Ala Val Tyr Tyr Cys
                85                  90                  95

Ala Ser Asn Trp Asp Val Gly Tyr Trp Gly Gln Gly Thr Thr Leu Thr
            100                 105                 110

Val Ser Ser
        115

<210> SEQ ID NO 45
<211> LENGTH: 118
<212> TYPE: PRT
<213> ORGANISM: Mus musculus
```

```
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3

<400> SEQUENCE: 45

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Thr Ile Ser Arg Gly Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Arg Met Ser Ser Leu Arg Ser Glu Asp Thr Ala Leu Tyr Tyr Cys
                85                  90                  95

Ala Arg Trp Pro Phe Ser Tyr Gly Met Asp Tyr Trp Gly Gln Gly Thr
            100                 105                 110

Ser Val Thr Val Ser Ser
        115

<210> SEQ ID NO 46
<211> LENGTH: 118
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3

<400> SEQUENCE: 46

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Asp Met Ser Trp Val Arg Gln Thr Pro Glu Lys Arg Leu Glu Trp Val
        35                  40                  45

Ala Thr Ile Ser Arg Gly Gly Gly Asn Thr Tyr Tyr Pro Asp Ser Val
    50                  55                  60

Lys Ser Arg Phe Thr Ile Ser Arg Asp Asn Ala Lys Asn Asn Leu Tyr
65                  70                  75                  80

Leu Gln Met Ser Ser Leu Arg Ser Val Asp Thr Ala Leu Tyr Tyr Cys
                85                  90                  95

Ser Arg Trp Pro Phe Ser Tyr Ala Met Asp Tyr Trp Gly Gln Gly Thr
            100                 105                 110
```

```
Ser Val Thr Val Ser Ser
        115

<210> SEQ ID NO 47
<211> LENGTH: 118
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3

<400> SEQUENCE: 47

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ser Met Ser Trp Val Arg Gln Thr Pro Glu Lys Arg Leu Glu Trp Val
        35                  40                  45

Ala Thr Ile Ser Arg Gly Gly Asn Thr Tyr Tyr Pro Asp Ser Val
    50                  55                  60

Lys Gly Arg Phe Thr Ile Ser Arg Asp Asn Ala Asn Asn Leu Phe
65                  70                  75                  80

Leu Arg Leu Ser Ser Leu Arg Ser Glu Asp Thr Ala Leu Tyr Tyr Cys
                85                  90                  95

Ala Arg Trp Pro Phe Ser Tyr Gly Met Asp Tyr Trp Gly Gln Gly Thr
            100                 105                 110

Ser Val Thr Val Ser Ser
        115

<210> SEQ ID NO 48
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 48

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
```

```
                65                  70                  75                  80
Glu Asp Val Gly Val Tyr Tyr Cys Gln Asn Gly His Ser Phe Pro Tyr
                        85                  90                  95

Thr Phe Gly Gly Gly Thr Lys Leu Glu Ile Lys Arg
                100                 105

<210> SEQ ID NO 49
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 49

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Arg Ile Ser Asp Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg
                100                 105

<210> SEQ ID NO 50
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 50

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60
```

```
Ser Gly Ser Gly Ser Glu Phe Thr Leu Ser Ile Asn Ser Val Glu Pro
 65                  70                  75                  80

Glu Asp Val Gly Val Tyr Tyr Cys Gln Asn Gly His Ser Phe Pro Phe
                 85                  90                  95

Thr Phe Gly Ser Gly Thr Lys Leu Glu Ile Lys Arg
            100                 105
```

<210> SEQ ID NO 51
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 51

```
Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                 20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Thr Arg Phe Ser Gly
 50                  55                  60

Ser Gly Ser Gly Ser Asp Phe Thr Leu Thr Ile Asn Ser Val Glu Pro
 65                  70                  75                  80

Glu Asp Val Gly Val Tyr Tyr Cys Gln Asn Gly His Ser Phe Pro Phe
                 85                  90                  95

Thr Phe Gly Ser Gly Thr Lys Leu Glu Ile Lys Arg
            100                 105
```

<210> SEQ ID NO 52
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 52

```
Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Arg Asp Tyr
                 20                  25                  30

Leu Tyr Trp Tyr Gln Gln Lys Ser His Glu Ser Pro Arg Leu Leu Ile
             35                  40                  45
```

```
Lys Phe Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg
            100                 105

<210> SEQ ID NO 53
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 53

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr His Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Thr Ile Asn Ser Val Glu Pro
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Glu Ile Lys Arg
            100                 105

<210> SEQ ID NO 54
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 54

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
```

```
                    35                  40                  45
Lys Tyr Ala Ser Gln Ser Ile Ser Gly Ile Pro Ser Arg Phe Ser Gly
         50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Phe
                 85                  90                  95

Thr Phe Gly Ser Gly Thr Lys Leu Glu Ile Lys Arg
             100                 105
```

```
<210> SEQ ID NO 55
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 55

Asp Ile Val Met Ser Gln Ser Pro Ser Ser Leu Ala Val Ser Val Gly
 1               5                  10                  15

Glu Lys Ile Thr Met Thr Cys Lys Ser Ser Gln Thr Leu Leu Tyr Ser
                 20                  25                  30

Ser Asn Gln Lys Asn Phe Leu Ala Trp Tyr Arg Gln Lys Pro Gly Gln
             35                  40                  45

Ser Pro Lys Leu Leu Ile Tyr Trp Thr Ser Thr Arg Glu Ser Gly Val
         50                  55                  60

Pro Asp Arg Phe Thr Gly Ser Gly Ser Gly Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Phe Thr Phe Gly Ser Gly Thr Lys Leu Glu Ile
             100                 105                 110

Lys Arg
```

```
<210> SEQ ID NO 56
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 56

Asp Ile Val Met Ser Gln Ser Pro Ser Ser Val Ala Val Ser Val Gly
 1               5                  10                  15
```

```
Glu Lys Val Thr Met Ser Cys Lys Ser Ser Gln Ser Leu Leu Tyr Ser
            20                  25                  30

Ser Asn Gln Lys Asn Phe Leu Ala Trp Tyr Gln Gln Lys Pro Gly Gln
            35                  40                  45

Ser Pro Lys Leu Leu Ile Phe Trp Thr Ser Thr Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys Arg

<210> SEQ ID NO 57
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 57

Asp Ile Val Met Ser Gln Ser Pro Ser Ser Val Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Phe Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Ile Leu Thr
65                  70                  75                  80

Ile Ser Ser Val Arg Ala Glu Asp Leu Ala Phe Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys Arg

<210> SEQ ID NO 58
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3
```

```
<400> SEQUENCE: 58

Asp Ile Val Met Ser Gln Ser Pro Ser Ser Gln Thr Val Ser Val Gly
1               5                   10                  15

Glu Arg Val Thr Met Ser Cys Lys Ser Ser Gln Ser Leu Leu Tyr Ser
            20                  25                  30

Ser Asn Gln Lys Asn Phe Leu Ala Trp Tyr Gln Gln Lys Pro Gly Gln
        35                  40                  45

Ser Pro Lys Leu Leu Ile His Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Leu Tyr Tyr Cys Gln Gln
                85                  90                  95

Tyr Tyr Ser Tyr Pro Phe Thr Phe Gly Ser Gly Thr Lys Leu Glu Ile
                100                 105                 110

Lys Arg

<210> SEQ ID NO 59
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 59

Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Leu Tyr Ser
            20                  25                  30

Thr Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
                100                 105                 110

Lys Arg

<210> SEQ ID NO 60
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
```

-continued

```
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 60
```

Asp Ile Val Met Ser Gln Ser Pro Ser Ser Leu Pro Val Ser Val Gly
1               5                   10                  15

Glu Lys Val Thr Met Ser Cys Lys Ser Ser Gln Ser Leu Leu Tyr Ser
            20                  25                  30

Ser Ser Gln Lys Asn Tyr Leu Ala Trp Ser Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Ser Tyr Pro Phe Thr Phe Gly Ser Gly Thr Lys Leu Glu Ile
            100                 105                 110

Lys Arg

```
<210> SEQ ID NO 61
<211> LENGTH: 114
<212> TYPE: PRT
<213> ORGANISM: Mus musculus
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 61
```

Asp Ile Val Met Ser Gln Ser Pro Ser Ser Val Ala Val Ser Val Gly
1               5                   10                  15

Glu Lys Val Thr Met Asn Cys Lys Ser Ser Gln Asn Leu Leu Tyr Ser
            20                  25                  30

Ser Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Leu Ala Phe Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys Arg

```
<210> SEQ ID NO 62
<211> LENGTH: 112
<212> TYPE: PRT
<213> ORGANISM: Mus musculus
```

-continued

```
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 62

Asp Ile Val Leu Thr Gln Ser Pro Ala Ser Phe Ala Val Ala Leu Gly
1               5                   10                  15

Gln Arg Ala Thr Ile Ser Cys Arg Ala Ser Lys Ser Val Ser Thr Ser
            20                  25                  30

Asp Tyr Ser Tyr Met His Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

<210> SEQ ID NO 63
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 63

Asp Ile Val Leu Thr Gln Ser Pro Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Asp Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Arg Arg
            100                 105                 110

<210> SEQ ID NO 64
<211> LENGTH: 112
```

```
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 64
```

Asp Ile Val Leu Thr Gln Ser Pro Ala Ser Leu Ala Val Ala Leu Gly
1               5                   10                  15

Gln Arg Ala Thr Ile Ser Cys Arg Ala Ser Lys Ser Val Ser Thr Ser
            20                  25                  30

Asp Tyr Ser Tyr Met His Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Tyr Thr Phe Gly Gly Gly Thr Lys Leu Glu Ile Lys Arg
            100                 105                 110

```
<210> SEQ ID NO 65
<211> LENGTH: 10
<212> TYPE: PRT
<213> ORGANISM: Mus musculus

<400> SEQUENCE: 65
```

Gly Tyr Thr Phe Thr Ser Tyr Leu Met His
1               5                   10

```
<210> SEQ ID NO 66
<211> LENGTH: 17
<212> TYPE: PRT
<213> ORGANISM: Mus musculus

<400> SEQUENCE: 66
```

Tyr Ile Asn Pro Tyr Asn Asp Gly Thr Asn Tyr Asn Glu Lys Phe Lys
1               5                   10                  15

Gly

```
<210> SEQ ID NO 67
<211> LENGTH: 6
<212> TYPE: PRT
<213> ORGANISM: Mus musculus

<400> SEQUENCE: 67
```

Asn Trp Asp Val Gly Tyr
1               5

```
<210> SEQ ID NO 68
<211> LENGTH: 11
<212> TYPE: PRT
<213> ORGANISM: Mus musculus

<400> SEQUENCE: 68
```

Arg Ala Ser Gln Ser Ile Ser Asp Tyr Leu His
1               5                   10

<210> SEQ ID NO 69
<211> LENGTH: 17
<212> TYPE: PRT
<213> ORGANISM: Mus musculus

<400> SEQUENCE: 69

Lys Ser Ser Gln Ser Leu Leu Tyr Ser Asn Gln Lys Asn Phe Leu
1               5                   10                  15
Ala

<210> SEQ ID NO 70
<211> LENGTH: 15
<212> TYPE: PRT
<213> ORGANISM: Mus musculus

<400> SEQUENCE: 70

Arg Ala Ser Lys Ser Val Ser Thr Ser Asp Tyr Ser Tyr Met His
1               5                   10                  15

<210> SEQ ID NO 71
<211> LENGTH: 7
<212> TYPE: PRT
<213> ORGANISM: Mus musculus

<400> SEQUENCE: 71

Tyr Ala Ser Gln Ser Ile Ser
1               5

<210> SEQ ID NO 72
<211> LENGTH: 7
<212> TYPE: PRT
<213> ORGANISM: Mus musculus

<400> SEQUENCE: 72

Trp Ala Ser Thr Arg Lys Ser
1               5

<210> SEQ ID NO 73
<211> LENGTH: 7
<212> TYPE: PRT
<213> ORGANISM: Mus musculus

<400> SEQUENCE: 73

Leu Ala Ser Asn Leu Glu Ser
1               5

<210> SEQ ID NO 74
<211> LENGTH: 9
<212> TYPE: PRT
<213> ORGANISM: Mus musculus

<400> SEQUENCE: 74

Gln Asn Gly His Ser Phe Pro Phe Thr
1               5

<210> SEQ ID NO 75
<211> LENGTH: 9
<212> TYPE: PRT
<213> ORGANISM: Mus musculus

<400> SEQUENCE: 75

Gln Gln Tyr Tyr Ser Tyr Pro Phe Thr
1               5

<210> SEQ ID NO 76
<211> LENGTH: 9
<212> TYPE: PRT
<213> ORGANISM: Mus musculus

<400> SEQUENCE: 76

Gln His Ser Arg Glu Leu Pro Tyr Thr
1               5

<210> SEQ ID NO 77
<211> LENGTH: 10
<212> TYPE: PRT
<213> ORGANISM: Mus musculus
<220> FEATURE:
<221> NAME/KEY: VARIANT
<222> LOCATION: (1)..(1)
<223> OTHER INFORMATION: Can be Gly or Ala
<220> FEATURE:
<221> NAME/KEY: VARIANT
<222> LOCATION: (2)..(2)
<223> OTHER INFORMATION: Can be Tyr, His or Asn
<220> FEATURE:
<221> NAME/KEY: VARIANT
<222> LOCATION: (3)..(3)
<223> OTHER INFORMATION: Can be Thr or Ser
<220> FEATURE:
<221> NAME/KEY: VARIANT
<222> LOCATION: (4)..(4)
<223> OTHER INFORMATION: Can be Phe or Leu
<220> FEATURE:
<221> NAME/KEY: VARIANT
<222> LOCATION: (5)..(5)
<223> OTHER INFORMATION: Can beThr or Asn
<220> FEATURE:
<221> NAME/KEY: VARIANT
<222> LOCATION: (6)..(6)
<223> OTHER INFORMATION: Can be Ser, Arg, Ala, Thr, Cys or Asn
<220> FEATURE:
<221> NAME/KEY: VARIANT
<222> LOCATION: (7)..(7)
<223> OTHER INFORMATION: Can be Tyr, Asn, Cys or His
<220> FEATURE:
<221> NAME/KEY: VARIANT
<222> LOCATION: (8)..(8)
<223> OTHER INFORMATION: Can be Leu, Ile or Val
<220> FEATURE:
<221> NAME/KEY: VARIANT
<222> LOCATION: (9)..(9)
<223> OTHER INFORMATION: Can be Leu, Met or Ile
<220> FEATURE:
<221> NAME/KEY: VARIANT
<222> LOCATION: (10)..(10)
<223> OTHER INFORMATION: Can be His or Asn
<220> FEATURE:
<221> NAME/KEY: VARIANT
<222> LOCATION: (10)..(10)
<223> OTHER INFORMATION: Can be His or Asn

<400> SEQUENCE: 77

Xaa Xaa Xaa Xaa Xaa Xaa Xaa Xaa Xaa Xaa
1               5                   10

<210> SEQ ID NO 78
<211> LENGTH: 17
<212> TYPE: PRT
<213> ORGANISM: Mus musculus
<220> FEATURE:
<221> NAME/KEY: VARIANT
<222> LOCATION: (2)..(2)
<223> OTHER INFORMATION: Can be Ile or Val
<220> FEATURE:
<221> NAME/KEY: VARIANT

```
<222> LOCATION: (5)..(5)
<223> OTHER INFORMATION: Can be Tyr or Asn
<220> FEATURE:
<221> NAME/KEY: VARIANT
<222> LOCATION: (7)..(7)
<223> OTHER INFORMATION: Can be Asp or Ala
<220> FEATURE:
<221> NAME/KEY: VARIANT
<222> LOCATION: (8)..(8)
<223> OTHER INFORMATION: Can be Gly or Val
<220> FEATURE:
<221> NAME/KEY: VARIANT
<222> LOCATION: (9)..(9)
<223> OTHER INFORMATION: Can be Thr or Pro
<220> FEATURE:
<221> NAME/KEY: VARIANT
<222> LOCATION: (10)..(10)
<223> OTHER INFORMATION: Can be Asn or Lys
<220> FEATURE:
<221> NAME/KEY: VARIANT
<222> LOCATION: (14)..(14)
<223> OTHER INFORMATION: Can be Lys, Asn or Gln
<220> FEATURE:
<221> NAME/KEY: VARIANT
<222> LOCATION: (16)..(16)
<223> OTHER INFORMATION: Can be Arg or Lys
<220> FEATURE:
<221> NAME/KEY: VARIANT
<222> LOCATION: (17)..(17)
<223> OTHER INFORMATION: Can be Gly or His

<400> SEQUENCE: 78

Tyr Xaa Asn Pro Xaa Asn Xaa Xaa Xaa Xaa Tyr Asn Glu Xaa Phe Xaa
1               5                   10                  15

Xaa

<210> SEQ ID NO 79
<211> LENGTH: 6
<212> TYPE: PRT
<213> ORGANISM: Mus musculus
<220> FEATURE:
<221> NAME/KEY: VARIANT
<222> LOCATION: (1)..(1)
<223> OTHER INFORMATION: Can be Asn or Arg
<220> FEATURE:
<221> NAME/KEY: VARIANT
<222> LOCATION: (4)..(4)
<223> OTHER INFORMATION: Can be Val, Arg, Leu, Lsy, Gln, Glu or Phe
<220> FEATURE:
<221> NAME/KEY: VARIANT
<222> LOCATION: (5)..(5)
<223> OTHER INFORMATION: Can be Gly, Ala, Asp, Asn or Thr
<220> FEATURE:
<221> NAME/KEY: VARIANT
<222> LOCATION: (6)..(6)
<223> OTHER INFORMATION: Can be Tyr, Cys or Phe

<400> SEQUENCE: 79

Xaa Trp Asp Xaa Xaa Xaa
1               5

<210> SEQ ID NO 80
<211> LENGTH: 11
<212> TYPE: PRT
<213> ORGANISM: Mus musculus
<220> FEATURE:
<221> NAME/KEY: VARIANT
<222> LOCATION: (5)..(5)
<223> OTHER INFORMATION: Can be Ser, Thr or Arg
<220> FEATURE:
<221> NAME/KEY: VARIANT
<222> LOCATION: (7)..(7)
<223> OTHER INFORMATION: Can be Ser or Arg
<220> FEATURE:
<221> NAME/KEY: VARIANT
```

```
<222> LOCATION: (8)..(8)
<223> OTHER INFORMATION: Can be Asp, Ala or His
<220> FEATURE:
<221> NAME/KEY: VARIANT
<222> LOCATION: (9)..(9)
<223> OTHER INFORMATION: Can be Tyr or Phe
<220> FEATURE:
<221> NAME/KEY: VARIANT
<222> LOCATION: (11)..(11)
<223> OTHER INFORMATION: Can be His or Tyr

<400> SEQUENCE: 80

Arg Ala Ser Gln Xaa Ile Xaa Xaa Xaa Leu Xaa
1               5                   10

<210> SEQ ID NO 81
<211> LENGTH: 17
<212> TYPE: PRT
<213> ORGANISM: Mus musculus
<220> FEATURE:
<221> NAME/KEY: VARIANT
<222> LOCATION: (5)..(5)
<223> OTHER INFORMATION: Can be Ser, Asn or Thr
<220> FEATURE:
<221> NAME/KEY: VARIANT
<222> LOCATION: (10)..(10)
<223> OTHER INFORMATION: Can be Ser or Thr
<220> FEATURE:
<221> NAME/KEY: VARIANT
<222> LOCATION: (11)..(11)
<223> OTHER INFORMATION: Can be Asn or Ser
<220> FEATURE:
<221> NAME/KEY: VARIANT
<222> LOCATION: (15)..(15)
<223> OTHER INFORMATION: Can be Phe or Tyr

<400> SEQUENCE: 81

Lys Ser Ser Gln Xaa Leu Leu Tyr Ser Xaa Xaa Gln Lys Asn Xaa Leu
1               5                   10                  15

Ala

<210> SEQ ID NO 82
<211> LENGTH: 15
<212> TYPE: PRT
<213> ORGANISM: Mus musculus
<220> FEATURE:
<221> NAME/KEY: VARIANT
<222> LOCATION: (8)..(8)
<223> OTHER INFORMATION: Can be Thr or Ala
<220> FEATURE:
<221> NAME/KEY: VARIANT
<222> LOCATION: (9)..(9)
<223> OTHER INFORMATION: Can be Ser or Phe
<220> FEATURE:
<221> NAME/KEY: VARIANT
<222> LOCATION: (10)..(10)
<223> OTHER INFORMATION: Can be Asp, Gly or Ala
<220> FEATURE:
<221> NAME/KEY: VARIANT
<222> LOCATION: (12)..(12)
<223> OTHER INFORMATION: Can be Ser or Asn
<220> FEATURE:
<221> NAME/KEY: VARIANT
<222> LOCATION: (13)..(13)
<223> OTHER INFORMATION: Can be Tyr or Phe
<220> FEATURE:
<221> NAME/KEY: VARIANT
<222> LOCATION: (14)..(14)
<223> OTHER INFORMATION: Can be Met, Phe or Leu
<220> FEATURE:
<221> NAME/KEY: VARIANT
<222> LOCATION: (15)..(15)
<223> OTHER INFORMATION: Can be His or Asn

<400> SEQUENCE: 82
```

```
Arg Ala Ser Lys Ser Val Ser Xaa Xaa Xaa Tyr Xaa Xaa Xaa Xaa
1               5                   10                  15

<210> SEQ ID NO 83
<211> LENGTH: 7
<212> TYPE: PRT
<213> ORGANISM: Mus musculus
<220> FEATURE:
<221> NAME/KEY: VARIANT
<222> LOCATION: (1)..(1)
<223> OTHER INFORMATION: Can be Tyr or Phe
<220> FEATURE:
<221> NAME/KEY: VARIANT
<222> LOCATION: (2)..(2)
<223> OTHER INFORMATION: Can be Ala or Thr
<220> FEATURE:
<221> NAME/KEY: VARIANT
<222> LOCATION: (2)..(2)
<223> OTHER INFORMATION: Can be Ala, Val or Thr

<400> SEQUENCE: 83

Xaa Xaa Ser Gln Ser Ile Ser
1               5

<210> SEQ ID NO 84
<211> LENGTH: 7
<212> TYPE: PRT
<213> ORGANISM: Mus musculus
<220> FEATURE:
<221> NAME/KEY: VARIANT
<222> LOCATION: (2)..(2)
<223> OTHER INFORMATION: Can be Ala or Thr
<220> FEATURE:
<221> NAME/KEY: VARIANT
<222> LOCATION: (6)..(6)
<223> OTHER INFORMATION: Can be Lys or Glu

<400> SEQUENCE: 84

Trp Xaa Ser Thr Arg Xaa Ser
1               5

<210> SEQ ID NO 85
<211> LENGTH: 7
<212> TYPE: PRT
<213> ORGANISM: Mus musculus
<220> FEATURE:
<221> NAME/KEY: VARIANT
<222> LOCATION: (6)..(6)
<223> OTHER INFORMATION: Can be Glu or Asp

<400> SEQUENCE: 85

Leu Ala Ser Asn Leu Xaa Ser
1               5

<210> SEQ ID NO 86
<211> LENGTH: 9
<212> TYPE: PRT
<213> ORGANISM: Mus musculus
<220> FEATURE:
<221> NAME/KEY: VARIANT
<222> LOCATION: (8)..(8)
<223> OTHER INFORMATION: Can be Phe or Tyr

<400> SEQUENCE: 86

Gln Asn Gly His Ser Phe Pro Xaa Thr
1               5

<210> SEQ ID NO 87
<211> LENGTH: 9
<212> TYPE: PRT
```

```
<213> ORGANISM: Mus musculus
<220> FEATURE:
<221> NAME/KEY: VARIANT
<222> LOCATION: (1)..(1)
<223> OTHER INFORMATION: Can be Gln or His

<400> SEQUENCE: 87

Xaa Gln Tyr Tyr Ser Tyr Pro Phe Thr
1               5

<210> SEQ ID NO 88
<211> LENGTH: 9
<212> TYPE: PRT
<213> ORGANISM: Mus musculus
<220> FEATURE:
<221> NAME/KEY: VARIANT
<222> LOCATION: (6)..(6)
<223> OTHER INFORMATION: Can be Leu or Phe
<220> FEATURE:
<221> NAME/KEY: VARIANT
<222> LOCATION: (8)..(8)
<223> OTHER INFORMATION: Can be Tyr, Leu or Trp
<220> FEATURE:
<221> NAME/KEY: VARIANT
<222> LOCATION: (9)..(9)
<223> OTHER INFORMATION: Can be Thr or Ala

<400> SEQUENCE: 88

Gln His Ser Arg Glu Xaa Pro Xaa Xaa
1               5

<210> SEQ ID NO 89
<211> LENGTH: 118
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(107)
<223> OTHER INFORMATION: CDRH3

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ala Thr Ile Ser Arg Gly Gly Asn Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Pro Phe Ser Tyr Gly Met Asp Tyr Trp Gly Gln Gly Thr
            100                 105                 110

Leu Val Thr Val Ser Ser
            115
```

```
<210> SEQ ID NO 90
<211> LENGTH: 114
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (26)..(35)
<223> OTHER INFORMATION: CDRL1
<220> FEATURE:
<221> NAME/KEY: DOMAIN
<222> LOCATION: (50)..(66)
<223> OTHER INFORMATION: CDRL2
<220> FEATURE:
<221> NAME/KEY: DOMAIN
<222> LOCATION: (99)..(104)
<223> OTHER INFORMATION: CDRL3

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Asp Tyr Ser Tyr Met His Trp Tyr Gln Gln Lys Pro Gly Gln Ala Pro
        35                  40                  45

Arg Leu Leu Ile Tyr Leu Ala Ser Asn Leu Asp Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ser Arg
                85                  90                  95

Glu Phe Pro Tyr Thr Phe Gly Gln Gly Thr Lys Val Glu Ile Lys Arg
            100                 105                 110

Thr Val

<210> SEQ ID NO 91
<211> LENGTH: 115
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (24)..(38)
<223> OTHER INFORMATION: CDRH1
<220> FEATURE:
<221> NAME/KEY: DOMAIN
<222> LOCATION: (54)..(60)
<223> OTHER INFORMATION: CDRH2
<220> FEATURE:
<221> NAME/KEY: DOMAIN
<222> LOCATION: (93)..(101)
<223> OTHER INFORMATION: CDRH3

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Ala Gly Thr Asn Tyr Asn Glu Lys Phe
    50                  55                  60

Lys Gly Arg Val Thr Met Thr Thr Asp Thr Ser Thr Ser Thr Ala Tyr
```

```
                    65                  70                  75                  80
Met Glu Leu Arg Ser Leu Arg Ser Asp Asp Thr Ala Val Tyr Tyr Cys
                        85                  90                  95

Ala Arg Asn Trp Asp Val Gly Tyr Trp Gly Gln Gly Thr Leu Val Thr
                100                 105                 110

Val Ser Ser
        115

<210> SEQ ID NO 92
<211> LENGTH: 116
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (24)..(40)
<223> OTHER INFORMATION: CDRL1
<220> FEATURE:
<221> NAME/KEY: DOMAIN
<222> LOCATION: (56)..(62)
<223> OTHER INFORMATION: CDRL2
<220> FEATURE:
<221> NAME/KEY: DOMAIN
<222> LOCATION: (95)..(103)
<223> OTHER INFORMATION: CDRL3

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Phe Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gln Gly Thr Lys Val Glu Ile
            100                 105                 110

Lys Arg Thr Val
        115

<210> SEQ ID NO 93
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 93

Glu Val Gln Leu Gln Gln Ser Gly Pro Glu Leu Val Lys Pro Gly Ala
1               5                   10                  15
```

```
Ser Val Lys Met Ser Cys Lys Ala Ser Gly Tyr Thr Phe Thr Cys Cys
            20                  25                  30

Ile Leu His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
 50                      55                  60

Lys Gly Lys Ala Thr Leu Thr Ser Asp Lys Ser Arg Thr Ala Tyr
 65                  70                  75                  80

Met Glu Leu Ser Ser Leu Thr Ser Glu Asp Ser Ala Val Tyr Tyr Cys
                85                  90                  95

Ala Arg Arg Trp Asp Glu Ala Tyr Trp Gly Gln Gly Thr Leu Val Thr
            100                 105                 110

Val Ser Ala
       115
```

```
<210> SEQ ID NO 94
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 94
```

```
Glu Val Gln Leu Gln Gln Ser Gly Pro Glu Leu Val Lys Pro Gly Ala
 1               5                   10                  15

Ser Val Lys Met Ser Cys Lys Ala Ser Gly Tyr Thr Phe Thr Asn Tyr
            20                  25                  30

Leu Met His Trp Val Lys Gln Lys Pro Gly Gln Gly Leu Glu Trp Ile
            35                  40                  45

Gly Tyr Ile Asn Pro Tyr Asn Asp Gly Thr Asn Tyr Asn Glu Lys Phe
 50                      55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Ile Tyr Phe Cys
                85                  90                  95

Thr Ser Asn Trp Asp Leu Asp Tyr Trp Gly Gln Gly Thr Thr Leu Thr
            100                 105                 110

Val Ser Ser
       115
```

```
<210> SEQ ID NO 95
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
```

```
<222> LOCATION: (99)..(104)
<223> OTHER INFORMATION: CDRH3

<400> SEQUENCE: 95

Glu Val Gln Leu Gln Gln Ser Gly Pro Glu Leu Val Lys Pro Gly Ala
1               5                   10                  15

Ser Val Lys Met Ser Cys Lys Ala Ser Gly Asn Thr Phe Thr Arg Tyr
            20                  25                  30

Val Met Asn Trp Val Lys Gln Lys Pro Gly Gln Gly Leu Glu Trp Ile
        35                  40                  45

Gly Tyr Ile Asn Pro Tyr Asn Asp Gly Thr Asn Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Val His Asn Trp Asp Leu Asp Tyr Trp Gly Gln Gly Thr Thr Leu Thr
            100                 105                 110

Val Ser Ser
    115

<210> SEQ ID NO 96
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 96

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Leu Ile His Trp Val Lys Gln Lys Pro Gly Gln Gly Leu Glu Trp Ile
        35                  40                  45

Gly Tyr Val Asn Pro Tyr Asn Asp Gly Thr Asn Tyr Asn Glu Lys Phe
    50                  55                  60

Arg Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Asn Trp Asp Leu Asn Tyr Trp Gly Gln Gly Thr Thr Leu Thr
            100                 105                 110

Val Ser Ser
    115

<210> SEQ ID NO 97
<211> LENGTH: 115
<212> TYPE: PRT
<213> ORGANISM: Mus musculus
<220> FEATURE:
<221> NAME/KEY: DOMAIN
```

```
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 97
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ala Tyr
                20                  25                  30

Leu Ile His Trp Val Lys Gln Ser His Gly Lys Ser Leu Glu Trp Ile
            35                  40                  45

Gly Tyr Ile Asn Pro Asn Asn Gly Thr Asn Tyr Asn Gln Lys Phe
    50                  55                  60

Lys Asp Lys Ala Thr Leu Thr Val Asn Lys Ser Ser Ala Thr Ala Tyr
65                  70                  75                  80

Met Glu Leu Arg Ser Leu Thr Ser Glu Asp Ser Ala Val Phe Tyr Cys
                85                  90                  95

Ser Ser Asn Trp Asp Leu Asp Tyr Trp Gly Arg Gly Thr Thr Leu Thr
                100                 105                 110

Val Ser Ser
        115

```
<210> SEQ ID NO 98
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 98
```

Glu Val Gln Leu Gln Gln Ser Gly Pro Asp Leu Val Lys Pro Gly Ala
1               5                   10                  15

Ser Val Lys Met Ser Cys Lys Ala Ser Gly Tyr Thr Phe Thr Ala Tyr
                20                  25                  30

Leu Ile His Trp Val Lys Arg Ser His Gly Lys Ser Leu Asp Trp Ile
            35                  40                  45

Gly Tyr Ile Asn Pro Asn Asp Gly Val Thr Ser Tyr Asn Gln Lys Phe
    50                  55                  60

Lys Gly Lys Ala Thr Leu Thr Val Asn Lys Ser Ser Gly Thr Ala Tyr
65                  70                  75                  80

Met Glu Leu Arg Ser Leu Thr Ser Glu Asp Ala Ala Val Tyr Tyr Cys
                85                  90                  95

Thr Leu Asn Trp Asp Leu Asp Tyr Trp Gly Gln Gly Thr Thr Leu Thr
                100                 105                 110

Val Ser Ser
        115

```
<210> SEQ ID NO 99
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 99

Gln Ala Gln Leu Gln Gln Ser Gly Ser Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Lys Trp Val Lys Gln Arg Thr Gly Gln Gly Leu Glu Trp Ile
        35                  40                  45

Gly Glu Ile Phe Pro Arg Ser Gly Gln Thr Ile Tyr Asn Glu Asn Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Phe Cys
                85                  90                  95

Ala Ala Asn Trp Asp Leu Asp Tyr Trp Gly Gln Gly Thr Ile Leu Thr
            100                 105                 110

Val Ser Ser
        115

<210> SEQ ID NO 100
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 100

Gln Ala Gln Leu Gln Gln Ser Gly Gly Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Lys Trp Val Lys Gln Gly Thr Gly Gln Gly Leu Glu Trp Ile
        35                  40                  45

Gly Glu Ile Phe Pro Arg Ser Gly Gln Thr Tyr Tyr Asn Glu Lys Phe
    50                  55                  60

Lys Gly Lys Ala Thr Leu Thr Ala Asp Lys Ser Ser Thr Ala Tyr
65                  70                  75                  80
```

```
Met Glu Leu Arg Ser Leu Thr Ser Glu Asp Ser Ala Val Tyr Phe Cys
                85                  90                  95

Ala Ser Asn Trp Asp Leu Asp Tyr Trp Gly Gln Gly Thr Ile Leu Thr
            100                 105                 110

Val Ser Ser
        115

<210> SEQ ID NO 101
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH3

<400> SEQUENCE: 101

Gln Ala Gln Leu Gln Gln Ser Gly Gly Glu Leu Ala Arg Pro Gly Ala
1               5                   10                  15

Ser Val Lys Leu Ser Cys Lys Ala Ser Gly Tyr Thr Phe Thr Asn Tyr
            20                  25                  30

Gly Ile Lys Trp Val Lys Gln Arg Thr Gly Gln Gly Leu Glu Trp Ile
        35                  40                  45

Gly Glu Ile Phe Pro Arg Ser Gly Gln Thr Ile Tyr Asn Glu Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Phe Glu Asp Ser Ala Val Tyr Phe Cys
                85                  90                  95

Ala Ala Asn Trp Asp Leu Asp Tyr Trp Gly Gln Gly Thr Ile Leu Thr
            100                 105                 110

Val Ser Ser
        115

<210> SEQ ID NO 102
<211> LENGTH: 115
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(104)
<223> OTHER INFORMATION: CDRH2

<400> SEQUENCE: 102

Gln Val Gln Leu Gln Gln Ser Gly Gly Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Lys Trp Val Lys Gln Arg Phe Gly Gln Gly Leu Glu Trp Ile
```

-continued

```
                 35                  40                  45
Gly Glu Ile Phe Pro Arg Gly Gly Asn Thr Tyr Tyr Asn Lys Phe
 50                  55                  60

Lys Gly Lys Ala Thr Leu Thr Ala Asp Lys Ser Ser Thr Ala Tyr
 65                  70                  75                  80

Met Glu Leu Arg Ser Leu Thr Ser Glu Asp Ser Ala Val Tyr Phe Cys
                 85                  90                  95

Thr Ala Asn Trp Asp Leu Asp Tyr Trp Gly Gln Gly Thr Thr Leu Thr
                100                 105                 110

Val Ser Ser
        115

<210> SEQ ID NO 103
<211> LENGTH: 119
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(108)
<223> OTHER INFORMATION: CDRH3

<400> SEQUENCE: 103

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Ile Phe Asn Ser Tyr
                 20                  25                  30

Gly Met Ser Trp Val Arg Gln Thr Pro Asp Lys Arg Leu Glu Trp Val
            35                  40                  45

Ala Thr Ile Ser Ser Gly Gly Arg Asn Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Gln Gly Gly Tyr Glu Gly Tyr Val Asp Val Trp Gly Ile Gly
                100                 105                 110

Thr Thr Val Thr Val Ser Ser
        115

<210> SEQ ID NO 104
<211> LENGTH: 122
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(111)
<223> OTHER INFORMATION: CDRH3

<400> SEQUENCE: 104
```

```
Glu Val Ile Leu Val Glu Ser Gly Gly Phe Val Lys Pro Gly Gly
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Thr Pro Asp Lys Gly Leu Glu Trp Val
            35                  40                  45

Ala Thr Ile Ser Thr Gly Gly Arg Tyr Ile Tyr Tyr Ser Asp Thr Val
        50                  55                  60

Lys Gly Arg Phe Thr Ile Ser Arg Asp Asn Ala Lys Ser Thr Leu Tyr
65                  70                  75                  80

Leu Lys Met Ser Ser Leu Arg Ser Glu Asp Thr Ala Val His Phe Cys
                85                  90                  95

Ala Arg His Glu Gly Asp Arg Tyr Tyr Gly Trp Tyr Phe Asp Val Trp
            100                 105                 110

Gly Ala Gly Thr Thr Val Thr Val Ser Ser
            115                 120
```

```
<210> SEQ ID NO 105
<211> LENGTH: 122
<212> TYPE: PRT
<213> ORGANISM: Mus musculus
<220> FEATURE:
<221> NAME/KEY: DOMAIN
<222> LOCATION: (26)..(35)
<223> OTHER INFORMATION: CDRH1
<220> FEATURE:
<221> NAME/KEY: DOMAIN
<222> LOCATION: (50)..(66)
<223> OTHER INFORMATION: CDRH2
<220> FEATURE:
<221> NAME/KEY: DOMAIN
<222> LOCATION: (99)..(111)
<223> OTHER INFORMATION: CDRH3

<400> SEQUENCE: 105
```

```
Glu Val Met Leu Val Glu Ser Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Ser Pro Glu Arg Gly Leu Glu Trp Val
            35                  40                  45

Ala Thr Ile Ser Thr Gly Gly Arg Tyr Thr Phe Tyr Ser Asp Thr Val
        50                  55                  60

Lys Gly Arg Phe Thr Ile Ser Arg Asp Asn Ala Arg Asn Thr Leu Tyr
65                  70                  75                  80

Leu Lys Met Ser Ser Leu Ile Ser Glu Asp Thr Ala Val His Tyr Cys
                85                  90                  95

Ala Arg His Glu Gly Asp Thr Tyr Tyr Gly Trp Tyr Phe Asp Val Trp
            100                 105                 110

Gly Ala Gly Thr Thr Val Thr Val Ser Ser
            115                 120
```

```
<210> SEQ ID NO 106
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
```

```
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 106

Asp Ile Val Met Thr Gln Ser Pro Ala Thr Leu Ser Val Thr Pro Gly
1               5                  10                  15

Asp Arg Val Ser Leu Ser Cys Arg Ala Ser Gln Ser Ile Ser Ala Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Ile Tyr Tyr Cys Gln Asn Gly His Ser Phe Pro Phe
                85                  90                  95

Thr Phe Gly Ser Gly Thr Lys Leu Glu Ile Lys Arg
            100                 105

<210> SEQ ID NO 107
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 107

Asp Ile Val Met Thr Gln Ser Pro Ala Thr Leu Ser Val Thr Pro Gly
1               5                  10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Ile Leu Asn Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg
            100                 105

<210> SEQ ID NO 108
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
```

```
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 108

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser His Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Met Tyr Tyr Cys Gln Asn Gly His Ser Phe Pro Tyr
                85                  90                  95

Thr Phe Gly Gly Gly Thr Lys Leu Glu Ile Lys Arg
                100                 105

<210> SEQ ID NO 109
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 109

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu Tyr Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Phe Cys Gln Asn Gly His Ser Phe Pro Phe
                85                  90                  95

Thr Phe Gly Ser Gly Thr Lys Leu Glu Ile Lys Arg
                100                 105

<210> SEQ ID NO 110
<211> LENGTH: 108
<212> TYPE: PRT
<213> ORGANISM: Mus musculus
<220> FEATURE:
<221> NAME/KEY: DOMAIN
```

```
<222> LOCATION: (24)..(34)
<223> OTHER INFORMATION: CDR-L1
<220> FEATURE:
<221> NAME/KEY: DOMAIN
<222> LOCATION: (50)..(56)
<223> OTHER INFORMATION: CDR-L2
<220> FEATURE:
<221> NAME/KEY: DOMAIN
<222> LOCATION: (89)..(97)
<223> OTHER INFORMATION: CDR-L3

<400> SEQUENCE: 110

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Gly Asp Tyr
                20                  25                  30

Leu His Trp Tyr Gln Gln Lys Leu His Glu Ser Pro Arg Leu Leu Ile
            35                  40                  45

Lys Tyr Ala Ser Arg Ser Ile Ser Gly Ile Pro Ser Arg Phe Ser Gly
        50                  55                  60

Ser Gly Ser Gly Ser Tyr Phe Thr Leu Ser Ile Asn Ser Val Glu Ala
65                  70                  75                  80

Glu Asp Val Gly Val Tyr Phe Cys Gln Asn Gly His Ser Phe Pro Phe
                85                  90                  95

Thr Phe Gly Ser Gly Thr Lys Leu Glu Ile Lys Arg
            100                 105

<210> SEQ ID NO 111
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 111

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Thr Asn Val Glu Pro
65                  70                  75                  80

Glu Asp Val Gly Ile Tyr Tyr Cys Gln Asn Gly His Ser Phe Pro Phe
                85                  90                  95

Thr Phe Gly Ser Gly Thr Lys Leu Glu Ile Lys Arg
            100                 105

<210> SEQ ID NO 112
<211> LENGTH: 108
<212> TYPE: PRT
<213> ORGANISM: Mus musculus
```

-continued

```
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 112

Asp Ile Met Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Arg Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Ile Tyr Tyr Cys Gln Asn Gly His Ser Phe Pro Tyr
                85                  90                  95

Thr Phe Gly Gly Gly Thr Lys Leu Glu Ile Lys Arg
            100                 105

<210> SEQ ID NO 113
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 113

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Phe
            20                  25                  30

Leu His Trp Tyr Arg Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Asp Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys Arg
            100                 105

<210> SEQ ID NO 114
<211> LENGTH: 108
```

```
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 114

Asp Ile Met Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Arg Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Phe Cys Gln Asn Gly His Ser Phe Pro Tyr
                85                  90                  95

Thr Phe Gly Gly Gly Thr Lys Leu Glu Ile Lys Arg
            100                 105

<210> SEQ ID NO 115
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDR-L1
<220> FEATURE:
<221> NAME/KEY: DOMAIN
<222> LOCATION: (50)..(56)
<223> OTHER INFORMATION: CDR-L2
<220> FEATURE:
<221> NAME/KEY: DOMAIN
<222> LOCATION: (89)..(97)
<223> OTHER INFORMATION: CDR-L3

<400> SEQUENCE: 115

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Ser
65                  70                  75                  80

Glu Asp Val Gly Val Tyr Tyr Cys Gln Asn Gly His Ser Phe Pro Phe
                85                  90                  95

Thr Phe Gly Ser Gly Thr Lys Leu Lys Ile Lys Arg
            100                 105
```

```
<210> SEQ ID NO 116
<211> LENGTH: 108
<212> TYPE: PRT
<213> ORGANISM: Mus musculus
<220> FEATURE:
<221> NAME/KEY: DOMAIN
<222> LOCATION: (24)..(34)
<223> OTHER INFORMATION: CDRL1
<220> FEATURE:
<221> NAME/KEY: DOMAIN
<222> LOCATION: (50)..(56)
<223> OTHER INFORMATION: CDRL2
<220> FEATURE:
<221> NAME/KEY: DOMAIN
<222> LOCATION: (89)..(97)
<223> OTHER INFORMATION: CDRL3

<400> SEQUENCE: 116

Asp Ile Val Met Thr Gln Ser His Arg Phe Met Ser Thr Ser Val Gly
1               5                   10                  15

Asp Arg Val Ser Ile Thr Cys Lys Ala Ser Gln Asp Val Ser Ser Ala
            20                  25                  30

Val Ala Trp Tyr Gln Gln Lys Pro Gly Gln Ser Pro Asn Leu Leu Ile
        35                  40                  45

Tyr Ser Ala Ser Phe Arg Asn Thr Gly Val Pro Asp Arg Phe Thr Gly
    50                  55                  60

Ser Gly Ser Gly Thr Asp Phe Thr Phe Thr Ile Ser Gly Val Gln Ala
65                  70                  75                  80

Glu Asp Leu Ala Val Tyr Tyr Cys Gln Gln His His Ser Thr Pro Leu
                85                  90                  95

Thr Phe Gly Ala Gly Thr Lys Leu Glu Leu Lys Arg
            100                 105

<210> SEQ ID NO 117
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 117

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Glu Ser Tyr Met Asn Trp Tyr Gln Gln Lys Pro Gly Gln Pro Pro
        35                  40                  45

Lys Leu Leu Ile Tyr Thr Ser Ser Leu Ala Ser Gly Ile Pro Ala
    50                  55                  60

Arg Phe Ser Gly Ser Gly Ser Gly Thr Asn Phe Thr Leu Asn Ile His
65                  70                  75                  80

Pro Val Glu Glu Glu Asp Ala Ala Thr Tyr Cys Cys Gln Gln Gly Asn
                85                  90                  95

Glu Asp Leu Phe Thr Phe Gly Ser Gly Thr Lys Leu Glu Ile Lys Arg
            100                 105                 110
```

```
<210> SEQ ID NO 118
<211> LENGTH: 112
<212> TYPE: PRT
<213> ORGANISM: Mus musculus
<220> FEATURE:
<221> NAME/KEY: DOMAIN
<222> LOCATION: (24)..(38)
<223> OTHER INFORMATION: CDRL1
<220> FEATURE:
<221> NAME/KEY: DOMAIN
<222> LOCATION: (54)..(60)
<223> OTHER INFORMATION: CDRL2
<220> FEATURE:
<221> NAME/KEY: DOMAIN
<222> LOCATION: (93)..(101)
<223> OTHER INFORMATION: CDRL3

<400> SEQUENCE: 118

Asp Ile Val Leu Thr Gln Ser Pro Ala Ser Leu Ala Val Ser Leu Gly
1               5                   10                  15

Gln Arg Ala Thr Ile Ser Cys Lys Ala Ser His Ser Val Asp Tyr Asp
            20                  25                  30

Val Asp Ser Phe Met Asn Trp Tyr Gln Gln Lys Pro Gly Gln Pro Pro
        35                  40                  45

Lys Leu Leu Ile Phe Ala Ser Ser Leu Glu Ser Gly Ile Pro Ala
    50                  55                  60

Arg Phe Ser Gly Ser Gly Ser Gly Thr Asn Phe Ile Leu Asn Ile His
65                  70                  75                  80

Pro Val Glu Glu Glu Asp Ala Ala Thr Tyr Tyr Cys Gln Gln Gly Asn
                85                  90                  95

Glu Asp Leu Phe Thr Phe Gly Ser Gly Thr Lys Leu Gly Ile Lys Arg
            100                 105                 110

<210> SEQ ID NO 119
<211> LENGTH: 115
<212> TYPE: PRT
<213> ORGANISM: Mus musculus
<220> FEATURE:
<221> NAME/KEY: VARIANT
<222> LOCATION: (31)..(31)
<223> OTHER INFORMATION: can be Ser or Arg
<220> FEATURE:
<221> NAME/KEY: VARIANT
<222> LOCATION: (33)..(33)
<223> OTHER INFORMATION: Can be Leu or Val
<220> FEATURE:
<221> NAME/KEY: VARIANT
<222> LOCATION: (34)..(34)
<223> OTHER INFORMATION: Can be Met or Ile
<220> FEATURE:
<221> NAME/KEY: VARIANT
<222> LOCATION: (59)..(59)
<223> OTHER INFORMATION: Can be Asn or Lys
<220> FEATURE:
<221> NAME/KEY: VARIANT
<222> LOCATION: (97)..(97)
<223> OTHER INFORMATION: Can be Ala or Thr
<220> FEATURE:
<221> NAME/KEY: VARIANT
<222> LOCATION: (98)..(98)
<223> OTHER INFORMATION: Can be Ser or Arg
<220> FEATURE:
<221> NAME/KEY: VARIANT
<222> LOCATION: (102)..(102)
<223> OTHER INFORMATION: Can be Val or Leu
<220> FEATURE:
<221> NAME/KEY: VARIANT
<222> LOCATION: (103)..(103)
<223> OTHER INFORMATION: Can be Gly or Ala
<220> FEATURE:
```

```
<221> NAME/KEY: VARIANT
<222> LOCATION: (110)..(110)
<223> OTHER INFORMATION: Can be Thr or Leu
<220> FEATURE:
<221> NAME/KEY: VARIANT
<222> LOCATION: (111)..(111)
<223> OTHER INFORMATION: Can be Leu or Val
<220> FEATURE:
<221> NAME/KEY: VARIANT
<222> LOCATION: (115)..(115)
<223> OTHER INFORMATION: Can be Ser or Ala

<400> SEQUENCE: 119

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Xaa Tyr
            20                  25                  30

Xaa Xaa His Trp Val Lys Gln Lys Pro Gly Gln Gly Leu Glu Trp Ile
        35                  40                  45

Gly Tyr Ile Asn Pro Tyr Asn Asp Gly Thr Xaa Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Xaa Xaa Asn Trp Asp Xaa Xaa Tyr Trp Gly Gln Gly Thr Xaa Xaa Thr
            100                 105                 110

Val Ser Xaa
        115

<210> SEQ ID NO 120
<211> LENGTH: 98
<212> TYPE: PRT
<213> ORGANISM: Mus musculus

<400> SEQUENCE: 120

Glu Phe Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Tyr Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg

<210> SEQ ID NO 121
<211> LENGTH: 15
<212> TYPE: PRT
<213> ORGANISM: Mus musculus

<400> SEQUENCE: 121

Tyr Phe Asp Tyr Trp Gly Gln Gly Thr Thr Leu Thr Val Ser Ser
1               5                   10                  15

<210> SEQ ID NO 122
<211> LENGTH: 15
```

```
<212> TYPE: PRT
<213> ORGANISM: Mus musculus

<400> SEQUENCE: 122

Trp Phe Ala Tyr Trp Gly Gln Gly Thr Leu Val Thr Val Ser Ala
1               5                   10                  15

<210> SEQ ID NO 123
<211> LENGTH: 95
<212> TYPE: PRT
<213> ORGANISM: Mus musculus

<400> SEQUENCE: 123

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro
                85                  90                  95

<210> SEQ ID NO 124
<211> LENGTH: 95
<212> TYPE: PRT
<213> ORGANISM: Mus musculus

<400> SEQUENCE: 124

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro
                85                  90                  95

<210> SEQ ID NO 125
<211> LENGTH: 101
<212> TYPE: PRT
<213> ORGANISM: Mus musculus
<220> FEATURE:
<221> NAME/KEY: VARIANT
<222> LOCATION: (11)..(11)
<223> OTHER INFORMATION: Can be Leu or Val
<220> FEATURE:
<221> NAME/KEY: VARIANT
<222> LOCATION: (61)..(61)
<223> OTHER INFORMATION: Can be Lys of Glu
<220> FEATURE:
<221> NAME/KEY: VARIANT
<222> LOCATION: (61)..(61)
<223> OTHER INFORMATION: Can be Lys or Glu

<400> SEQUENCE: 125
```

```
Asp Ile Val Met Ser Gln Ser Pro Ser Ser Xaa Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Phe Leu Ala Trp Tyr Gln Gln Lys Pro Gly Gln
        35                  40                  45

Ser Pro Lys Leu Leu Ile Tyr Trp Ala Ser Thr Arg Xaa Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro
            100

<210> SEQ ID NO 126
<211> LENGTH: 101
<212> TYPE: PRT
<213> ORGANISM: Mus musculus

<400> SEQUENCE: 126

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro
            100

<210> SEQ ID NO 127
<211> LENGTH: 99
<212> TYPE: PRT
<213> ORGANISM: Mus musculus
<220> FEATURE:
<221> NAME/KEY: VARIANT
<222> LOCATION: (33)..(33)
<223> OTHER INFORMATION: Can be Asp or Gly

<400> SEQUENCE: 127

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Xaa Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95
```

Glu Leu Pro

<210> SEQ ID NO 128
<211> LENGTH: 99
<212> TYPE: PRT
<213> ORGANISM: Mus musculus

<400> SEQUENCE: 128

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro
```

<210> SEQ ID NO 129
<211> LENGTH: 115
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (26)..(35)
<223> OTHER INFORMATION: CDR-H1
<220> FEATURE:
<221> NAME/KEY: DOMAIN
<222> LOCATION: (50)..(66)
<223> OTHER INFORMATION: CDR-H2
<220> FEATURE:
<221> NAME/KEY: DOMAIN
<222> LOCATION: (99)..(104)
<223> OTHER INFORMATION: CDR-H3

<400> SEQUENCE: 129

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Lys Trp Val Arg Gln Ala Pro Gly Gln Gly Leu Glu Trp Met
        35                  40                  45

Gly Glu Ile Phe Pro Arg Ser Gly Gln Thr Ile Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Trp Asp Leu Asp Tyr Trp Gly Gln Gly Thr Leu Val Thr
            100                 105                 110

Val Ser Ser
        115
```

<210> SEQ ID NO 130
<211> LENGTH: 115
<212> TYPE: PRT

```
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (26)..(35)
<223> OTHER INFORMATION: CDR-H1
<220> FEATURE:
<221> NAME/KEY: DOMAIN
<222> LOCATION: (50)..(66)
<223> OTHER INFORMATION: CDR-H2
<220> FEATURE:
<221> NAME/KEY: DOMAIN
<222> LOCATION: (99)..(104)
<223> OTHER INFORMATION: CDR-H3

<400> SEQUENCE: 130

Gln Val Gln Leu Val Glu Ser Gly Gly Val Val Gln Pro Gly Arg
1               5                   10                  15

Ser Leu Arg Leu Ser Cys Ala Ala Ser Gly Tyr Thr Phe Thr Ser Tyr
            20                  25                  30

Gly Ile Lys Trp Val Arg Gln Ala Pro Gly Lys Gly Leu Glu Trp Val
        35                  40                  45

Ala Glu Ile Phe Pro Arg Ser Gly Gln Thr Tyr Tyr Asn Glu Lys Phe
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asp Leu Asp Tyr Trp Gly Gln Gly Thr Leu Val Thr
            100                 105                 110

Val Ser Ser
        115

<210> SEQ ID NO 131
<211> LENGTH: 108
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (24)..(34)
<223> OTHER INFORMATION: CDR-L1
<220> FEATURE:
<221> NAME/KEY: DOMAIN
<222> LOCATION: (50)..(56)
<223> OTHER INFORMATION: CDR-L2
<220> FEATURE:
<221> NAME/KEY: DOMAIN
<222> LOCATION: (89)..(97)
<223> OTHER INFORMATION: CDR-L3

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Gly His Ser Phe Pro Tyr
```

Thr Phe Gly Gln Gly Thr Lys Val Glu Ile Lys Arg
                100                 105

<210> SEQ ID NO 132
<211> LENGTH: 115
<212> TYPE: PRT
<213> ORGANISM: Artificial Sequence
<220> FEATURE:
<223> OTHER INFORMATION: Human frameworks, rodent CDRs, R98A variant
<220> FEATURE:
<221> NAME/KEY: DOMAIN
<222> LOCATION: (26)..(35)
<223> OTHER INFORMATION: CDR-H1
<220> FEATURE:
<221> NAME/KEY: DOMAIN
<222> LOCATION: (50)..(66)
<223> OTHER INFORMATION: CDR-H2
<220> FEATURE:
<221> NAME/KEY: DOMAIN
<222> LOCATION: (99)..(104)
<223> OTHER INFORMATION: CDR-H3

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Lys Trp Val Arg Gln Ala Pro Gly Gln Gly Leu Glu Trp Met
        35                  40                  45

Gly Glu Ile Phe Pro Arg Ser Gly Gln Thr Ile Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ala Asn Trp Asp Leu Asp Tyr Trp Gly Gln Gly Thr Leu Val Thr
            100                 105                 110

Val Ser Ser
        115

<210> SEQ ID NO 133
<211> LENGTH: 115
<212> TYPE: PRT
<213> ORGANISM: Artificial Sequence
<220> FEATURE:
<223> OTHER INFORMATION: Human frameworks, rodent CDRs, R98A variant
<220> FEATURE:
<221> NAME/KEY: DOMAIN
<222> LOCATION: (26)..(35)
<223> OTHER INFORMATION: CDR-H1
<220> FEATURE:
<221> NAME/KEY: DOMAIN
<222> LOCATION: (50)..(66)
<223> OTHER INFORMATION: CDR-H2
<220> FEATURE:
<221> NAME/KEY: DOMAIN
<222> LOCATION: (99)..(104)
<223> OTHER INFORMATION: CDR-H3

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Thr Ser Tyr
            20                  25                  30

Gly Ile Lys Trp Val Arg Gln Ala Pro Gly Lys Gly Leu Glu Trp Val

-continued

```
          35                    40                    45
Ala Glu Ile Phe Pro Arg Ser Gly Gln Thr Tyr Tyr Asn Glu Lys Phe
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asn Trp Asp Leu Asp Tyr Trp Gly Gln Gly Thr Leu Val Thr
            100                 105                 110

Val Ser Ser
        115
```